US012774437B2

(12) United States Patent
Kodandaramaiah et al.

(10) Patent No.: US 12,774,437 B2
(45) Date of Patent: Oct. 27, 2026

(54) ROBOTIC BARCODE TAGGING OF DISTINCT CELL POPULATIONS IN INTACT TISSUE

(71) Applicant: Regents of the University of Minnesota, Minneapolis, MN (US)

(72) Inventors: Suhasa B Kodandaramaiah, St Paul, MN (US); Daryl M. Gohl, Minneapolis, MN (US); Lyudmila Vulchanova Hart, St. Paul, MN (US); Jacob O'Brien, Hudson, WI (US)

(73) Assignee: Regents of the University of Minnesota, Minneapolis, MN (US)

( * ) Notice: Subject to any disclaimer, the term of this patent is extended or adjusted under 35 U.S.C. 154(b) by 838 days.

(21) Appl. No.: 17/935,494

(22) Filed: Sep. 26, 2022

(65) Prior Publication Data

US 2023/0101853 A1 Mar. 30, 2023

Related U.S. Application Data

(60) Provisional application No. 63/248,823, filed on Sep. 27, 2021.

(51) Int. Cl.
*C12M 3/00* (2006.01)
*C12M 1/00* (2006.01)
(Continued)

(52) U.S. Cl.
CPC ............ *C12M 21/08* (2013.01); *C12M 23/16* (2013.01); *C12M 23/50* (2013.01); *C12M 41/40* (2013.01);
(Continued)

(58) Field of Classification Search
CPC ...... C12M 35/02; C12M 35/04; C12M 35/00; C12M 23/12; C12M 23/16; C12M 23/50;
(Continued)

(56) References Cited

U.S. PATENT DOCUMENTS

| | | | |
|---|---|---|---|
| 7,881,533 B2 | 2/2011 | Ando | |
| 8,173,415 B2 | 5/2012 | Noori et al. | |

(Continued)

FOREIGN PATENT DOCUMENTS

| | | | |
|---|---|---|---|
| EP | 1884780 B1 * | 4/2015 | C12M 35/00 |
| WO | 2008/034249 A1 | 3/2008 | |
| WO | WO-2019051072 A1 * | 3/2019 | C12M 41/08 |

OTHER PUBLICATIONS

"Ogshull/Autoinjector" retrieved from https://github.com/ogshull/Autoinjector—on Jul. 22, 2020, 7 pp.

(Continued)

*Primary Examiner* — Michael L Hobbs
(74) *Attorney, Agent, or Firm* — Shumaker & Sieffert, P.A.

(57) ABSTRACT

A system for injecting a substance into one or more cells of a cell population in a tissue sample, comprising: a robotic manipulator apparatus configured to hold and position a micropipette; an injector controller; a robotic apparatus configured to manipulate a focal plane of a microscope; and a computing device configured to, for each respective cell of the one or more cells of the tissue sample: determine a 3-dimensional location of the respective cell based on images formed by the microscope and captured by a microscope camera; control the robotic manipulator apparatus to insert the micropipette into the respective cell; and control injector controller to eject the substance out of the micropipette and into the respective cell.

22 Claims, 22 Drawing Sheets

(51) Int. Cl.
*C12M 1/34* (2006.01)
*C12M 1/36* (2006.01)
*C12M 3/06* (2006.01)
*G01N 35/00* (2006.01)
*G01N 35/10* (2006.01)

(52) U.S. Cl.
CPC ....... *C12M 41/48* (2013.01); *G01N 35/00693* (2013.01); *G01N 35/109* (2013.01)

(58) Field of Classification Search
CPC ...... C12M 25/02; C12M 21/08; C12M 41/40; C12M 41/48; C12M 41/36; C12N 13/00; C12N 15/87; C12N 15/8207; C12N 15/5206; H03K 3/57; G01N 33/48728; G01N 35/00693; G01N 35/109; G01N 35/0099; G01N 35/1011; G01N 1/28; A61N 1/306; A61K 48/00
See application file for complete search history.

(56) References Cited

U.S. PATENT DOCUMENTS

| | | | |
|---|---|---|---|
| 8,990,023 B2 | 3/2015 | Sun et al. | |
| 9,668,804 B2 | 6/2017 | Kodandaramaiah et al. | |
| 10,596,541 B2 | 3/2020 | Weitz et al. | |
| 11,347,046 B2 | 5/2022 | Moore et al. | |
| 11,712,549 B2 | 8/2023 | Rand | |
| 2002/0149628 A1* | 10/2002 | Smith | G06F 3/04815 715/848 |
| 2004/0181343 A1* | 9/2004 | Wigstrom | B01L 3/502715 702/19 |
| 2008/0077329 A1 | 3/2008 | Sun | |
| 2011/0027885 A1* | 2/2011 | Sun | C12N 15/89 435/375 |
| 2012/0225435 A1 | 9/2012 | Seger et al. | |
| 2014/0309795 A1 | 10/2014 | Norton et al. | |
| 2016/0051353 A1 | 2/2016 | Yanik et al. | |
| 2019/0127782 A1 | 5/2019 | Regev et al. | |
| 2020/0308531 A1 | 10/2020 | Kodandaramaiah et al. | |
| 2021/0180014 A1* | 6/2021 | Rupesh | G01N 33/505 |
| 2022/0309705 A1 | 9/2022 | Kodandaramaiah et al. | |
| 2023/0101853 A1 | 3/2023 | Kodandaramaiah et al. | |
| 2024/0090846 A1 | 3/2024 | Lee et al. | |

OTHER PUBLICATIONS

"Scripy.interpolate.UnivariateSpline." SciPy: Open Source Scientific Tools for Python, retrieved from https://docs.scipy.org/doc/scipy/reference/generated/scipy.interpolate.UnivariateSpline.html, on Jul. 22, 2020, 3 pp.
Abramoff et al., "Image Processing with ImageJ," Biophotonics International, vol. 11, No. 7, Jul. 2004, 7 pp.
Alegria et al., "Single neuron recording: progress towards high-throughput analysis," Future Medicine Ltd, Bioelectronics in Medicine, vol. 3, No. 3, doi: 10.2217/bem-2020-0011, Sep. 17, 2020, pp. 33-36.
Annecchino et al., "Robotic Automation of In Vivo Two-Photon Targeted Whole-Cell Patch-Clamp Electrophysiology." Neuron, vol. 95, No. 5, Aug. 2017, pp. 1048-1055.
Arnold et al., "The T-box transcription factor Eomes/Tbr2 regulates neurogenesis in the cortical subventricular zone," Genes & Development, vol. 22, No. 18, Jul. 2008, 6 pp.
Asp et al., "Spatially Resolved Transcriptomes—Next Generation Tools for Tissue Exploration," BioEssays, vol. 42, No. 10, May 4, 2020, 16 pp.
Attardo et al., "Live Imaging at the Onset of Cortical Neurogenesis Reveals Differential Appearance of the Neuronal Phenotype in Apical versus Basal Progenitor Progeny," PLoS One, vol. 3, No. 6, Jun. 2008, 16 pp.
Bahrey et al., "Voltage-gated Currents, Dye and Electrical Coupling in the Embryonic Mouse Neocortex," Cerebral Cortex, vol. 13, No. 3, Mar. 2003, 13 pp.
Bassett et al., Highly Efficient Targeted Mutagenesis of *Drosophila* with the CRISPR/Cas9 System, Cell Reports, vol. 4, No. 1, Jul. 2013, pp. 220-228.
Becattini et al., "A Fully Automated System for Adherent Cells Microinjection," IEEE Journal of Biomedical and Health Informatics, vol. 18, No. 1, Jan. 2014, 11 pp.
Behjati et al., "What is Next Generation Sequencing?," Arch. Dis. Child. Educ. Pract. Ed., vol. 98, No. 6, Dec. 2013, pp. 236-238.
Caccamo et al, "An Immunohistochemical Characterization of the Primitive and Maturing Neuroepithelial Components in the OTT-6050 Transplantable Mouse Teratoma," Neuropathology and Applied Neurobiology, vol. 15: Mar. 1989, 17 pp.
Cadwell et al., "Electrophysiological, Transcriptomic and Morphologie Profiling of Single Neurons using Patch-Seq," Nat. Biotechnol., vol. 34, No. 2, Feb. 2016, 19 pp.
Canny, "A Computational Approach to Edge Detection," IEEE Transactions on Pattern Analysis and Machine Intelligence , vol. 8, No. 6, doi: 10.1109/TPAMI.1986.4767851, Dec. 1986, pp. 679-698.
Chang et al., "Organ-Targeted High-Throughput In Vivo Biologics Screen Identifies Materials for RNA Delivery," Integrative Biology: Quantitative Biosciences from Nano to Macro, vol. 6, No. 10, Oct. 2014, 17 pp.
Chow et al., "A High-Throughput Automated Microinjection System for Human Cells With Small Size," IEEE/ASME Transactions on Mechatronics, vol. 21, No. 2, Apr. 2016, 13 pp.
Clavaguera et al., "Transmission and spreading of tauopathy in transgenic mouse brain," Nature Cell Biology, vol. 11, No. 7, Jul. 2009, 15 pp.
Costa et al., "Continuous live imaging of adult neural stem cell division and lineage progression in vitro," Development (Cambridge, England), vol. 138, No. 6, Mar. 2011, 12 pp.
Dean, "Microinjection," Brenner's Encyclopedia of Genetics, 2nd Edition, vol. 4, doi:10.1016/8978-0-12-374984-0.00945-1, May 2013, pp. 409-410.
Delpiano et al., "Automated Detection of Fluorescent Cells in In-Resin Fluorescence Sections for Integrated Light and Electron Microscopy," J. Microsc., vol. 271, No. 1, pp. 109-119, Jul. 2018.
Delubac et al., "Microfluidic system with integrated microinjector for automated *Drosophila* embryo injection," The Royal Society of Chemistry, Lab Chip, vol. 12, DOI: 10.1039/c21c40104e, Sep. 2012, pp. 4911-4919.
Dietzl et al., "A genome-wide transgenic RNAi library for conditional gene inactivation in *Drosophila*," Nature, vol. 448, No. 7150, doi: 10.1038/nature05954, Jul. 2007, pp. 151-157.
Farkas et al., "The cell biology of neural stem and progenitor cells and its significance for their proliferation versus differentiation during mammalian brain development," Current Opinion in Cell Biology, vol. 20, No. 6, Dec. 2008, 9 pp.
Fitzharris et al., "Electrical-assisted microinjection for analysis of fertilization and cell division in mammalian oocytes and early embryos [Chapter 19]," Elsevier Inc., Methods in Cell Biology, Ist ed., vol. 144, https://doi.org/10.1016/bs.mcb.2018.03.036, May 2018, pp. 431-440.
Florio et al., "A single splice site mutation in human-specific ARHGAPIIB causes basal progenitor amplification," Science Advances, vol. 2, No. 12, Dec. 2016, 8 pp.
Gompel et al., "*Drosophila* germline transformation," retrieved from http://gompel.org/wp-content/uploads/2015/12/*Drosophila*-transformation-with-chorion.pdf, Oct. 2015, 11 pp.
Gong et al., "Ends-out, or replacement, gene targeting in *Drosophila*," Proceedings of the National Academy of Sciences, PNAS, vol. 100, No. 5, Mar. 2003, pp. 2556-2561.
Gonzalez et al., "Machine Learning-Based Pipette Positional Correction for Automatic Patch Clamp In Vitro," eNeuro, vol. 8, No. 4, Jul. 2021, 8 pp.
Gratz et al., "Genome Engineering of *Drosophila* with the CRISPR RNA-Guided Cas9 Nuclease," Genetics Society of America, Genetics, vol. 194, No. 4. Aug. 2013, pp. 1029-1035.
Gurcan et al., "Histopathological Image Analysis: A Review," IEEE Rev. Biomed. Eng., vol. 2, Oct. 30, 2009, pp. 147-171.

(56) References Cited

OTHER PUBLICATIONS

Harder et al., "Automated Analysis of the Mitotic Phases of Human Cells in 3D Fluorescence Microscopy Image Sequences," in Medical Image Computing and Computer-Assisted Intervention—MICCAI 2006, Feb. 2006, pp. 840-848.
Holst et al., "Autonomous Patch-Clamp Robot for Functional Characterization of Neurons in Vivo: Development and Application to Mouse Visual Cortex," J. Neurophysiol., vol. 121, No. 6, Jun. 2019, pp. 2341-2357.
Hwang et al., "Single-Cell RNA Sequencing Technologies and Bioinformatics Pipelines," Exp. Mol. Med., vol. 50, No. 8, Aug. 2018, 14 pp.
Irshad et al., "Methods for Nuclei Detection, Segmentation, and Classification in Digital Histopathology: A Review—Current Status and Future Potential," IEEE Rev. Biomed. Eng., vol. 7, May 2014, pp. 97-114.
Kalebic et al., "CRISPR/Cas9-induced disruption of gene expression in mouse embryonic brain and single neural stem cells in vivo," EMBO Reports, vol. 17, No. 3, Jan. 2016, 11 pp.
Khosla et al., "Gold Nanorod Induced Warming of Embryos from Cryogenic State Enhances Viability," American Chemical Society, ACS Nano, vol. 11, No. 8, doi: 10.1021/acsnano.7602216, Jul. 2017, pp. 7869-7878.
Kim et al., "A functional genomic screen for cardiogenic genes using RNA interference in developing *Drosophila* embryos," Proceedings of the National Academy of Sciences, PNAS, vol. 101, No. 1, Jan. 2004, pp. 159-164.
Kimmel et al., "Stages of Embryonic Development of the Zebrafish," Wiley-Liss, Inc., Developmental Dynamics, vol. 203, No. 3, doi: 10.1002/aja.1002030302, Jul. 1995, pp. 253-310.
Kodandaramaiah et al., "Automated whole-cell patch-clamp electrophysiology of neurons in vivo," Nature Methods, vol. 9, No. 6, Jun. 2012, 13 pp.
Kodandaramaiah et al., "Multi-Neuron Intracellular Recording in Vivo via Interacting Autopatching Robots," eLife, vol. 7, Jan. 2018, 28 pp.
Kodandaramaiah et al., "Setting up and using the autopatcher for automated intracellular neural recording in vivo," Nature Protocols, vol. 11, No. 4, Apr. 2016, 44 pp.
Kolb et al., "PatcherBot: a Single-Cell Electrophysiology Robot for Adherent Cells and Brain Slices," J. Neural Eng., vol. 16, No. 4, Aug. 2019, 13 pp.
Koos et al., "Automatic Deep Learning-Driven Label-Free Image-Guided Patch Clamp System," Nat. Commun., vol. 12, No. 1, Feb. 2021, 12 pp.
Lacar et al., "Gap junction-mediated calcium waves define communication networks among murine postnatal neural progenitor cells," European Journal of Neuroscience, vol. 34, No. 12, Dec. 2011, 16 pp.
Lawson et al., "In Vivo Imaging of Embryonic Vascular Development Using Trasngenic Zebrafish," Developmental Biology, vol. 248, No. 2, doi:10.1006/dbio.2002.0711, Aug. 2002, pp. 307-318.
Lee et al., "Development of a transient expression assay for detecting environmental oestrogens in zebrafish and medaka embryos," BMC Biotechnology, vol. 12, No. 32, doi: 10.1186/1472-6750-12-32, Jun. 2012, pp. 1-12.
Li et al., "A Robot for High Yield Electrophysiology and Morphology of Single Neurons in Vivo," Nat. Commun., vol. 8, No. 1, Jun. 2017, 10 pp.
Liu et al., "Gap Junctions/Hemichannels Modulate Interkinetic Nuclear Migration in the Forebrain Precursor,". Journal of Neuroscience, vol. 30, No. 12, Mar. 2010, 13 pp.
Long et al., "3D Image-Guided Automatic Pipette Positioning for Single Cell Experiments in Vivo," Scientific Reports, vol. 5, No. 1, Dec. 2015. 8 pp.
Lui et al., "Development and Evolution of the Human Neocortex," Cell, vol. 146, No. 1, Jul. 2011, 19 pp.
Mateos-Pérez et al., "Comparative Evaluation of Autofocus Algorithms for a Real-Time System for Automatic Detection of Mycobacterium Tuberculosis," Cytometry A, vol. 81A, No. 3, Jan. 2012, pp. 213-221.
Millman et al., "Python for Scientists and Engineers," Computing in Science & Engineering, vol. 13, Mar./Apr. 2011, 4pp.
Miyata et al., "Asymmetric production of surface-dividing and non-surface-dividing cortical progenitor cells," Development (Cambridge, England), vol. 131, No. 13, Jul. 2004, 13 pp.
Molotkov et al., "Gene Delivery to Postnatal Rat Brain by Non-ventricular Plasmid Injection and Electroporation," Journal of Visualized Experiments, vol. 43, Sep. 2010, 4 pp.
Nan et al., "Depth Detection for a Stereo Cell Micro-injection System with Dual Cameras," 2017 IEEE International Conference on Robotics and Biomimetics, ROBIO 2017, doi:10.1109/ROBIO.2017.8324565, Dec. 5-8, 2017, pp. 1-6.
O'Brien et al., "Robotic Barcode Tagging of Single Cells in Intact Tissue for Spatial and Functional Transcriptomics," 2020 IEM Annual Conference—Poster Session, 2020 (Applicant points out, in accordance with MPEP 609.04(a), that the year of publication, 2020, is sufficiently earlier than the effective U.S. filing date, so that the particular month of publication is not in issue.), 6 pp.
O'Brien, "Improved Computer Vision Algorithms for High-Throughput Targeting of Single Cells in Intact Tissue for Automated Microinjections," University of Minnesota, Oct. 2021, 148 pp.
Pech-Pacheco et al., "Diatom autofocusing in brightfield microscopy: a comparative study," IEEE, Proceedings 15th International Conference on Pattern Recognition. ICPR-2000, vol. 3, doi: 10.1109/ICPR.2000.903548, Feb. 2000, pp. 314-317.
Permana et al., "A Review of Automated Microinjection Systems for Single Cells in the Embryogenesis Stage," IEEE/ASME Transactions on Mechatronics, vol. 21, No. 5, Oct. 2016, 14 pp.
Pertuz et al., "Analysis of Focus Measure Operators for Shape-From-Focus," Pattern Recognit., vol. 46, No. 5, May 2013, pp. 1415-1432.
Rakic, P., "Evolution of the neocortex: a perspective from developmental biology," Nature Reviews Neuroscience, vol. 10, No. 10, Oct. 2009, 28 pp.
Ren et al., "Faster R-CNN: Towards Real-Time Object Detection with Region Proposal Networks," arXiv, accessed from https://arxiv.org/abs/1506.01497v1, Jun. 2015, 10 pp.
Ringrose et al., "Chapter 1—Transgenesis in Drosophila melanogaster," Transgenesis Techniques, Methods in Molecular Biology, vol. 561, doi:10.1007/978-1-60327-019-9, (Applicant points out, in accordance with MPEP 609.04(a), that the year of publication, 2009, is sufficiently earlier than the effective U.S. filing date, so that the particular month of publication is not in issue.), 2009, pp. 3-19.
Rosen et al., "Microinjection of Zebrafish Embroys to Analyze Gene Function," Journal of Visualized Experiments and Gene Tools, vol. 25, e1115, doi:10.3791/1115, Mar. 2009, 5 pp.
Rubin et al., "Genetic Transformation of *Drosophila* with Transposable Element Vectors," Science, vol. 218, No. 4570, Oct. 1982, pp. 348-353.
Savall et al., "Dexterous robotic manipulation of alert adult Drosophila for high-content experimentation," Nature Methods, vol. 12, No. 7, Jul. 2015, 13 pp.
Schindelin et al., "Fiji: an open-source platform for biological-image analysis," Nature Methods, vol. 9, No. 7, Jul. 2012, 7 pp.
Schubert et al., "Microinjection into zebrafish embryos (*Danio rerio*)—a useful tool in aquatic toxicity testing?," Environmental Sciences Europe, vol. 26, No. 32, doi: 10.1186/s12302-014-0032-3, Dec. 2014, 9 pp.
Schwamborn et al., "The sequential activity of the GTPases Rap 1B and Cdc42 determines neuronal polarity," Nature Neuroscience, vol. 7, No. 9, Aug. 2004, 7 pp.
Shull et al., "Manipulation of Single Neural Stem Cells and Neurons in Brain Slices using RObotic Microinjection," JOVE, jove.com/video/61599, vol. 167, e61599, doi: 10.3791/61599, Jan. 2021, pp. 1-15.
Shull et al., "Robotic platform for microninjection into single cells in brain tissue," EMBO Reports, vol. 20, No. 10, e47880, doi:10.15252/embr.201947880, Aug. 2019, pp. 1-16.

(56) References Cited

OTHER PUBLICATIONS

Simon, "Optimal State Estimation: Kalman, H Infinity, and Nonlinear Approaches," John Wiley & Sons, 2006 (Applicant points out, in accordance with MPEP 609.04(a), that the year of publication, 2006, is sufficiently earlier than the effective U.S. filing date, so that the particular month of publication is not in issue.), 530 pp.
Spradling et al., "Transposition of Cloned P Elements into *Drosophila* Germ Line Chromosomes," Science, vol. 218, No. 4570, doi: 10.1126/science.6289435, Oct. 22, 1982, pp. 341-347.
Sreedhar et al., "Enhancement of Images Using Morphological Transformations," International Journal of Computer Science & Information Technology (IJCSIT), vol. 4, No. 1, DOI : 10.5121/ijcsit.2012.4103, Feb. 2012, pp. 33-50.
Stahl et al., "Visualization and Analysis of Gene Expression in Tissue Sections by Spatial Transcriptomics," Science, vol. 353, No. 6294, Jul. 2016, pp. 78-82.
Stoeckius et al., "Cell Hashing with Barcoded Antibodies Enables Multiplexing and Doublet Detection for Single Cell Genomics," Genome Biology, vol. 19, No. 224, Dec. 19, 2018, 12 pp.
Suk et al., "Closed-Loop Real-Time Imaging Enables Fully Automated Cell-Targeted Patch-Clamp Neural Recording In Vivo," Neuron, vol. 95, No. 5, Aug. 2017, pp. 1037-1047.
Sun et al., "Autofocusing in Computer Microscopy: Selecting the Optimal Focus Algorithm," Microscopy Research and Technique, vol. 65, Oct. 2005, pp. 139-149.
Sun et al., "Biological Cell Injection Using an Autonomous MicroRobotic System," The International Journal of Robotics Research, vol. 21, No. 10-11, Oct.-Nov. 2002, 8 pp.
Takahashi et al., "Manipulating gene expressions by electroporation in the developing brain of mammalian embryos," Differentiation, vol. 70, No. 4-5, Jun. 2002, 8 pp.
Tavano et al., "Insm 1 Induces Neural Progenitor Delamination in Developing Neocortex via Downregulation of the Adherens Junction Belt-Specific Protein Plekha7," Neuron, vol. 97, Mar. 2018, 39 pp.
Taverna et al., "A new approach to manipulate the fate of single neural stem cells in tissue," Nature neuroscience, vol. 15, No. 2, Dec. 2011, 11 pp.
U.S. Appl. No. 17/935,494, filed Sep. 26, 2022, naming inventors Kodandaramaiah et al.
Venken et al., "Genetic Manipulation of Genes and Cells in the Nervous System of the Fruit Fly," Cell Press, Neuron, vol. 72, No. 2, doi: 10.1016/j.neuron.2011.09.021, Oct. 2011, pp. 202-230.
Wong et al., "Microinjection of membrane-impermeable molecules into single neural stem cells in brain tissue," Nature Protocols, vol. 9, No. 5, Apr. 2014, 13 pp.
Wu et al., "Integration of autopatching with automated pipette and cell detection in vitro," American Physiological Society, Journal of Neurophysiology, vol. 116, No. 4, doi: 10.1152/jn.00386.2016, Jul. 2016, pp. 1564-1578.
Xu, "Chapter 10—Visual Servo Control with Force Regulation for Microinjection," Springer International Publishing AG, Micromachines for Biological Micromanipulation, doi.org/10.1007/978-3-319-74621-0 10, Feb. 3, 2018, pp. 209-223.
Yip et al., "Deep Learning-Based Real-Time Detection of Neurons in Brain Slices for in Vitro Physiology," Sci. Rep., vol. 11, No. 1, Mar. 2021, 10 pp.
Zappe et al., "Automated MEMS-based Drosophila embryo injection system for high-throughput RNAi screens," The Royal Society of Chemistry, Lab Chip, vol. 6, DOI: 10.1039/b600238b, Jun. 2006, pp. 1012-1019.
Zhao et al., "A Review of Automated Microinjection of Zebrafish Embryos," MDPI, Micromachines, vol. 10, No. 7, doi: 10.3390/mi10010007, Dec. 24, 2018, 26 pp.
Chi et al., "A Review of Recent Advances in Robotic Cell Microinjection", IEEE Access, Jan. 15, 2020, 13 pp.
Cordero-Maldonado et al., "Deep learning image recognition enables efficient genome editing in zebrafish by automated injections", PLoS One, Jan. 7, 2019, 18 pp.
Mattos et al., "Semi-automated blastocyst microinjection", IEEE International Conference on Robotics and Automation, IEEE, Jun. 2006, 7 pp.
Sadak et al., "Real-time deep learning-based image recognition for applications in automated positioning and injection of biological cells", Computers in Biology and Medicine, vol. 125, Elsevier, Aug. 2020, 11 pp.
Wang et al., "A Fully Automated Robotic System for Microinjection of Zebrafish Embryos", PloS one, Sep. 12, 2007, 7 pp.
Wang et al., "Machine Vision and Image Processing for Automated Cell Injection", 2008 IEEE/ASME International Conference on Mechtronic and Embedded Systems and Applications, IEEE, Oct. 12, 2008, 6 pp.
Wei et al., "A Survey of Force-Assisted Robotic Cell Microinjection Technologies", IEEE Transactions on Automation Science and Engineering, vol. 16, No. 2, IEEE, Apr. 2019, 15 pp.

* cited by examiner

Calibration of micromanipulation

Computer vision cell detection

Trajectory planning, pathfinding, and injection

Kalman filter position estimation and correction

ROBOTIC BARCODE TAGGING OF DISTINCT CELL POPULATIONS IN INTACT TISSUE

This application claims the benefit of U.S. Provisional Patent Application 63/248,823, filed Sep. 27, 2021, the entire content of which is incorporated by reference.

GOVERNMENT RIGHTS

This invention was made with government support under NS112886 and NS111654 awarded by National Institutes of Health. The government has certain rights in the inveniton.

BACKGROUND

Barcode-tagging is a process in which molecular barcodes are bound to or introduced into individual cells of an intact tissue sample. The molecular barcodes may be distinct molecules, such as nucleotide sequences or antibodies, that can be associated with cells, and subsequently detected and uniquely identified in downstream analyses. Cells that are barcode tagged may be tracked and analyzed. For instance, the transcriptome of a barcode tagged cell may be analyzed.

SUMMARY

This disclosure describes techniques in which a robotic microinjection system tags cell populations with molecular barcodes, such as oligonucleotide barcodes, in intact tissue samples. The process of tagging a cell with a molecular barcode may be referred to herein as barcode tagging the cell. Use of the techniques of this disclosure may increase the rate and accuracy at which cells are barcode-tagged as compared to conventional, manual barcode-tagging processes, as well as provide other technical advantages, such as being able to perform microinjections within deeper layers of tissue.

In one example, this disclosure describes a system for injecting a substance into a plurality of cells of a cell population at a plurality of depths in a tissue sample, the system comprising: a robotic manipulator apparatus configured to hold and position a micropipette; an injector controller; a robotic apparatus configured to manipulate a focal plane of the microscope; and a computing device configured to, for each respective cell of the plurality of cells within the tissue sample: determine a 3-dimensional location of the respective cell based on images formed by the microscope and captured by the microscope camera; control the robotic manipulator apparatus to insert the micropipette into the respective cell; and control the injector controller to eject the substance out of the micropipette and into the respective cell.

In another example, this disclosure describes a method for injecting a substance into a plurality of cells of a cell population at a plurality of depths within a tissue sample, the method comprising, for each respective cell of the plurality of cells: determining, by a computing device of a robotic microinjection system, a 3-dimensional location of the respective cell based on images from a microscope camera configured to capture the images formed by a microscope; controlling, by the computing device, a robotic manipulator apparatus to insert a micropipette into the respective cell; and controlling, by the computing device, an injector controller to eject the substance out of the micropipette and into the respective cell.

In another example, this disclosure describes a non-transitory computer-readable storage medium having instructions stored thereon that configure a robotic microinjection system to, for each respective cell of a plurality of cells of a cell population at a plurality of depths within a tissue sample: determine a 3-dimensional location of the respective cell based on images from a microscope camera configured to capture the images formed by a microscope; control a robotic manipulator apparatus to insert a micropipette into the respective cell; and control an injector controller to eject the substance out of the micropipette and into the respective cell.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
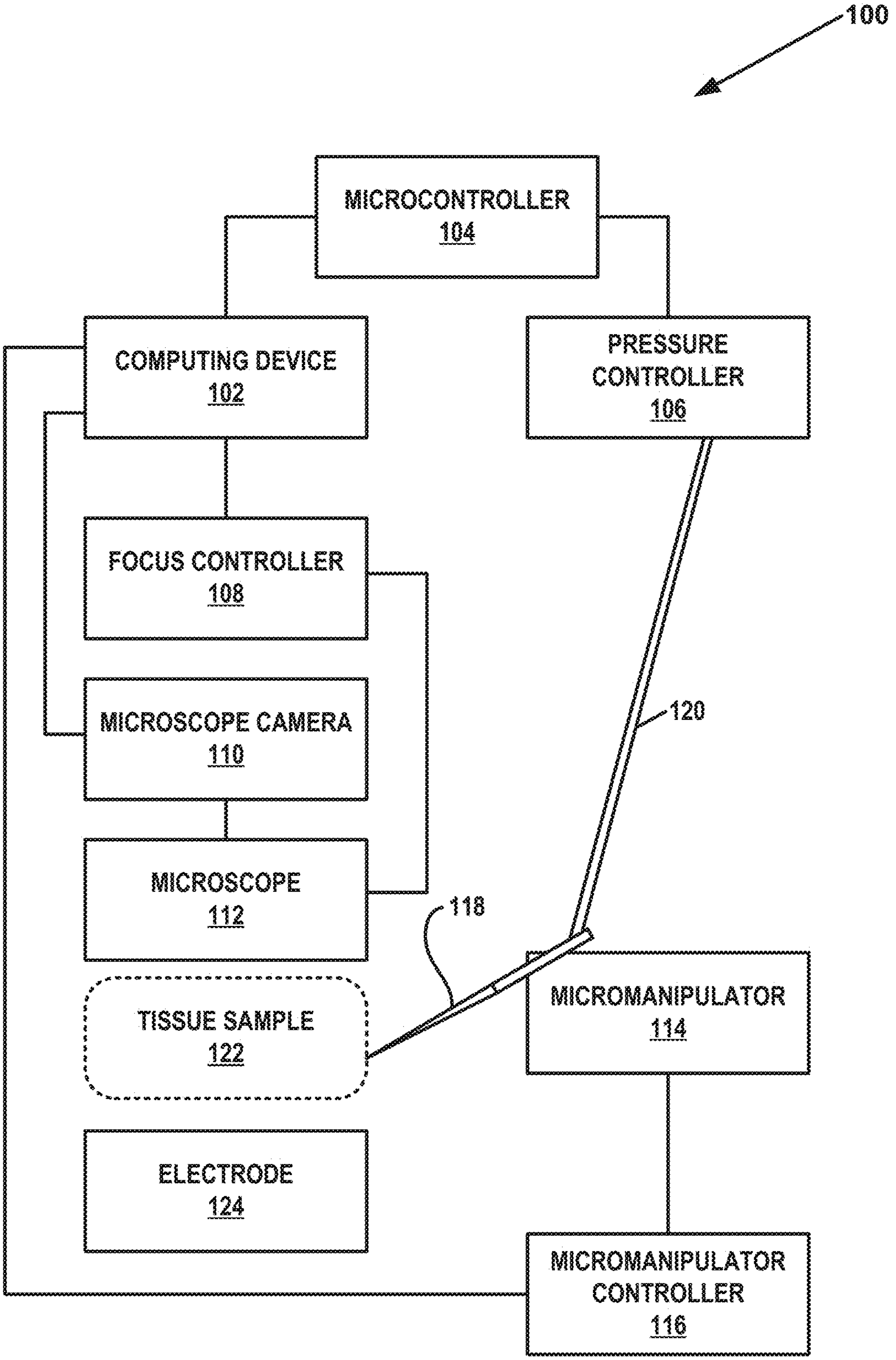
FIG. 1 is a conceptual diagram illustrating an example schematic of an autoinjector according to techniques of this disclosure.

Cells enact their specific role in an organism through gene expression by transcribing DNA to RNA then translating these RNA segments into proteins. While all cells of an organism contain the same genome, different cell populations have distinct gene expression patterns and therefore transcribe distinct sections of DNA to RNA. Through transcriptomic profiling, scientists can elucidate cell populations' gene expression patterns by understanding what RNA transcripts are present in each population. Using massively paralleled Next-Generation Sequencing platforms, scientists are able to conduct rapid, transcriptome wide sequencing of a cell's transcripts in a day that would have previously taken years to complete. However, transcriptomic profiling of heterogenous cell populations obscures the cellular origins of the deciphered gene expression as the gene expression patterns are averaged across cell populations. Single cell transcriptomics remedies this issue by providing transcriptomic information on a single-cellular level thereby contextualizing gene expression on a cell-to-cell basis.

However, the toolkit for single cell transcriptomics is currently lacking the ability to integrate spatial and functional information with transcriptomic measurements at scale. Techniques like patch sequencing (Patch-Seq) which combine functional and transcriptomic profiling are laborious, time consuming, and do not scale easily for analysis on multiple cells in tissue. In contrast, spatial transcriptomics which profiles transcriptomes in a spatially resolved manner lacks the ability to conduct transcriptome wide measurements with cellular resolution. The ability to combine transcriptomic profiling with spatial and functional information of single cells in a scalable manner may be impactful.

Despite the advances in single cell transcriptomics, the contemporary methods suffer from a variety of drawbacks that limit their ability to conduct high-throughput, transcriptome-wide profiling at single-/sub-cellular resolution. For spatial transcriptomics, spatial resolution is limited to approximately 100 μm by the spacing between reverse transcription primers in the barcoded array. Recent iterations have improved the spatial resolution, but the approach still suffers from limited depth as mRNA must permeate the tissue, thereby limiting profiling to superficial cells. In contrast, Patch-seq has excellent spatial resolution as electrophysiological recordings, cytoplasm aspiration, and subsequent sequencing are conducted on individual cells. However, Patch-seq is low-throughput as a technician must manually position the micropipette on the cell membrane, achieve patch-clamp recordings, and draw the cell's contents into the micropipette for RNA sequencing. These steps are laborious and require a high level of training to perform successfully.

Thus, there is currently no technology that allows systematic identification and isolation of multiple cells in tissue for their unique functional, spatial, and/or anatomical features and is capable of carrying out transcriptome-wide analysis at the single cell level. In other words, currently, no technology exists that enables high-throughput single cell transcriptomic profiling of functionally or spatially distinct populations. Once full realized, large scale transcriptomic profiling via barcoded microinjection could be employed for transcriptomic profiling in a vast host of tissues and organs. For instance, it could be applied to study the genetic underpinnings of neurological disorders or profile cancer tumors.

Barcode-tagging is a process in which molecular barcodes are bound to or introduced into individual cells of an intact tissue sample. Barcode-tagging involving an intact tissue sample may be referred to as in situ barcode-tagging. An intact tissue sample is a tissue sample in which the cells of the tissue sample retain the same relative spatial positions as they would in vivo. The molecular barcodes may be distinct molecules, such as nucleotide sequences or antibodies, that can be associated with cells, and subsequently detected and uniquely identified in downstream analyses. Typically, barcode-tagging is performed through chemical bonding of molecular barcodes to the surfaces of cells. In some examples, the molecular barcodes are designed to migrate into the nuclei of the cells. In other examples, the molecular barcodes are designed to attach to the surfaces of the nuclei of the cells, attach to the inner surface of the cell membranes of the cells, or remain suspended in the cytoplasm or nuclei of the cells.

Barcode-tagging on intact tissue samples may be performed by introducing molecular barcodes into a medium of the intact tissue sample. However, the molecular barcodes typically do not bind to cells of the intact tissue beyond an outer layer of cells of the intact tissue sample. Alternatively, barcode-tagging may be performed after disassociation of the tissue sample. In either case, this may limit the utility of barcode-tagging because information regarding cells below the surface of the tissue cannot be derived or information about activity of cells at different spatial positions within an intact tissue sample cannot be derived.

Microinjection is a technique in which substances are introduced into individual cells. However, microinjection is a tedious and time-consuming process. Barcode tagging typically requires a highly trained technician. These constraints limit the number of cells that can be injected within a reasonable time period. As a result, scientific understanding of the tissue may be limited.

Barcoding of cell populations is sometimes accomplished by incubating disaggregated cell suspensions with oligonucleotide-tagged antibodies (a process known as cell hashing). However, such an approach does not preserve information about the spatial locations of cells within a tissue or their physiology. Thus, microinjection of barcoded tags provides a means to barcode cells in situ prior to tissue disaggregation.

In some examples, different molecular barcodes are injected into different cell populations in an intact tissue sample. In some examples, a cell population may be defined as a specific type of cell. The specific type of cell may be defined by a unique morphology, gene or protein expression, physiology, and/or one or more other factors. In some examples, a cell population may be defined in terms of spatial locations of cells within the intact tissue sample. The spatial location of a cell may be defined based on a position of the cell relative to a conceptual 3-dimensional grid overlaid on the intact tissue sample or defined in another way. In some examples, a cell population may be defined as a combination of one or more factors, such as a type of cells, function of cells, and a spatial location of the cells. In other examples, other factors or cell characteristics may be used to define a cell population. For instance, in one example of a cell population being defined by characteristics of cells, the cell population may be defined based on the cells of the population responding to a stimulus in calcium imaging in a specific way. In another example of a cell population being defined by cell characteristics, the cell population may be defined by the presence in the cells of a fluorescent reporter protein introduced by transgenic or viral vector approaches.

Different molecular barcodes, or combinations of molecular barcodes, are injected into cells of different cell populations. For example, different molecular barcodes may be injected into cells at different spatial locations within the intact tissue sample. In some examples, two or more different molecular barcodes may be injected into a single cell to indicate the cell population associated with the cell (e.g., a first molecular barcode indicating a type of the cell and a second molecular barcode indicating a spatial position of the cell). In some examples, a single molecular barcode injected into a single cell may indicate one or both the type of the cell and the spatial location of the cell. In some examples, the molecular barcodes may be antibody-conjugated oligonucleotide barcodes. Antibody-conjugated oligonucleotide barcodes may target the nuclear pore complex or other proteins or cell structures. In some examples, the oligonucleotide barcodes are chemically attached to targets instead of through antibody binding. In some examples, oligonucleotide barcodes are attached to targets directly through chemical bonding that is not antibody-mediated. In some examples, oligonucleotide barcodes are physically present within the targets by being injected into the cytoplasm or nuclei.

After the molecular barcodes are injected into the cells of the tissue sample, the cells of the tissue sample may be disassociated. For instance, in some examples, the cells of the tissue sample may remain intact, but are separated from one another. Thus, disassociation may form a cell suspension. In some examples, such as examples in which the molecular barcodes migrate into the nuclei of the cells or remain attached to the surfaces of the nuclei of the cells, the cell membranes of the cells may be ruptured, and the nuclei of the cells are separated from the remaining portions of the cells. Without barcode tagging of individual cells with molecular barcodes corresponding to the spatial locations of the individual cells, information regarding the spatial locations of the individual cells would otherwise be lost when the cells of the tissue sample are disassociated. Following disassociation of the tissue sample, analysis may be performed on individual cells (which for purposes of this disclosure may also apply to individual nuclei of the cells). Such analysis may include determining the transcriptomes of the individual cells. Analyzing the transcriptomes of the individual cells may be useful for various purposes, such as studying the progression of diseases like cancer, studying neurodegenerative diseases, or elucidating novel cell types. In some examples, a droplet-based single cell sequencing process is used for generating a read out of a transcriptome of the cell. Because the molecular barcode may be a nucleotide sequence, the sequencing process detects the molecular barcode as part of determining the transcriptome of the cell. In this way, the transcriptome of the cell and the cell population of the cell can be determined in the same process.

During the analysis of an individual cell, the molecular barcode injected into the individual cell may be detected. In this way, the cell population of the individual cell may be determined. For instance, the type of the individual cell, as well as the spatial location of the individual cell within the tissue sample, may be determined. Thus, in an example where the analysis determines the transcriptomes of individual cells, differences between the transcriptomes of different types of cells as well as the differences between the transcriptomes of cells at different spatial locations in the tissue sample may be determined. Understanding differences between the transcriptomes of different types of cells and cells at different locations within the tissue sample may further enhance understanding of how the cells function in intact tissue. Although this disclosure is primarily described with respect to the injection of molecular barcodes into cells, the techniques of this disclosure may be applicable to other types of substances, such as cell membrane impermeable dyes. In examples where the techniques of this disclosure are used to inject cell membrane impermeable dyes, the cells may be sorted using fluorescence activated cell sorting (FACS).

This disclosure describes a strategy for spatially resolved transcriptomics that involves microinjection-mediated barcode tagging of single cells. As described herein, nuclei of single cells of interest are labeled via microinjection of, e.g., a barcode conjugated antibody. After barcoded microinjection and transcriptomic profiling, transcriptomic reads can be related back to the original cell through the injected barcodes thereby integrating spatial/anatomical and transcriptomic information into a single approach. For spatially resolved transcriptomics that involves microinjection-mediated barcode tagging of single cells to be viable, microinjection must be carried out at large scale by injecting hundreds of cells in tissue, which is not feasible with manual microinjection.

Previously developed systems lacked features that prevent them from accomplishing automated, targeted, and scalable microinjection. Numerous systems have been developed to achieve automated and targeted patch clamping, but automated patch clamping is fundamentally a low-throughput technique as the goal is to achieve stable recordings from single cells for minutes at a time. This goal contrasts heavily with the need for high-throughput injections to enable hundreds of injections in a single slice. Conversely, a previously developed automated microinjection system has achieved large scale injections into intact tissue described in G. Shull, C. Haffner, W. B. Huttner, S. B. Kodandaramaiah, and E. Taverna, "Robotic platform for microinjection into single cells in brain tissue," EMBO Rep., vol. 20, no. 10, p. e47880, October 2019, doi: 10.15252/embr.201947880. However, this system may lack the ability to target specific single cells as injections target different cell populations by modulating the injection depth into an organotypic slice.

As described in this disclosure, a robotic microinjection system is used for barcode-tagging of cells. The techniques of this disclosure may utilize a computer vision guided robot to access 3D tissue, target functionally and/or spatially defined populations of cells and microinject these identified cells with a unique barcode. Upon completing a series of injections, these steps would be repeated to target cells in a new field of view (FOV). Once the tissue is dissociated, the transcriptomes from the tagged cells can be isolated and analyzed in a high throughput manner. A detailed description of an example robotic microinjection system and example processes for using the robotic apparatus are provided in this disclosure. In one example, this disclosure describes a robotic microinjection system for injecting a substance into a plurality of cells of a cell population at a plurality of depths in a tissue sample. The system comprises a robotic manipulator apparatus configured to hold and position a micropipette, an injector controller, a microscope, a robotic apparatus configured to manipulate a focal plane of the microscope, a microscope camera configured to capture images formed by the microscope, and a computing device. The computing device may be configured to, for each respective cell of the plurality of cells within the tissue sample: determine a 3-dimensional location of the respective cell based on images formed by the microscope and captured the microscope camera, control the robotic manipulator apparatus to insert the micropipette into the respective cell; and control the injector controller to eject the substance out of the micropipette and into the respective cell. In some examples, the substance is a molecular barcode that corresponds to the cell population of interest.

Thus, this disclosure describes a computer-vision guided robotic microinjection system (which may be referred to herein as Robotag-Seq) that is capable of automatically microinjecting hundreds of pre-identified cells in intact tissue. Using computer-vision algorithms, fluorescent cells of interest are located in 3D space and targeted for microinjection with a position-controlled and compensated micropipette needle while a pathfinding algorithm computes the cell-to-cell trajectory of the robot. This platform can enable high-throughput, transcriptome-wide profiling of single cells through the injection of molecular barcodes. Robotag-Seq may be used to elucidate parameters that lead to successful injection in different tissue types, including mouse striatum and spinal cord.

Furthermore, this disclosure describes a strategy for spatially resolved transcriptomics that involves microinjection-mediated barcode tagging of single cells. As described herein, single cells of interest are labeled via microinjection of, e.g., a barcode conjugated antibody, molecular barcode, etc. After barcoded microinjection and transcriptomic profiling, transcriptomic reads can be related back to the original cell through the injected barcodes thereby integrating spatial/anatomical and transcriptomic information into a single approach. The techniques of this disclosure may enable microinjection to be carried out at large scale by injecting hundreds of cells in tissue, which is not feasible with manual microinjection.

FIG. 1 is a conceptual diagram illustrating an example schematic of a robotic microinjection system 100 according to techniques of this disclosure. This disclosure may also refer to robotic microinjection system 100 as an autoinjector. Robotic microinjection system 100 is a platform for injecting molecules of interest, such as molecular barcodes, into cells in intact tissue. In the example of FIG. 1, robotic microinjection system 100 includes a computing device 102, a microcontroller 104, a pressure controller 106, a focus controller 108, a microscope camera 110, a microscope 112, a micromanipulator 114, a micromanipulator controller 116, a micropipette 118, and a pressure line 120. In the example of FIG. 1, robotic microinjection system 100 is set up to inject molecules of interest into cell of a tissue sample 122.

Computing device 102 may be implemented in various ways. For example, computing device 102 may include a personal computer, a laptop computer, a tablet computer, a smartphone, a server computer, or another type of computing device. In some examples, computing device 102 may be located remotely from the other components of robotic microinjection system 100. In some examples, computing device 102 may comprise two or more devices.

In the example of FIG. 1, computing device 102 interfaces with microcontroller 104 to control pressure controller 106, interfaces with focus controller 108 to control a focus of microscope 112, and interfaces with microscope camera 110 to obtain images of tissue sample 122 captured by microscope camera 110 through microscope 112. Microcontroller 104, focus controller 108, and micromanipulator controller 116 may comprise circuitry configured to enable computing device 102 to communicate with and control pressure controller 106, microscope 112, and micromanipulator 114. In some examples, microcontroller 104 is an Arduino Uno. Focus controller 108 may comprise a focus drive permits computing device 102 to control of the fine focus wheel of microscope 112. Thus, focus controller 108 may be a robotic apparatus configured to manipulate a focal plane of microscope 112.

An amplifier and digitizer (Axon Instruments MultiClamp 700b and Axon Instruments Digidata 1440A), which are common components for electrophysiology setups, are used to deliver electrical pulses to an electrode 124 for facilitating cellular penetration. Thus, robotic microinjection system 100 may include electrical hardware configured to perform electroporation on tissue sample 122.

Computing device 102 may use images from microscope camera 110 to control the position of micropipette 118 using micromanipulator 118. Computing device 102 uses pressure controller 106 to precisely deliver injection pressure to micropipette 118 during microinjection. As noted above, computing device 102 may use images from microscope camera 104 to control the position of micropipette 118 using micromanipulator 114. That is, computing device 102 may use actively updated images from microscope camera 110 to determine a current location of micropipette 118 and to control movement of micropipette 118 to move in the correct manner.

Micromanipulator 114 is a 3- or 4-axis micromanipulator that holds micropipette 118. In other words, micromanipulator 114 is a robotic manipulator apparatus configured to hold and position micropipette 118. That is, micromanipulator 114 is a robot used to move the micropipette needle in tissue sample 122 while a pressure controller 106 delivers the payload during injections. In examples where micromanipulator 114 is a 4-axis micromanipulator, micromanipulator 114 has, in addition to x, y, and z axes, a diagonal axis that is in the x-z plane for conducting injections along the axis of micropipette 118. In some examples, micromanipulator 114 is a micromanipulator manufactured by Sensapex, Inc of Oulu, Finland. In other examples, a non-pressure-based control system (e.g., a plunger-based system) is used to eject the payload from the micropipette.

Microscope 112 may be capable of differential image contrast (DIC) and epifluorescence microscopy. Example microscopes may include Olympus BX-50WI, Olympus UMPlanFl 20×/0.5 W, and so on. Microscope 112 has a motorized focus controller configured to control the focus depth of microscope 112. Microscope camera 110 is configured to capture images through microscope 112. Microscope camera 110 may be capable of infrared (IR) imaging. Microscope camera 110 may be manufactured by Hamatsu Photonics of Hamamatsu City, Japan, AXIOCAM™ camera manufactured by Carl Zeiss AG of Oberkochen, Germany, and Dage Labs IR 2000.

In some examples, all components besides the amplifier, digitizer, pressure control system, and computer are located inside a faraday cage to reduce electrical interference. Microscope 112, micromanipulator 114, and focus controller 108 (i.e., a focus drive) may be mounted on an air table (TMC Micro-g 63-534) to dampen vibrations and mitigate mechanical interference.

In general, the process for barcode-tagging (e.g., using antibody-conjugated oligonucleotide barcodes or other substances) of one or more cell populations in a tissue sample involves isolating an initial tissue sample from a host tissue, such as spinal cord tissue or another type of tissue. A technician or slicing machine may then slice the initial tissue sample to create individual 3-dimensional tissue samples, such as tissue sample 122. The individual tissue samples are mounted and immersed in a fluid (e.g., an artificial or biologically derived fluid) that mimics an in vivo environment of the host tissue. In some examples, a technician or machine may add one or more types of fluorescent dye to the tissue samples, in the native animal or after slicing, to increase the visibility of individual cells, or specific types of cells, within the tissue samples. In some examples, cells of the tissue samples may have been genetically manipulated to express fluorescent proteins prior to tissue slicing. A tissue sample may then be brought (e.g., by a technician or machine) to robotic microinjection system 100.

As mentioned above, robotic microinjection system 100 includes micropipette 118. A technician or machine may introduce a solution into micropipette 118. In some examples, the solution contains one or more types of molecular barcodes. Additionally, computing device 102 of robotic microinjection system 100 performs a calibration process that determines a location of micropipette 118, microscope 112, focus controller 108, and microscope camera 110. In other words, to conduct injections, first a micromanipulator 114 coordinate frame is calibrated with the coordinate frame of microscope camera 110 and the coordinate frame of focus controller 108.

After calibration of microscope camera 110, focus controller 108, and micromanipulator 114, computing device 102 of robotic microinjection system 100 performs a process to identify the 3-dimensional locations of individual cells within tissue sample 122. Computing device 102 may identify the 3-dimensional locations of individual cells using images from microscope camera 110 generated using epifluorescence or DIC microscopy. In some examples, the process to identify the 3-dimensional locations of the individual cells within tissue sample 122 is a computer vision process, such as a machine learning-based computer vision process or other type of computer vision process. The process of identifying the 3-dimensional locations of individual cells within tissue sample 122 may involve the use of thresholding operations to determine x and y coordinates of cells. The process of identifying the 3-dimensional locations of individual cells within tissue sample 122 may involve the use of focal adjustments to determine z coordinates of cells.

In some examples, computing device 102 of robotic microinjection system 100 applies a machine-learned neural network (NN) (e.g., a convolutional NN) to one or more of the images to determine the 3-dimensional locations of individual cells. In some examples, the machine-learned neural network (NN) may be a segmentation network like U-Net or Mask R-CNN. In one example, machine learned neural network (NN) running on the computing device 102 may perform image segmentation on each image in one or a plurality of images in a z-stack of images to segment for cells. In this example, the three-dimensional centroids of the cells may be acquired from the image segmentation results. An example of using a CNN is provided below with respect to FIG. 15.

In some examples, images captured by microscope camera 110 are a z-stack of images of tissue sample 122 while scanning through a volume of tissue sample 122. Computing device 102 of robotic microinjection system 100 generates a maximum intensity projection (MIP) based on the z-stack of images. Computing device 102 may then segment the one or more cells from the MIP. For each respective cell of the one or more cells, computing device 102 may determine a z-coordinate of the respective cell based on a most in-focus optical section of the respective cell. In some examples, as part of determining the z-coordinate of the respective cell, computing device 102 may compute a focus metric (e.g., as a pixel intensity, a Tenengrad variance, a normalized variance, or a Vollath's autocorrelation) for each image of the z-stack for the respective cell. In this example, computing device 102 may fit a gaussian distribution to the focus metric for the images and select a mean of the gaussian distribution as the z-coordinate of the respective cell.

After determining the 3-dimensional locations of the individual cells, computing device 102 may maneuver micropipette 118 to inject the solution containing the one or more molecular barcodes into the individual cells of tissue sample 122. In other words, micropipette trajectories are computed, micropipette 118 is guided to each of the detected cells, and a molecular barcode is injected into the cells under the control of pressure controller 106 (i.e., an injector controller, such as a microcontroller actuated pressure regulator). Computing device 102 may perform a computer vision or machine learning algorithm and Kalman filter to localize the micropipette tip and correct for positioning inaccuracy. In some examples, robotic microinjection system 100 applies electroporation to increase the permeability of cell membranes to micropipette 118. For instance, an amplifier and digitizer, which are commonly used in patch-clamping, may be used to deliver electrical pulses to the micropipette that facilitate cellular penetration. Micropipette 118 penetrates through the cell membrane of the cells.

After robotic microinjection system 100 injects the solution into the cells of tissue sample 122, the tissue sample may be removed from robotic microinjection system 100 (e.g., by a technician or machine). In some examples, prior to performing further analysis on tissue sample 122, one or more enrichment processes may be performed to increase the proportion of barcoded cells available for the further analysis. For example, flow sorting based on fluorescence may be performed after disassociation of the cells of the tissue sample to reduce the number of cells that are not labeled by the fluorescent dye. Because robotic microinjection system 100 injects cells that are labeled by the fluorescent dye, removing unlabeled cells may increase the proportion of remaining cells that were barcoded. In another example, barcode-tagged cells may be separated from other cells using pulldown strategies such as magnetic beads that bind the tag. In another example, portions of the tissue sample not containing barcoded cells may be physically removed prior to disassociation of the cells of tissue sample 122.

In some examples, following injections, single-cell transcriptional profiling is performed by obtaining fluorescently labeled nuclei of interest using fluorescence-assisted nuclear sorting or other enrichment methods. A 10× Genomic library or equivalent may then be constructed, sequenced, and analyzed. The microinjected barcodes associate the transcriptome data with the spatial/functional/physiological measurements.

To profile transcriptomes in a spatial resolved manner, other methods have foregone microinjection in favor of patch clamping as in Patch-seq or arrays of reverse transcription primers paired with unique barcodes as in spatial transcriptomics. In Patch-seq, functional information is obtained by a conducting whole-cell patch clamp on a cell before the cellular contents are extracted for later RNA sequencing. Patch-seq is therefore capable of spatial and functional transcriptomics at single cellular resolution, but it suffers the same critical drawback as manual microinjection: low-throughput. Patch-seq is arguably more difficult and tedious than manual microinjection because the pipette must be located precisely next to the cell membrane while the cell membrane is drawn into the pipette and recording is being conducted as opposed to simply impaling, injecting, and exiting the cell during microinjection. In contrast, spatial transcriptomics is conducted by placing tissue sections atop of an array of reverse transcription primers paired with unique positional barcodes. The tissue's mRNA permeates through the tissue and attaches to the reverse transcription primer. After RNA sequencing, the transcriptomic information can be related back to its locational/functional/anatomical features in the tissue via the unique barcode. While this approach is higher throughput because whole tissue sections can be analyzed in a single trial, it lacks single cellular specificity. During mRNA permeation, mRNA from the surrounding tissue above the reverse transcription primers becomes attached to the primer. Consequently, mRNA from a single cell or from multiple cells localized near the primer may become attached thereby reducing spatial transcriptomics' cellular resolution. Other emerging approaches for spatial/functionally resolved transcriptome profiling like NanoString's hybridization-based approach Reedcoor's/Cartana's in-situ sequencing-based approach have achieved high spatial resolution, but they are limited by the ability to get reagents into tissue. This limitation only allows transcriptome profiling to a shallow depth of a few microns below the tissue surface. Because of the low-throughput nature of Patch-seq, the relatively lower cellular resolution of spatial transcriptomics, and the depth limitation of emerging techniques, the automated barcoded microinjection of this disclosure may improve upon these technologies by providing a platform for conducting spatial and functional transcriptomics at scale and with single cell resolution with depths of hundreds of microns below the tissue surface. In this disclosure, the depth of a cell may refer to a distance of the cell below a surface of the tissue sample.

Figure 2:
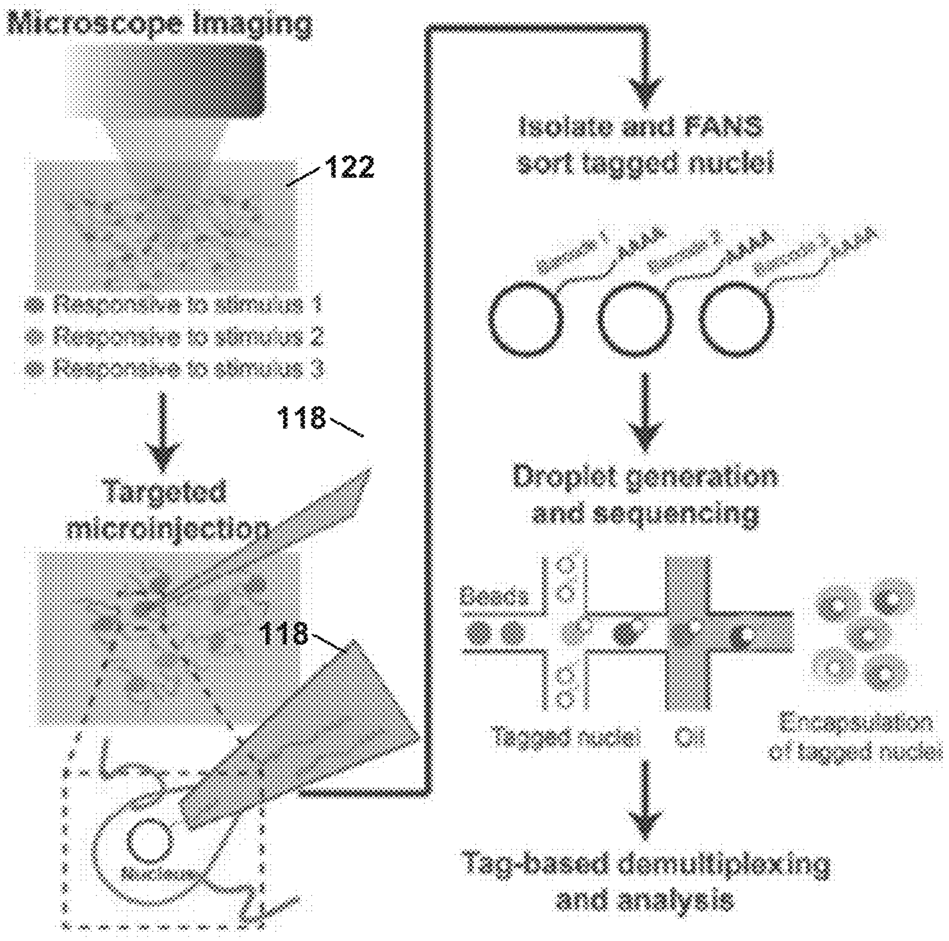
FIG. 2 is a conceptual diagram illustrating an example methodology for barcoded microinjection and transcriptomic profiling according to techniques of this disclosure.

FIG. 2 is a conceptual diagram illustrating an example methodology for barcoded microinjection and transcriptomic profiling according to techniques of this disclosure. In the example of FIG. 2, robotic microinjection system 100 is programmed to microinject multiple functionally identified cells in intact brain tissue with unique barcodes, such as oligonucleotide barcode-antibody conjugate, targeting the nuclear pore complex that can be retrieved during later transcriptomic profiling. Although FIG. 2 is described with respect to brain tissue, techniques of this disclosure may be applied with respect to other tissue types, such as skin tissue, kidney tissue, liver tissue, muscle tissue, and so on. The molecular barcodes relate the profiled transcriptomes with the functionally identified cells in tissue thereby integrating spatial and/or functional, and transcriptomic information into a single approach.

In the example of FIG. 2, functionally distinct cells that are responsive to unique stimuli are identified and targeted for barcoded microinjection. For instance, microscope imaging via microscope 112 and microscope camera 110 may be used to identify three cell populations in tissue sample 122. Each of the cell populations is responsive to a different stimulus. Robotic microinjection system 100 may maneuver micropipette 118 to inject a substance into individual cells of a specific cell population in tissue sample 122. The substance may attach itself to nuclei of the cells. After injecting different substances into cells of the different cell populations, the cell nuclei may be isolated from tissue sample 122. Beads may be attached to the cell nuclei, which are then encapsulated. Tag-based demultiplexing may then be applied to the encapsulated cell nuclei and beads and analysis may be performed. For instance, fluorescence assisted nuclei sorting (FANS) may be performed, in which a fluorescent label is injected that attaches to or is retained within the nucleus and the nuclei are sorted (i.e., enriched) after the nuclei are isolated from the cells. Post-injection nuclei sorting, sequencing, and barcode retrieval contextualizes transcriptomic information within the tissue's functional/spatial/anatomical framework.

Figures 3A, 3B, 3C:
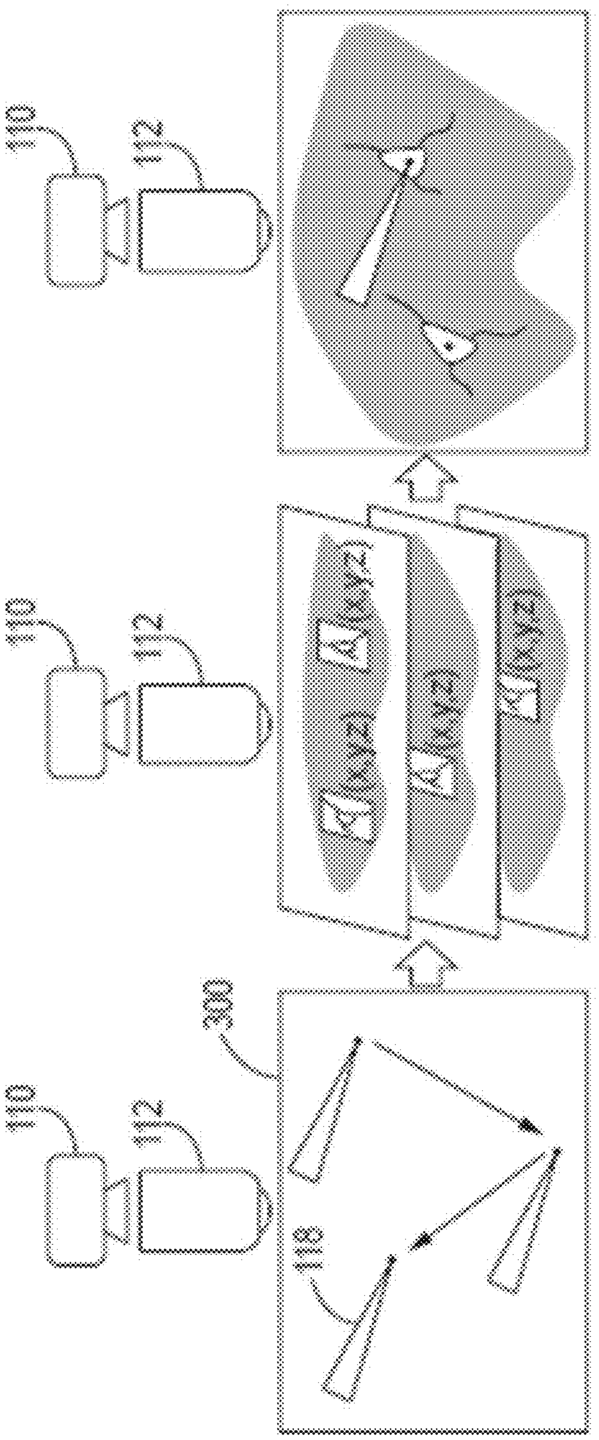
FIGS. 3A-3G are conceptual diagrams illustrating an example autoinjection process according to techniques of this disclosure.

FIGS. 3A-3C are conceptual diagrams illustrating an example autoinjection process according to techniques of this disclosure. In FIG. 3A, robotic microinjection system 100 detects micropipette 118 in an image 300 generated by microscope camera 110. Micromanipulator 114 is calibrated to the camera's field of view (FOV) and focus controller 108 (i.e., a focus drive) to determine the location of micromanipulator 114 in 3D space. After the calibration is complete, the x, y, and z coordinates of micromanipulator 114 are defined relative to microscope camera 110 and focus controller 108 which permit micromanipulator 114 to be positioned at precise coordinates in 3D space within the FOV. This allows micromanipulator 114 to target cells whose positions will also be defined relative to the same camera and focus drive coordinates. In FIG. 3B, robotic microinjection system 100 performs tissue scanning, machine learning cell detection, and cell position acquisition. In FIG. 3C, robotic microinjection system 100 executes micropipette trajectories and performs barcoded cell injections.

Thus, FIGS. 3A-3C show a procedure for conducting robot-assisted, automated microinjection into intact tissue slices that includes three high-level steps. First, micromanipulator 114 is calibrated to microscope camera 110 and focus controller 108 of microscope 112 to determine the location of micromanipulator 114 in 3D space. Next, robotic microinjection system 100 automatically scans through a user-defined volume of tissue and a computer-vision algorithm or machine learned neural network automatically locates cells in 3D space and selects cells for targeted injection. Once the locations of micromanipulator 114 and the cells are known, computing device 102 computes a trajectory for micromanipulator 114 (i.e., a robot) and attempts injections on the selected cells while another computer vison algorithm corrects for robotic positioning inaccuracies.

Figure 3D:
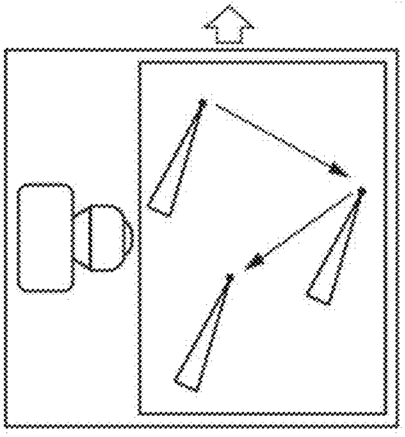
Figure 3E:
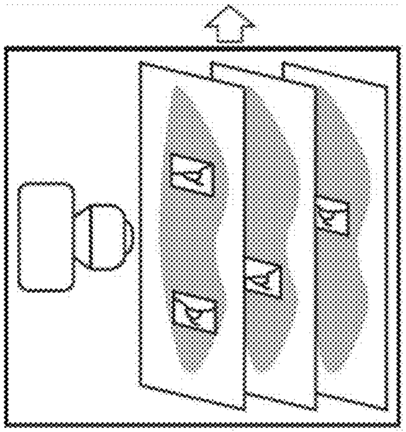
Figure 3F:
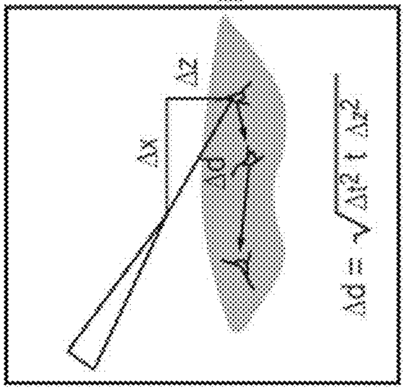
Figure 3G:
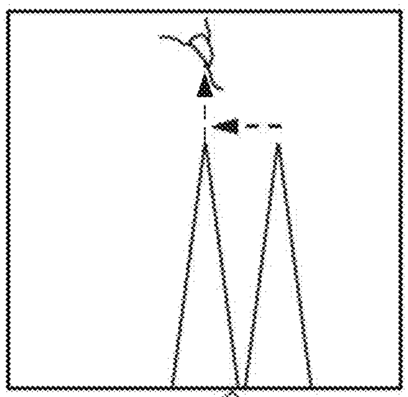

FIGS. 3D-3G show another example autoinjection process according to techniques of this disclosure. FIG. 3D shows calibration of micromanipulator 114 determines the location of the tip of micropipette 118 in 3D space by relating its coordinate system to the coordinate systems of microscope camera 110 and focus controller 108. FIG. 3E shows computer vision cell detection that automatically scans axially through tissue sample 122, detects cells via a computer vision algorithm or machine learned neural network, determines coordinates of the cells in 3D space, and selects cells for injection. FIG. 3F represents optimal path planning that finds the quickest path between cells and a micromanipulator trajectory is generated to attempt microinjection on the selected cells. FIG. 3G shows that during microinjection, a Kalman filter is used to estimate the position of the tip of micropipette 118 and corrects for 2D (x and y) positioning inaccuracies. In other examples, a machine learned model (e.g., a YOLO model) may be used for estimating a 3D position of the tip of micropipette 118.

Figure 4:
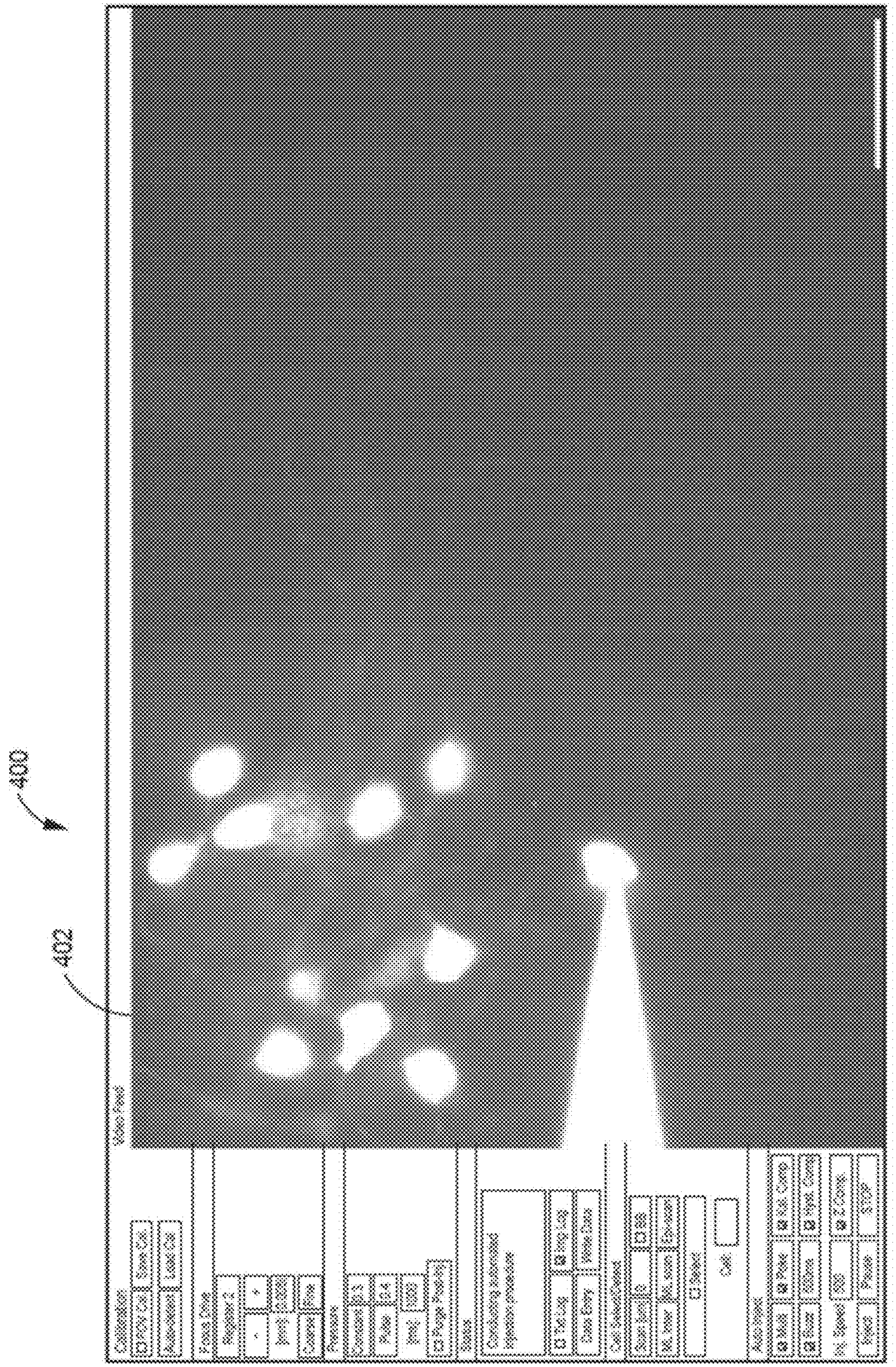
FIG. 4 is a screen illustration of an example user interface for user control of the robotic microinjection system according to techniques of this disclosure.

FIG. 4 is a screen illustration of an example user interface 400 for user control of the robotic microinjection system according to techniques of this disclosure. A user may control robotic microinjection system 100 through a custom-programmed graphical user interface (GUI) 400. GUI 400 includes a window 402 to display a live video feed from microscope camera 110 for providing visual feedback. The image shown in FIG. 4 shows injection of Striatal cells with an Alexa Fluor 647 conjugated dextran injection solution. The left side of GUI 400 shows the various buttons that control the injection and calibration procedures. The scale bar for window 402 is 50 μm.

Through window 402 of GUI 400, the user can also interact with micromanipulator 114 by selecting micromanipulator calibration points as well as manually annotating cells for injection. GUI 400 also provides various buttons and entry boxes that allow the user to control the calibration and injection procedures. For instance, some of these buttons and entry boxes can create a new calibration, load a previous calibration, change the injection pressure, change the focal plane, modify the injection approach, automatically detect/select cells, and turn on/off the automatic positioning correction.

Figure 5:
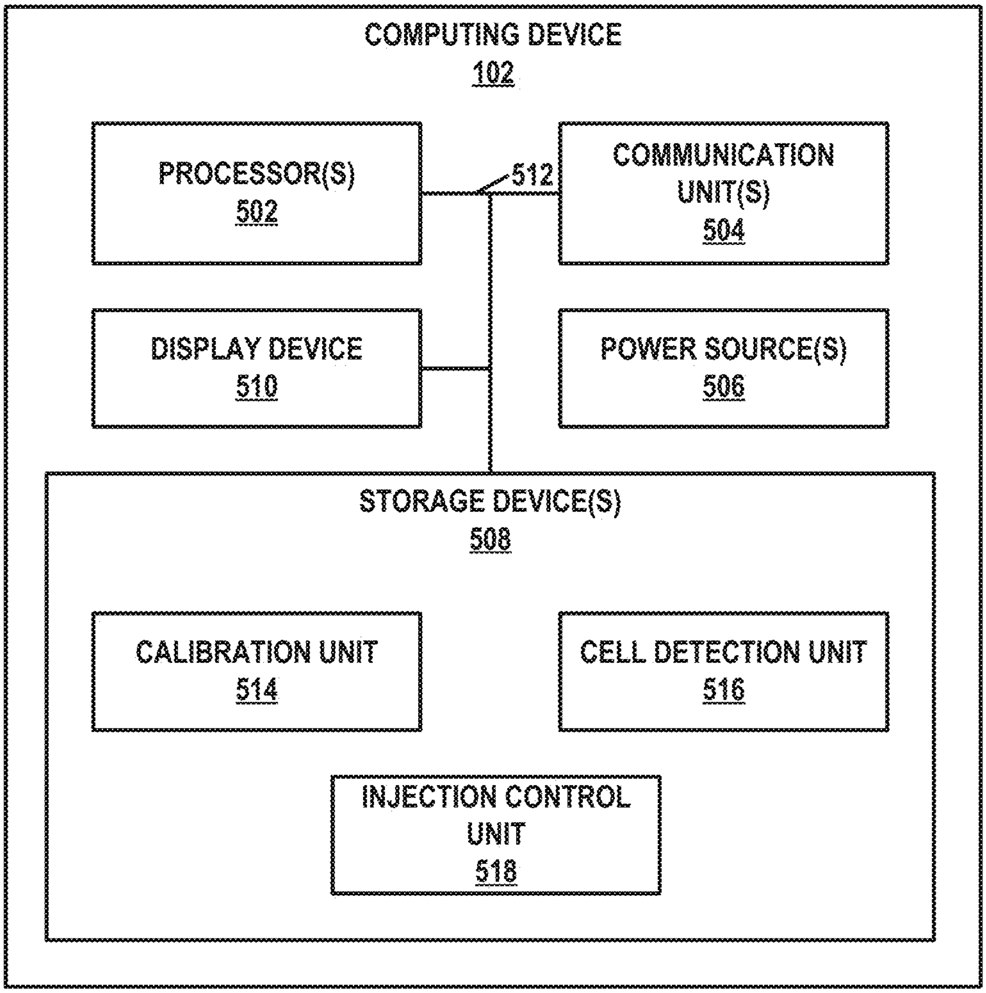
FIG. 5 is a block diagram illustrating example components of a computing device according to techniques of this disclosure.

FIG. 5 is a block diagram illustrating example components of computing device 102 according to techniques of this disclosure. FIG. 5 illustrates only one example of computing device 102, without limitation on any other example configurations of computing device 102. As shown in the example of FIG. 5, computing device 102 includes one or more processors 502, one or more communication units 504, one or more power sources 506, one or more storage devices 508, a display device 510, and one or more communication channels 512. Computing device 102 may include other components. For example, computing device 102 may include input devices, output devices, and so on. Communication channels 512 may interconnect each of processors 502, communication units 504, storage devices 508, and display device 510 for inter-component communications (physically, communicatively, and/or operatively). In some examples, communication channels 512 may include a system bus, a network connection, an inter-process communication data structure, or any other method for communicating data. Power sources 506 may provide electrical energy to processors 502, communication units 504, storage devices 508, storage devices 508, display device 510, and communication channels 512. Storage devices 508 may store information required for use during operation of computing device 102.

Processors 502 comprise circuitry configured to perform processing functions. For instance, one or more of processors 502 may be a microprocessor, an application-specific integrated circuit (ASIC), a field-programmable gate array (FPGA), or another type of processing circuitry. In some examples, processors 502 of computing device 102 may read and execute instructions stored by storage devices 508. Processors 502 may include fixed-function processors and/or programmable processors. Processors 502 may be included in a single device or distributed among multiple devices. In some examples, processors 502 may include one or more of an AMD Ryzen 9 3900×3.8 GHz, 64 MB DDR4-2400/2666 RAM, and a NVIDIA GeForce RTX 2080 Super.

Communication units 504 may enable computing device 102 to send data to and receive data from one or more other computing devices (e.g., via a communications network, such as a local area network or the Internet). In some examples, communication unit 504 may include wireless transmitters and receivers that enable computing device 102 to communicate wirelessly with other computing devices. Examples of communication units 504 may include network interface cards, Ethernet cards, optical transceivers, radio frequency transceivers, or other types of devices that are able to send and receive information. Other examples of such communication units may include BLUETOOTH™, 3G, 4G, 5G, and WI-FI™ radios, Universal Serial Bus (USB) interfaces, etc. Computing device 102 may use communication units 504 to communicate with one or more other computing devices or systems. Communication units 504 may be included in a single device or distributed among multiple devices.

Processors 502 may read instructions from storage devices 508 and may execute instructions stored by storage devices 508. Execution of the instructions by processors 502 may configure or cause computing device 102 to provide at least some of the functionality ascribed in this disclosure to computing device 102 or units stored in storage devices 508. Storage devices 508 may be included in a single device or distributed among multiple devices.

As shown in the example of FIG. 5, storage devices 508 may include computer-readable instructions associated with a calibration unit 514, a cell detection unit 516, and an injection control unit 518. The units shown in the example of FIG. 5 are presented for purposes of explanation and may not necessarily correspond to actual software units or modules. Calibration unit 514 is configured to perform calibration operations, such as operations to determine a position of micropipette 118 and microscope 112. Cell detection unit 516 is configured to detect positions of cells in images generated by microscope camera 110. Injection control unit 518 is configured to execute micropipette trajectories and perform barcoded cell injections.

As mentioned above, calibration unit 514 may perform calibration operations. In some examples, the calibration operation may use least squares regression to improve calibration accuracy. Least squares regression calibration is achieved by overdetermining the equations needed to construct a calibration function. As a result, the effect of any errors that may have altered the calibration (like pipette drift, FOV distortion, or imprecisely selected calibration points) is minimized. This approach contrasts with similar vision guided systems that use a calibration procedure that precisely defines the calibration function. Through the least squares regression calibration, calibration unit 514 may achieve better open-loop positioning performance in the absence of disturbances.

When attempting to inject cells, micromanipulator 114 must be accurately positioned in 3D space to inject cells of interest. Cell diameters range from 10 μm-20 μm, so the margin of error is small because even just 5 μm may be the difference between injecting the cell and displacing the cell. For example, imagine a balloon that is stuck to a wall by static electricity. If you poke at the balloon's center, the balloon will likely get stuck between your finger and the wall. However, if you poke the balloon off-center, then the balloon will likely just be displaced in some direction without getting pinched between your finger and the wall. The balloon behaves somewhat like cells in tissue. Tissue is a flexible matrix of cells, so the tissue has a tendency to displace when foreign objects like the micropipette are probing the tissue. Consequently, micropipette 118 must be accurately positioned near the cell's center to facilitate injection and prevent lateral displacements of the cell.

In an initial calibration step, micromanipulator 114, microscope camera 110, and focus controller 108 have unique, non-coincident coordinate systems. The coordinates of the injection point in 3D space correspond to the x-y pixel (camera) coordinates and the z focus drive coordinate of the user-selected or computer-vision selected cells. Therefore, calibration unit 514 may complete two calibrations to relate the pixel coordinates of microscope camera 110 to micromanipulator 114 (and vice versa) and the z coordinates of focus controller 108 to micromanipulator 114 (and vice versa).

Calibration unit 514 may complete the calibrations using the GUI (e.g., a GUI that calibration unit 514 outputs on display device 510) to view an image of the tip of micropipette 118 in the field of view (FOV). During x-y calibration, the user brings the micropipette tip into focus then indicates the tip of micropipette 118, e.g., by using the mouse to "click" the tip of micropipette 118. In other words, calibration unit 514 receives an indication of user input to indicate the tip of micropipette 118. In response to the indication of user input to indicate the tip of micropipette 118, calibration unit 514 saves the clicked pixel's coordinates and the position coordinates of micromanipulator 114. Calibration unit 514 may continue receiving indications of user input to select numerous points in the FOV and the calibration is computed as explained elsewhere in this disclosure. Calibration unit 514 may perform Z-calibration by bringing the tip of micropipette 118 into focus, registering the z-coordinate of micromanipulator 114 and focus controller 108, then moving micromanipulator 114 in the Z direction and refocusing on the tip of micropipette 118 and repeating for numerous points. Calibration unit 514 may then compute the calibration as described below.

Calibration unit 514 may achieve accurate x-y micromanipulator positioning by micromanipulator-to-camera calibration. The calibration may include (or, in some examples, consists of) constructing a homogenous transformation matrix via least squares regression to relate the coordinates of microscope camera 110 and coordinates of micromanipulator 114.

For a homogenous transformation matrix, how each axis in the first coordinate system (microscope camera 110 or micromanipulator 114) are rotated, scaled, and translated to coincide with the second coordinate system may be determined. The homogenous transformation matrix, $T_H$, is shown in Equation (1) and Equation (2), below. The transformation matrix converts the pixel coordinates, ($x_{cam}$, $y_{cam}$), of microscope camera 110 to the x-y coordinates, ($x_{man}$, $y_{man}$), of micromanipulator 114. These coordinates are related through a series of rotations/scaling, $\phi_{ij}$, and translations, $\delta$.

$$\begin{bmatrix} x_{man} \\ y_{man} \\ 1 \end{bmatrix} = T_H \begin{bmatrix} x_{cam} \\ y_{cam} \\ 1 \end{bmatrix} \tag{1}$$

$$T_H = \begin{bmatrix} \phi_{11} & \phi_{12} & \delta_x \\ \phi_{21} & \phi_{22} & \delta_y \\ 0 & 0 & 1 \end{bmatrix} \tag{2}$$

The exact values of the rotation, scaling, and translation are unknown, but their values can be approximated by relating micromanipulator 114 and microscope camera 110 coordinates at three distinct points in the FOV and solving a system of linear equations. As shown in Equation (1) and Equation (2) above, the x coordinate of micromanipulator 114 is related to x and y coordinates of microscope camera 110 through the first row in $T_H$. Likewise, the y coordinate of micromanipulator 114 is related to x and y coordinates of microscope camera 110 through the second row in $T_H$. This relationship is shown in Equation (3), below, for three non-singular and corresponding micromanipulator and camera coordinates in the FOV. Therefore, by selecting three non-singular points in the field of view, an invertible matrix, H, calibration unit 514 may solve for the values in the homogenous transformation matrix (Equation (4) and Equation (5)).

$$\begin{bmatrix} x_{man,1} & y_{man,1} \\ x_{man,2} & y_{man,2} \\ x_{man,3} & y_{man,3} \end{bmatrix} = \begin{bmatrix} x_{cam,1} & y_{cam,1} & 1 \\ x_{cam,2} & y_{cam,2} & 1 \\ x_{cam,3} & y_{cam,3} & 1 \end{bmatrix} \begin{bmatrix} \phi_{11} & \phi_{12} \\ \phi_{12} & \phi_{22} \\ \delta_x & \delta_y \end{bmatrix} \tag{3}$$

$$H = \begin{bmatrix} x_{cam,1} & y_{cam,1} & 1 \\ x_{cam,2} & y_{cam,2} & 1 \\ x_{cam,3} & y_{cam,3} & 1 \end{bmatrix} \tag{4}$$

$$\begin{bmatrix} \phi_{11} & \phi_{12} \\ \phi_{21} & \phi_{22} \\ \delta_x & \delta_y \end{bmatrix} = H^{-1} \begin{bmatrix} x_{man,1} & y_{man,1} \\ x_{man,2} & y_{man,2} \\ x_{man,3} & y_{man,3} \end{bmatrix} \tag{5}$$

Due to a number of factors like objective distortion, Petzval field curvature, pipette drift during calibration, and user error during tip selection, the three selected points for calibration may not accurately represent the transformation between the coordinate systems. Better accuracy can be achieved by overdetermining the calibration by selecting more than 3 calibration points and using least squares regression to fit the coordinate data to a homogenous transformation matrix. Using this method, any errors stemming from selected points that deviate slightly from micropipette 118 are averaged across the number of points selected so the overall effect on the calibration is minimized by the calibratoin unit 514.

By choosing more than three points in the FOV, Equation (3) is modified to Equation (6), below. Now, the H matrix from before is non-square and therefore no longer invertible, as shown in Equation (7). The problem of non-invertibility can be overcome by generating the left-generalized inverse of H as shown in Equation (8). With this generalized inverse, the entries of the transformation matrix can be solved as shown in Equation (9). Calibration unit 514 may use the generalized inverse to solve for the transformation matrix entries is equivalent to conducting non-weighted least squares regression.

$$\begin{bmatrix} x_{man,1} & y_{man,1} \\ x_{man,2} & y_{man,2} \\ \vdots & \vdots \\ x_{man,n} & y_{man,n} \end{bmatrix} = \begin{bmatrix} x_{cam,1} & y_{cam,1} & 1 \\ x_{cam,2} & y_{cam,2} & 1 \\ \vdots & \vdots & \vdots \\ x_{cam,n} & y_{cam,n} & 1 \end{bmatrix} \begin{bmatrix} \phi_{11} & \phi_{12} \\ \phi_{12} & \phi_{22} \\ \delta_x & \delta_y \end{bmatrix} \tag{6}$$

$$H = \begin{bmatrix} x_{cam,1} & y_{cam,1} & 1 \\ x_{cam,2} & y_{cam,2} & 1 \\ \vdots & \vdots & \vdots \\ x_{cam,n} & y_{cam,n} & 1 \end{bmatrix} \tag{7}$$

$$H^L = (H^T H)^{-1} H \tag{8}$$

$$\begin{bmatrix} \phi_{11} & \phi_{12} \\ \phi_{21} & \phi_{22} \\ \delta_x & \delta_y \end{bmatrix} = H^L \begin{bmatrix} x_{man,1} & y_{man,1} \\ x_{man,2} & y_{man,2} \\ \vdots & \vdots \\ x_{man,n} & y_{man,n} \end{bmatrix} \tag{9}$$

Similar to micromanipulator-to-camera calibration, calibration unit 514 may complete a calibration operation to relate the z coordinates of micromanipulator 114 to the z coordinates of the focus drive of microscope 112 to permit accurate positioning in 3D space. However, because this calibration is only one-dimensional, a simple linear regression between scalar values may be sufficient to describe the relationship between micromanipulator 114 and focus controller 108. The linear equation for the relationship between micromanipulator 114, $z_{man}$, and the focus drive, $z_{fd}$, is shown in Equation (10), below, where a is the scaling and b is the offset between the axes. This relationship can be redefined in matrix form for two non-singular points as shown in Equation (11). Therefore, for two non-singular points, H (Equation (12)) is invertible and calibration unit 514 may solve Equation (12) for the relationship between the two axes as shown in Equation (13).

$$z_{man} = a \times z_{fd} + b \tag{10}$$

$$\begin{bmatrix} z_{man,1} \\ z_{man,2} \end{bmatrix} = \begin{bmatrix} z_{fd,1} & 1 \\ z_{fd,2} & 1 \end{bmatrix} \begin{bmatrix} a \\ b \end{bmatrix} \tag{11}$$

$$H = \begin{bmatrix} z_{fd,1} & 1 \\ z_{fd,2} & 1 \end{bmatrix} \tag{12}$$

$$\begin{bmatrix} a \\ b \end{bmatrix} = H^{-1} \begin{bmatrix} z_{man,1} \\ z_{man,2} \end{bmatrix} \tag{13}$$

Like with the manipulator-to-camera calibration, numerous factors like pipette drift or improper focusing may reduce the z calibration accuracy if only the minimum required number of calibration points are used. Therefore, calibration unit 514 may use least squares regression again to average any imprecise calibration points. Using the same process as before by incorporating extra calibration points, computing the left generalized inverse of the H matrix, and using least squares regression is shown in Equation (14)-Equation (16).

$$\begin{bmatrix} z_{man,1} \\ z_{man,2} \\ \vdots \\ z_{man,n} \end{bmatrix} = \begin{bmatrix} z_{fd,1} & 1 \\ z_{fd,2} & 1 \\ \vdots & \vdots \\ z_{fd,n} & 1 \end{bmatrix} \begin{bmatrix} a \\ b \end{bmatrix} \tag{14}$$

$$H = \begin{bmatrix} z_{fd,1} & 1 \\ z_{fd,2} & 1 \\ \vdots & \vdots \\ z_{fd_n} & 1 \end{bmatrix} \tag{15}$$

$$\begin{bmatrix} a \\ b \end{bmatrix} = H^{L} \begin{bmatrix} z_{man,1} \\ z_{man,2} \\ \vdots \\ z_{man,n} \end{bmatrix} \tag{16}$$

During an injection trial, a variety of factors may cause micrometer-scale positioning errors that cause micropipette 118 to miss the target position resulting in a failed cellular injection. These factors may include systematic errors that effect the positioning calibration like imprecisely selected calibration points or optical aberrations like FOV distortion or Petzval field curvature which are not modeled in the calibration formula. Other systematic errors may include non-planar micromanipulator and FOV x-y coordinate planes which can result in a change in the micromanipulator z-height as it traverses across the FOV despite only changing the x/y coordinates. Additionally, accuracy is affected by pipette drift which can stem from both random and systematic sources like thermal gradients, improperly shielded air ducts, micromanipulator cable drag, cantilevered micromanipulator mounting, or over/under tightened head stage and pipette gasket clamping. Altogether, the accumulation of these effects can lead to positioning-related injection failures making strictly open-loop positioning control insufficient for high-throughput injections.

In some examples, computing device 102 outputs a GUI for display. The GUI has a feature that allows the user to save FOV calibrations which can be loaded with each new trial. This may prevent the user from needing to perform a new FOV calibration with each trial. However, micropipette 118 may experience drift over the course of an experimental session from factors like thermal expansion and relaxation in the electrode holder and inherent drift in the axes of micromanipulator 114. Over time, the drift may accrue enough to affect the success of injection attempts which would incentivize the user to re-calibrate micromanipulator 114 to improve the success rate. In relation to the calibration (transformation matrix), the drift is merely changing the translation between the coordinate system of microscope camera 110 and the coordinates system of micromanipulator 114; it does not affect how these coordinate systems are rotated or scaled relative to each other. Consequently, calibration unit 514 may address the issue of compensating for the drift by finding the new translation between the coordinate systems. This may be accomplished by selecting a single point in the FOV corresponding to the current location of the pipette tip. In other words, calibration unit 514 may receive an indication of user input to indicate the current location of the tip of micropipette 118. From the linear equations in Equation (1) and Equation (2), the translations, $\delta_x$ and $\delta_y$, can be related to the selected points as shown in Equation (17) and Equation (18). Therefore, it can be seen that with a single point, the updated translation values can be solved to compensate the pipette drift. This method of updating the calibration may be substantially faster than a full calibration because the user must only select 1 point as opposed to 3 or more points.

$$x_{man} = \phi_{11} x_{cam} + \phi_{12} y_{cam} + \delta_x \tag{17}$$

$$y_{man} = \phi_{21} x_{cam} + \phi_{22} y_{cam} + \delta_y \tag{18}$$

Despite using least squares regression to improve the accuracy of the micromanipulator positioning in the FOV, numerous disturbances may lead to inaccurate or inconsistent positioning. One such disturbance is the hysteresis-like movement of micromanipulator 114. It is observed that displacements in one direction of the x and d (depth) axes of micromanipulator 114 cause unintended displacements (0.5-2 μm) in the y axis in a certain direction and displacements in the opposite direction in the x and d axes may cause unintended displacements in the other direction in the y axis. For instance, moving "forward" in x axis causes a 1 μm displacement "upwards" in the y axis while moving "backward" in the x axis causes a 1 μm displacement "downwards" in the y axis. These unintended displacements in the y-axis are large enough to cause failed injections, especially in smaller diameter cells.

To overcome this issue of coupled-axis displacement, calibration unit 514 may implement hysteresis compensation. Hysteresis compensation may include (or, in some examples, consist of) making the final approach to a desired position along the same directions in all axes as shown in a representative trajectory in Table 1, below. This may eliminate the aforementioned issue by making sure the unintended displacements from coupled axis displacements always occur in a predictable direction which can easily be corrected. Moreover, if the calibration points are all selected for points that have been hysteresis compensated, then the compensation is built into the calibration matrix and further correction is not needed.

TABLE 1

Comparison of naïve trajectory to hysteresis compensated trajectory. The hysteresis compensated trajectory approaches each final position in a positive direction (emphasized with * marks) to cause predictable out-of-axis displacements that can be corrected. All negative moves are marginally larger to adjust for the final approach to a position in a positive direction.

| Naïve Trajectory | | Hysteresis Compensated Trajectory | |
|---|---|---|---|
| Axis | Movement | Axis | Movement |
| Z | −11 | Z | −16 |
| X | −60 | Z | +5* |
| Y | +23 | X | −65 |
| D | +140 | X | +5* |
| D | −140 | Y | +23 |
| Y | −23 | D | +140 |
| X | +60 | D | −145 |
| Z | +11 | D | +5* |
| | | Y | −28 |
| | | Y | +5* |
| | | X | +60 |
| | | Z | +11 |

Micropipette drift, especially along the y-axis of micromanipulator 114 may cause a significant proportion of positioning related injection failures in our system. Relative to the FOV calibration, pipette drift is merely a translating of the micromanipulator coordinate system with respect to the camera and focus drive coordinate systems; it does not affect the relative rotations and scaling between the coordinate systems. Consequently, the GUI permits the user to conduct mid-trial calibration updates wherein the user can quickly re-coincide the coordinate systems to improve the positioning accuracy.

Figure 6A:
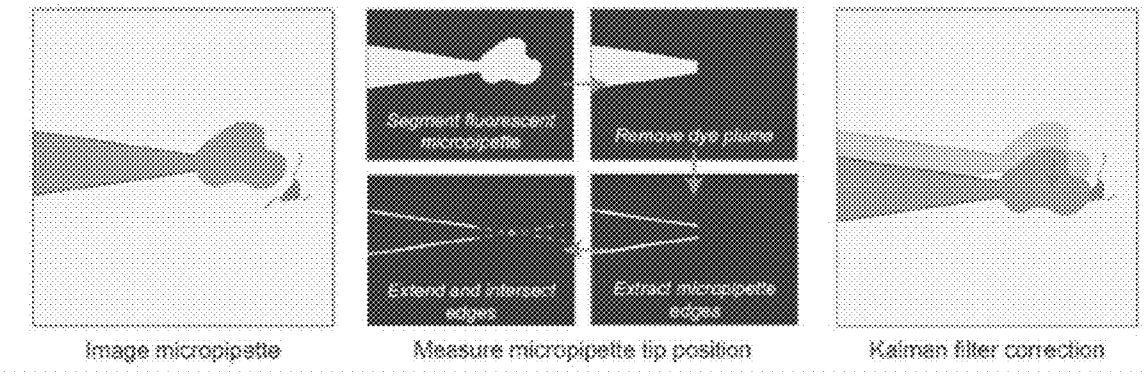
FIGS. 6A-6F show an example micropipette tip detection algorithm and Kalman filter estimation for micropipette positioning error correction according to techniques of this disclosure.
Figure 6B:
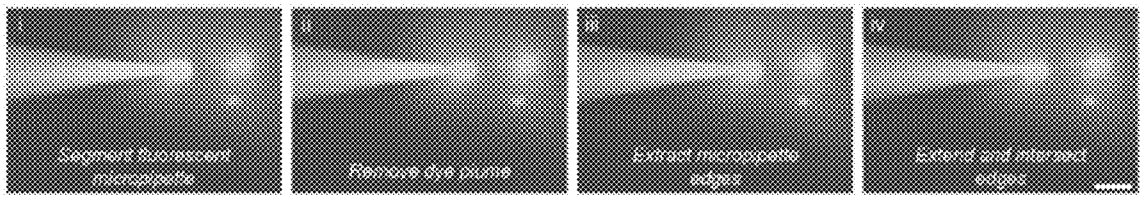

In addition to manual calibration updates, a computer vision algorithm was devised to compensate for micromanipulator positioning inaccuracies and remove some burden from the user. FIG. 6A represents this computer vision algorithm. By using the triangular shape of the pipette shank and tip, calibration unit 514 may extrapolate the edges of the pipette shank and may use the intersection of those edges as the measured tip position, e.g., as shown in FIG. 6B. Calibration unit 514 may operate on epifluorescent images of micropipette 118 filled with a fluorescent dye, and despite the plume of dye around the tip from constant pipette back pressure, injection control unit 518 may make estimates of the tip position.

Figure 6C:
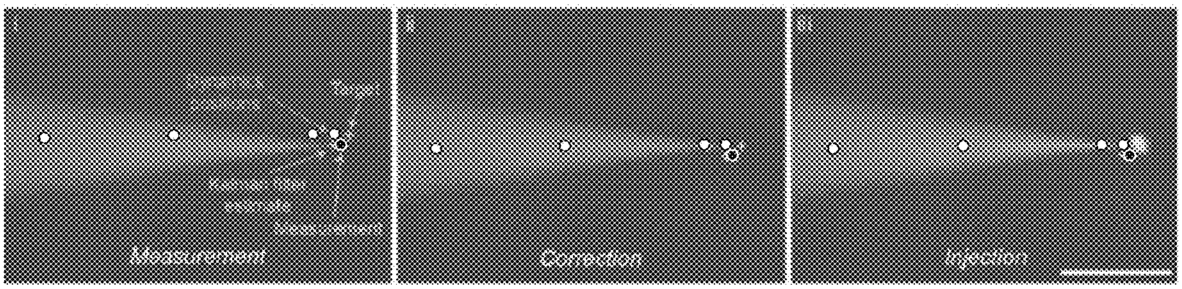

The accuracy of the micropipette tip detection may be improved by fusing information from the computer vision algorithm tip measurements with the dynamics of micromanipulator 114 in a Kalman Filter. In other words, following the micropipette tip location measurement, this measurement is fused with the dynamical information of the micromanipulator's position in a Kalman filter (KF) to generate an optimal estimate of the true micropipette's position in 2D (x and y) space. With the Kalman Filter, not only can calibration unit 514 automatically update the x-y calibration of micromanipulator 114, but calibration unit 514 can also make minor adjustments along the injection trajectory to compensate for minor inaccuracies near the injection location. In other words, with the KF estimate of the micropipette tip location, calibration unit 514 may correct trajectory misalignments/inaccuracies in the x and y axes to better align micropipette 118 with the target cell and facilitate injection (e.g., as shown in FIG. 6C). This KF approach of fusing measurement and dynamical information contrasts with other pipette localization algorithms that use purely measurement-based information to estimate the micropipette tip location.

Figure 6D:
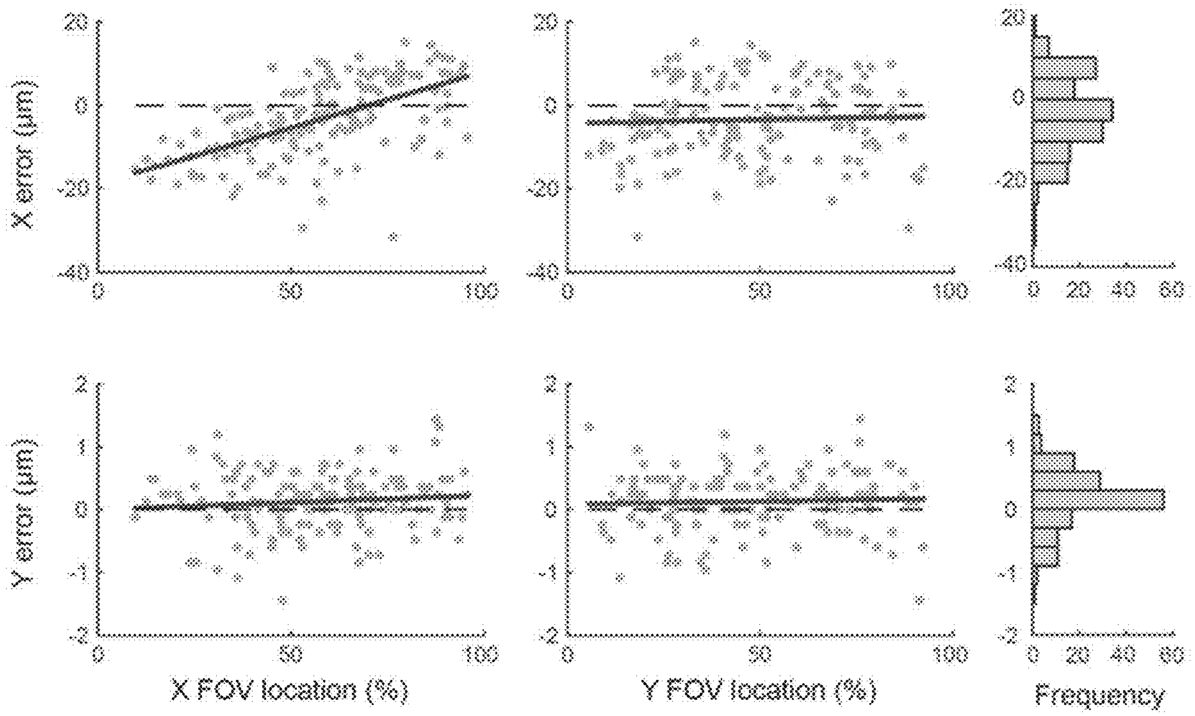

Because the micropipette tip measurement algorithm intersects the edges of micropipette 118 (i.e., extends the detected edges of micropipette 118 until the edge intersect as shown in FIG. 6A), the axial symmetry of the micropipette leads to a measurement of the tip position that is relatively more accurate for the micropipette's lateral (y) position than it is for the micropipette's axial (x) position (e.g., as shown in FIG. 6D). The symmetry causes the edge intersection to lie near the axial centerline of micropipette 118 regardless of micropipette 118 being in-focus or largely visible in the FOV. On the other hand, moving micropipette 118 out-of-focus changes the perceived axial intersection of the micropipette edges. Likewise, obscuring the part of the micropipette shank by moving it out of the FOV reduces the available edge information and reduces the accuracy of the axial positioning measurement.

An example algorithm for micropipette tip localization uses relatively simple thresholding and morphological operations to generate a measurement of the micropipette tip. First an epifluorescent microscopy image is obtained of a micropipette filled with a fluorescent dye (10,000 MW Dextran AlexaFluor 647), and a gaussian blur operation removes noise artifacts. Next, adaptive thresholding is used to inversely threshold and segment the background, morphological closing is applied to fill-in any gaps in the thresholded background, and finally the thresholded background region is inverted to segment the micropipette. Better results may be obtained during algorithm tuning when segmenting the background and inverting the background for the micropipette than when trying to directly segment micropipette 118. After the fluorescent micropipette and plume are segmented, the next step is to remove the plume so only the micropipette shank is segmented. This may be accomplished by advancing axially along the micropipette shank in uniform increments and computing the segmented area of each increment. As the algorithm advances along the shank, each area increment should decrease in size until it reaches the plume which will cause the subsequent area increment to increase in size. This area increase marks the point at which all following segmented areas should be removed resulting in only the shank to be segmented. Next, the morphological gradient operator is applied to extract the edges of the segmented area corresponding to the micropipette shank. Finally, lines are fit to the segmented edges via least squares and their intersection point is accepted as the micropipette tip measurement.

The computer vision algorithm's tip location measurements were characterized by analyzing data that was acquired throughout the development of the robotic system. During robotic system development, we saved images of the micropipette attempting to inject cells during experimental trials. As a result, we had a vast repository of epifluorescent images of fluorescent micropipettes in tissue attempting to inject cells. A sample of these images (N=152 images) were manually annotated for the perceived tip position coordinates as the 'ground truth' position. The measurement algorithm was then applied to the same images and the tip position coordinates were measured and recorded. Error was computed as the difference between the manually annotated 'ground truth' positions and the measured positions. The resulting error data is displayed in FIG. 6D. Because the 'ground truth' positions were manually annotated by a single user, there is certainly some variability in the actual ground truth locations, but we believe the annotations are close enough to illuminate the trends in measurement accuracy and variability.

A stochastic Kalman filter fuses information from a system's dynamical information (from a model) with a system's measurement information to generate an optimal estimate of the parameter of interest. The stochastic Kalman filter uses the statistics of the dynamic process noise and the measurement noise to compute an optimal weighting between the dynamics and the measurement when generating an estimate. Consequently, the noisiness and accuracy of dynamics and the measurements effect the precision of the KF. In this robotic system, the noise of the dynamics (robotics) is relatively consistent; however, the accuracy of the measurements is a function of the location within the FOV (FIG. 6D). This data is validated by intuition of the measurement algorithm. Since the measurement algorithm extrapolates the edges of the micropipette shank, if part of micropipette 118 is obscured by the top or bottom of the FOV, or the only a small portion of micropipette 118 is visible then the algorithm may struggle to extrapolate the edges and make a measurement. Therefore, the algorithm may be limited to only making measurements when micropipette 118 is away from the edges of the FOV (13%<x<93% and 10%<y<90%).

The KF works by initially using the dynamics of the robot (its FOV position from the calibration) as the position of the micropipette (a priori tip estimate). As explained before, this position may not coincide with the true tip position for a variety of reasons like imprecise calibration or micropipette drift. Therefore, the tip position estimation is improved by taking a measurement of the tip position, using the KF to generate an optimal weighting between the dynamics (calibration) position and the measurement position, and finally using that weighting to determine how much to "trust" the measurement to modify the a priori tip estimate in generating a new tip location estimate (a posteriori tip estimate). This a posteriori tip estimate is deemed the best estimate of the micropipette tip location and all corrections are made with respect to this position. If the a posteriori tip estimate exceeds a user defined positioning error threshold then the system moves the micropipette to realign with the target position. This process is shown in FIG. 6C.

Because the system is limited to only making tip position estimates away from edges of the FOV, the system may be attempting injections on cells near the FOV periphery with positioning errors exceeding the error threshold. Only once attempting injections on cells away from the FOV edges does the system have a chance to make a measurement and correct for the positioning errors. Consequently, some cells in an experimental trial near the FOV periphery may result in failed injections because the KF cannot correct for positioning errors at these cells.

Figure 6E:
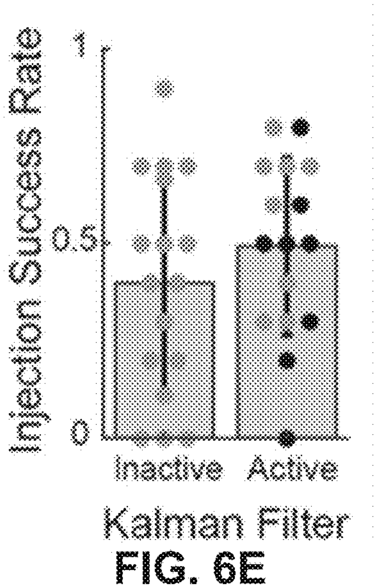
Figure 6F:
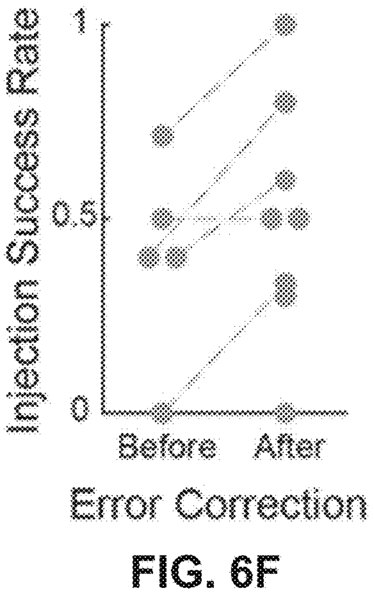

Despite the axial measurement inaccuracies, the fusion of the tip measurement and dynamical information in the KF generates an accurate measurement of the micropipette tip and can enable successful trajectory correction. In FIG. 6C, a cross denoting the KF estimate of the tip accurately coincides with tip position even though the circle denoting the measurement is axially offset from the tip. With the KF estimate, robotic microinjection system 100 can correct the trajectory and conduct a successful injection. Moreover, as shown in FIG. 6E, the average success rate for trials with positioning correction enabled were slightly higher than trials without positioning correction (49.4% versus 39.9%, respectively). Of those trials with a positioning correction, the success rate after the positioning correction tended to improve when compared to the success rate prior to the correction as shown in FIG. 6F. After a positioning correction, the success rate increased an average of 24.4%.

With the implementation of the computer vision tip detection algorithm and Kalman filter tip position estimation, we have increased the accuracy of targeted microinjection. As a result, we have enabled higher yield injections that will result in a larger proportion of the tissue containing positively injected cells which is beneficial for later transcriptomic analysis. Even though this algorithm was developed for microinjection, it could be applied to other tasks requiring highly precise positioning like dendritic patching. Moreover, the principles of combining micropipette tip location measurements with the typically available dynamical information of the micropipette could be incorporated with the other measurement algorithms to potentially improve their localization accuracy.

To summarize, FIGS. 6A-6F show an example micropipette tip detection algorithm and Kalman filter estimation for micropipette positioning error correction according to techniques of this disclosure. FIG. 6A shows a schematic overview of micropipette tip detection and Kalman filter positioning correction. First, micropipette 118 is imaged near the target cell. The tip detection algorithm segments the fluorescent signature of a micropipette filled with a fluorescently labeled dye and then it removes the dye plume surrounding the tip (if present). Next the algorithm extracts the edges of micropipette and uses least squares regression to fit lines to the edges of the micropipette. The intersection of these lines is taken as the measurement of the tip location. Finally, this measurement is fused with the dynamical information of the micropipette's position to generate an optimal estimate of the micropipette position in 2D (x and y) space. This position estimate is used to correct the micropipette trajectory to align with the target cell. FIG. 6B is a representation of the micropipette measurement algorithm. Shown in parts i-iv of FIG. 6B are fluorescent micropipette segmentation, dye plume removal, micropipette edge extraction, and micropipette edge extrapolation and intersection for tip detection. Scale bar is 50 μm. FIG. 6C provides a representation of the Kalman filter positioning correction. In part i of FIG. 6C, the micropipette's tip position is measured and a Kalman filter position estimate is generated. The cross denotes the target position, the white-filled circles denote the dynamical positions (the path the micropipette should be following), the black-filled circles denote the measured position, and the cross denotes the Kalman filter estimated position (fusing the dynamical position and measurement position). After the measurement, the micropipette trajectory is corrected and re-aligned with the target position as shown in ii of FIG. 6C. Finally, the micropipette injects the target cell along the corrected trajectory as shown in part iii of FIG. 6C. Scale bar is 50 μm. FIG. 6D represents measurement accuracy for the micropipette's x and y coordinates as a function of position within the field of view. The solid line shows least squares regression. The dashed line shows the zero-error line. Histograms depict the frequency of measurement errors. FIG. 6E shows inter-trial success rate between trials with and without Kalman filter positioning correction for errors greater than 2 μm. Only trials denoted with a black dot had a positioning correction. All other trials with active Kalman filter positioning correction had errors less than 2 μm, so no corrections were applied. FIG. 6F shows intra-trial success rates for trials with positioning error correction events. A correction event corrects the trajectory for that cell and for all cells that follow, so accuracy improves for all cells following a correction event. Some cells do not have a corresponding 'Before' error correction data point because the trajectory was corrected on the first cell of that trial.

In this way, injection control unit 518 may segment a shank of micropipette 118 in an image, fit lines to segmented shank of micropipette 118, extrapolate and intersect the lines to measure an (x, y) position of a tip of micropipette 118, and apply a Kalman filter to the (x, y) position of the tip of the micropipette 118. As part of controlling the robotic manipulator apparatus (e.g., micromanipulator 114) to insert micropipette 118 into a cell, injection control unit 518 may attempt injection of the cell based on the (x, y) position of the tip of micropipette 118.

As mentioned above, cell detection unit 516 is configured to detect positions of cells in images generated by microscope camera 110. In some examples, cell detection unit 516 may perform an automated, computer vision enabled cell detection and selection process for high-throughput target acquisition. Robotic microinjection system 100 may allow a user to manually z-scan through tissue sample 122 and annotate individual cells for microinjection. While this approach may be acceptable for low-throughput experiments like patch-clamping, it is not viable for large scale experiments where tens of cells are to be targeted for injection in a single FOV. Considering that microinjection needs to scale up to targeting hundreds of cells per tissue slice for high throughput tagging, it may be advantageous to automate the 3D cell detection process. Cell detection unit 516 may accomplish automation of the 3D cell detection process using a computer vision algorithm that detects cells of interest expressing a fluorescent protein.

There are two main aspects to the automated cell detection procedure: identifying the cells' locations in 3D space and determining each cell's viability for injection. It is important to identify the cells' locations so that micromanipulator 114 can accurately target the cells for microinjection using the aforementioned calibration. Likewise, determining each cell's viability is important because a single FOV may contain tens to hundreds of cells of interest, so it may be important to determine which cells should be prioritized for injection to maximize the injection success rate.

A plethora of algorithms have been developed to detect fluorescent cells in tissue. A number of these algorithms have aspects that overlap with techniques used by cell detection unit 516 to define the x, y, and z coordinates of cells in 3D space. Accordingly, cell detection unit 516 may use techniques based on features from numerous algorithms. For x-y coordinate determination, cell detection unit 516 may apply a workflow similar to N. Harder, F. Mora-Bermúdez, W. J. Godinez, J. Ellenberg, R. Eils, and K. Rohr, "Automated Analysis of the Mitotic Phases of Human Cells in 3D Fluorescence Microscopy Image Sequences," in Medical Image Computing and Computer-Assisted Intervention—MICCAI 2006, Berlin, Heidelberg, 2006, pp. 840-848. doi: 10.1007/11866565_103 (hereinafter, "Harder"), whose cell segmentation task aligns with the functions of cell detection unit 516 of determining the x-y coordinates for fluorescent cells in tissue. In Harder, fluorescent mitotic cells are imaged in a 3D image stack using a maximum intensity projection which is followed by threshold-based cell segmentation. However, in addition to using a maximum intensity projection (MIP) and threshold-based segmentation, cell detection unit 516 may also perform a preprocessing/contrast enhancement step to improve dim cell visibility, a common procedure prior to segmentation used in other algorithms.

For z-coordinate determination, cell detection unit 516 may perform a process based on the autofocus techniques of H.-J. Suk, I. van Welie, S. B. Kodandaramaiah, B. Allen, C. R. Forest, and E. S. Boyden, "Closed-Loop Real-Time Imaging Enables Fully Automated Cell-Targeted Patch-Clamp Neural Recording In Vivo," Neuron, vol. 95, no. 5, pp. 1037-1047.e11, August 2017, doi: 10.1016/j.neuron.2017.08.011 and shape-from-focus applications that uses a focus operator to indicate the most "in-focus" z depth to use as the z-coordinate for the detected cells.

Figure 7A:
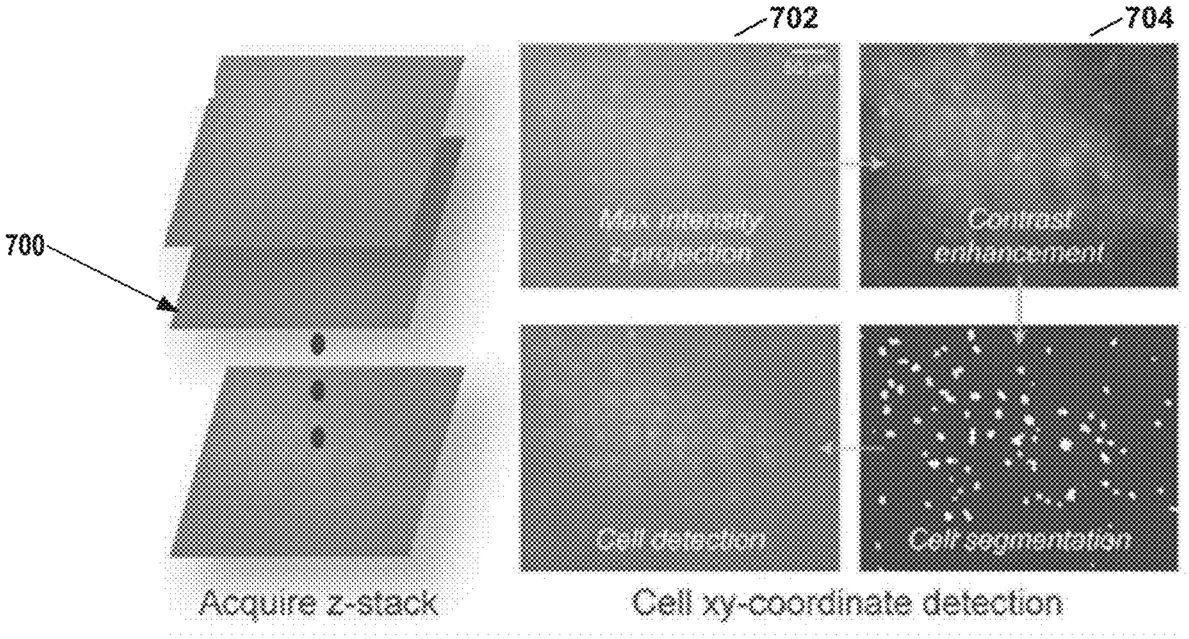
FIGS. 7A-7J are conceptual diagrams illustrating an example computer vision process for cell location identification according to techniques of this disclosure.
Figure 7B:
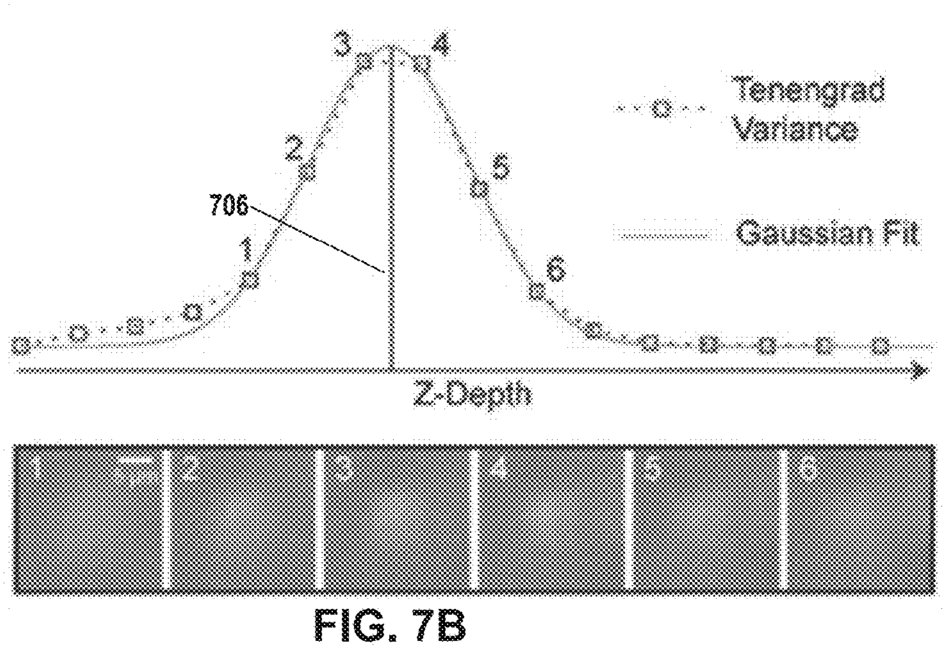
Figure 7C:
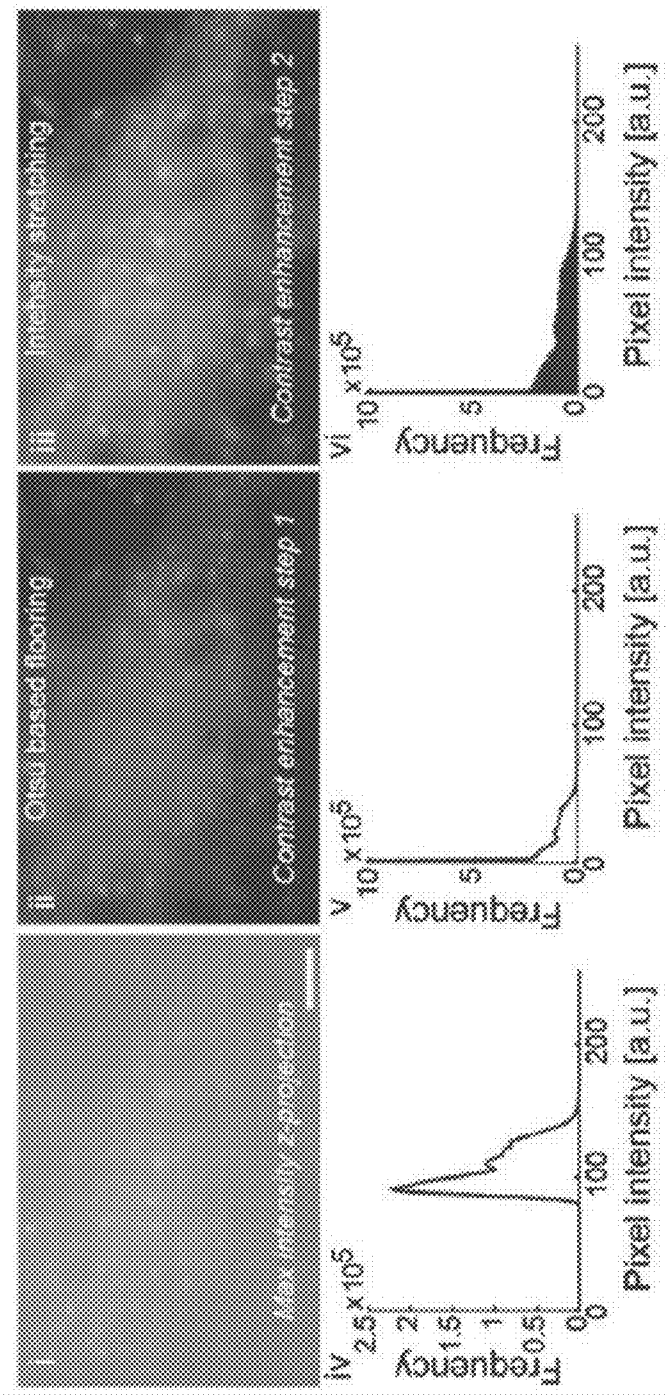
Figure 7D:
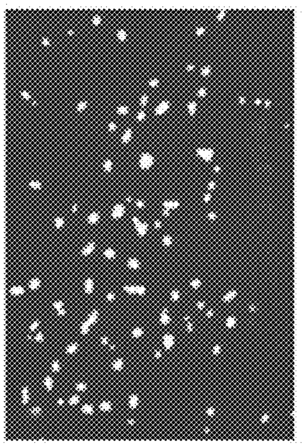

An overview of the computer vision algorithm for cell location identification is shown in FIGS. 7A-7J. In other words, FIGS. 7A-7J are conceptual diagrams illustrating an example computer vision process for cell location identification according to techniques of this disclosure. Specifically, FIG. 7A shows an overview of cell location identification. A z-stack 700 is acquired that encompasses the tissue volume of interest. In other words, the system automatically scans through a user defined volume of tissue while taking images to generate a z-stack. Cell detection unit 516 compresses Z-stack 700 into a single maximum intensity projection (MIP) 702 and enhances the MIP contrast 704. Cell detection unit 516 then determines the X and Y coordinates of cells by segmenting the MIP via thresholding and computing the centroids of the segmented cells. As shown in FIG. 7B, cell detection unit 516 determines the z coordinate of a cell by computing the Tenengrad variance (dashed line) for each z-stack image of each cell and fitting a gaussian distribution to the data (upper solid line). An optimum z coordinate is chosen as the mean 706 of the fitted distribution (lower solid line). Each labeled Tenengrad variance value (1-6) corresponds to the similarly labeled image of the cell as it comes in and out of focus. FIG. 7C shows steps for contrast enhancement and the associated image histogram. Otsu-based flooring eliminates regions of the image that are mostly devoid of cells and intensity stretching improves the visibility of the cells of interest. This may be accomplished by reducing all pixel intensities by a threshold computed via Otsu's method thereby shifting the image histogram towards zero. Intensity stretching improves the visibility of the cells of interest by linearly stretching the Otsu floored histogram to fill the full intensity range. Scale bar is 50 μm. FIG. 7D shows threshold-based segmentation of the contrast enhanced MIP.

Figure 7E:
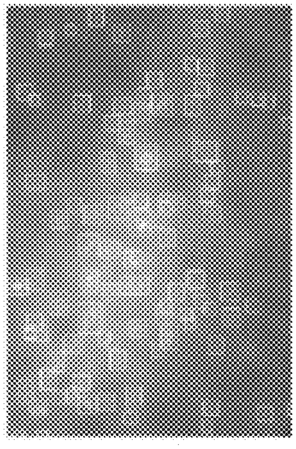

FIG. 7E shows detected cells bounded in boxes and their centroids (dots). Cells in the contrast enhanced MIP are segmented via adaptive thresholding, and the detected cells (boxes) are positionally defined by the (x,y) coordinates of their centroids (dots).

Figure 7F:
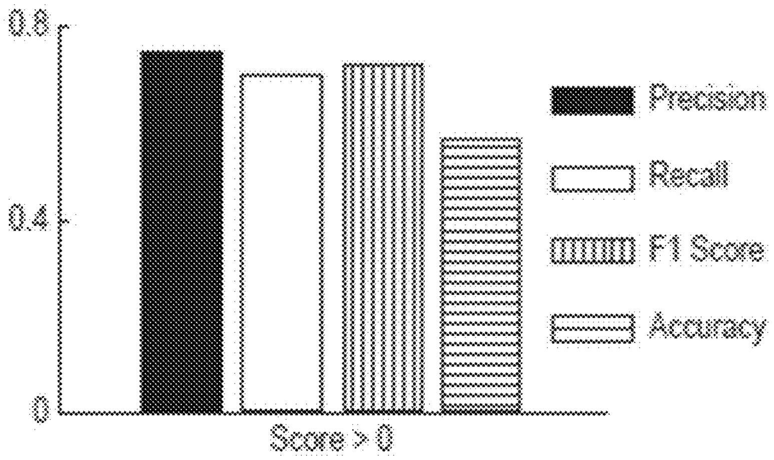
Figure 7G:
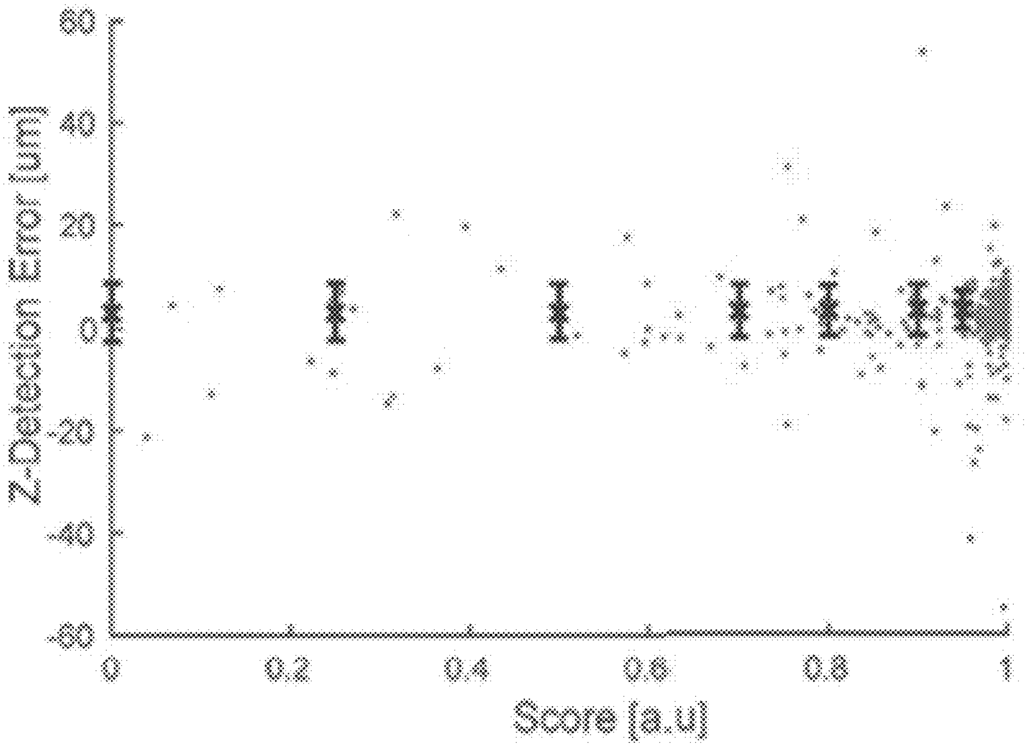
Figure 7H:
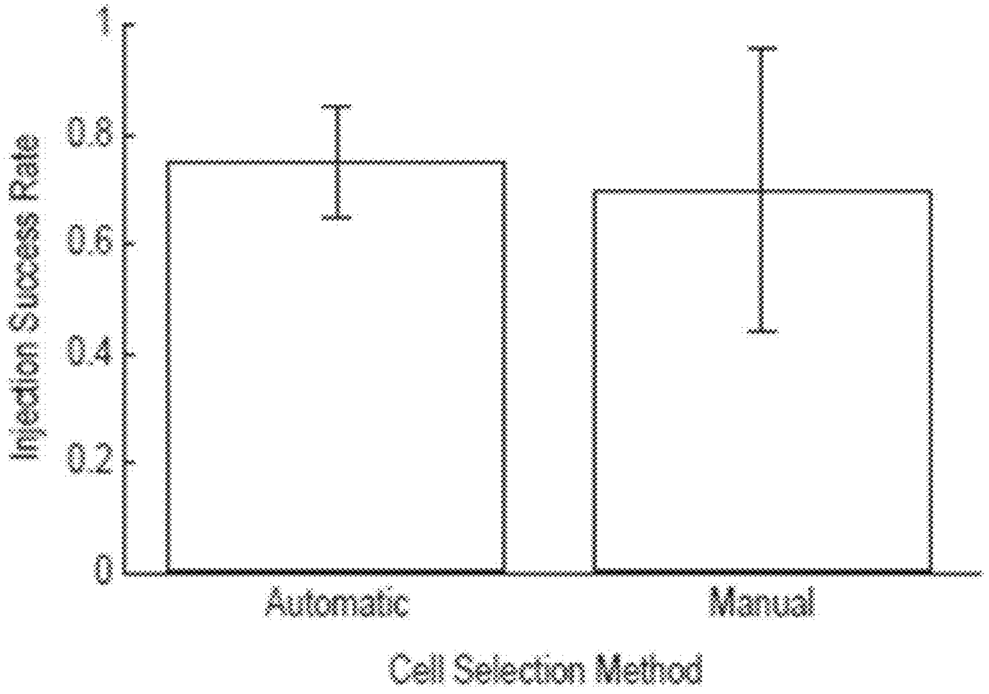

FIG. 7F shows example performance of cell detection. FIG. 7G shows example performance of z coordinate determination. In FIG. 7G, dots represent individual cells while crosses and error bars represent the mean and one standard deviation for all data above that score value. FIG. 7H shows an example injection success rate comparison between automatic computer vision selected cells and manual user annotated cells. Error bar is one standard deviation.

Figure 7I:
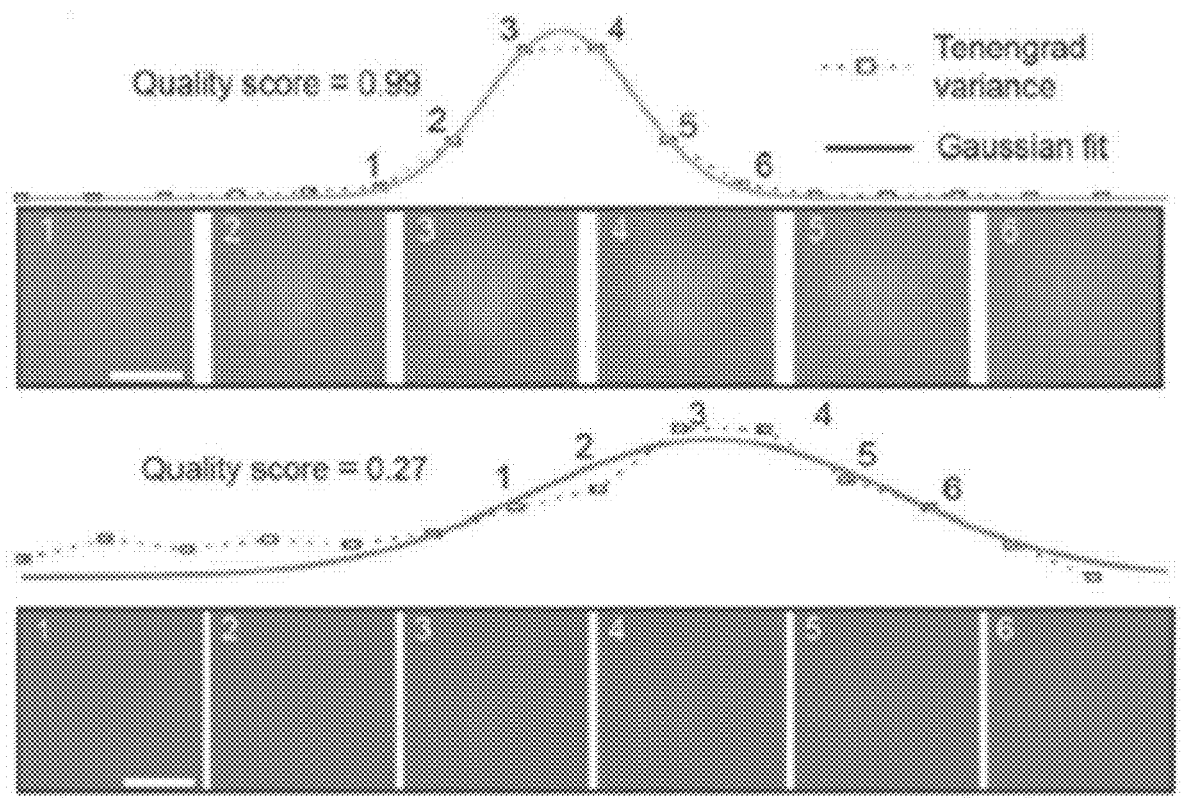

As mentioned above, cell detection unit 516 may automatically scan through a user-defined volume of tissue while taking images to generate z-stack 700. For x-y coordinate determination, cell detection unit 516 may compress z-stack 700 into a MIP, enhance the MIP contrast (e.g., by stretching the image histogram to fill the whole intensity range), and segment cells from the contrast-enhanced MIP using adaptive thresholding. Cell detection unit 516 may take the x-y coordinates of each cell to be the centroid of each segmented object. Steps for (x,y) coordinate determination are shown for a representative MIP in FIG. 7C to FIG. 7E. Following x-y coordinate determination, cell detection unit 516 may determine the z-coordinate by finding the most in-focus optical section for each cell. Cell detection unit 516 may accomplish this by computing a focus metric (e.g., the Tenengrad variance) for each z-stack image of each cell. Cell detection unit 516 may then fit a gaussian distribution to the computed Tenengrad variance and select the mean of the distribution as the optimum z-coordinate of each cell. Raw Tenengrad variance data, their fitted gaussian distributions, and images of cells near the detected (z) coordinate are shown in FIG. 7I. In FIG. 7I, representation of cell quality score and its relation to the focus metric data and fitted gaussian distribution. Numbers 1-6 relate the z-stack image to the labeled point in the focus metric data. Scale bars are 5 μm.

Figure 7J:
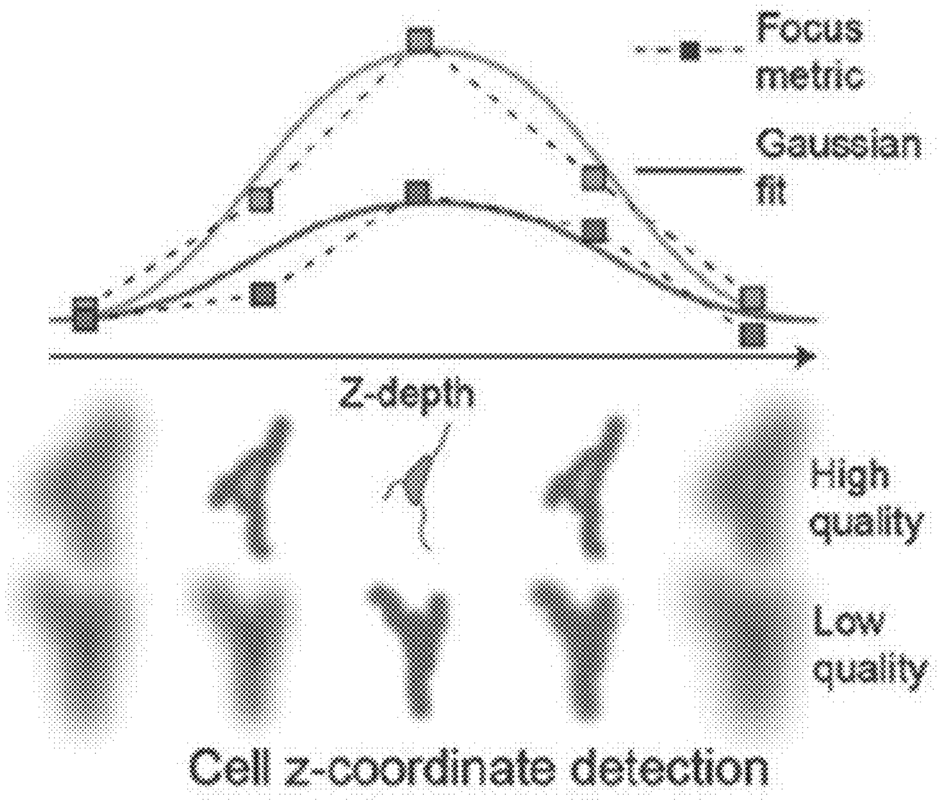

FIG. 7J is an alternative version of FIG. 7B. In the example of FIG. 7J, cell detection unit 516 determines Z coordinates by taking the mean value of a gaussian distribution that is fit to focus metric data for each of the cells' z-stacks. Cell detection unit 516 may determine cell quality by how well the fitted distribution relates to the raw focus metric data.

The performance of the computer vision algorithm to accurately identify and locate cells at an intersection-over-union (IoU) of 0.4 is shown in FIG. 7F. Precision, recall, F1-score, and accuracy are common metrics for assessing the performance of convolutional neural networks at vision identification tasks, so they relevant in this application as well. As shown, precision, recall, F1-score, and accuracy are 74.6%, 70.3%, 72.4%, and 56.7% respectively. This algorithm performs similarly to other algorithms designed for cell detection. A watershed-based algorithm for detecting fluorescent cells in in-resin fluorescence sections with integrated light and electron microscopy achieved precision and recall scores of 63% and 67% at a dice score of 0.5. A number of machine learning algorithms were trained to detect cells in DIC achieved F1-scores of 80% (M. C. Yip, M. M. Gonzalez, C. R. Valenta, M. J. M. Rowan, and C. R. Forest, "Deep learning-based real-time detection of neurons in brain slices for in vitro physiology," Sci. Rep., vol. 11, no. 1, Art. no. 1, March 2021, doi: 10.1038/s41598-021-85695-4), 56.55% (K. Koos et al., "Automatic deep learning-driven label-free image-guided patch clamp system," Nat. Commun., vol. 12, no. 1, p. 936, February 2021, doi: 10.1038/s41467-021-21291-4, hereinafter, "Koos"), and 65.83% (Koos). FIG. 7G shows the accuracy of the z-coordinate detection when compared to manually annotated most in-focus optical sections. As shown, there is a 3.05-3.40 μm mean error between the automatically detected optimum z-coordinate and the manually annotated optimum z-coordinate. Despite this error, FIG. 7H shows that automatic cell selection performs similarly to manual cell selection on the basis of injection success rate, 75% versus 65% respectively.

With micromanipulator calibration, computer vision cell detection, and Kalman filtering position correction, robotic microinjection system 100 may achieve accurate targeting of single cells, but other factors can still affect the success rate of injections. An injection can only be successful if micropipette 118 can penetrate the cell membrane to deliver the injection solution intracellularly. The cell membrane is a tough and compliant boundary that deforms upon the application of mechanical force thereby increasing the difficulty of a successful penetration. Therefore, it is principal to explore what factors lead to successful micropipette penetration and subsequent injection.

Through the automation of robotic microinjection system 100, rapid and systematic parameter exploration may be conducted to determine how changing the injection parameters effected the injection success rate while using a fluorescent dextran injection solution. In some examples, three such parameters are explored which included the speed of injection, the depth of injection, and the application of an electrical pulse to disrupt the cell membrane. Speed was investigated because it was hypothesized that rapidly attempting to penetrate the cell membrane would reduce the amount of time that the membrane could absorb the impact which would lead to greater penetration success. Along a similar vein, depth was investigated because it is believed that attempting to inject deeper into the cell would create larger membrane deformations increasing the membrane tension and making the membrane more prone to penetration. Finally, the electrical pulse was investigated because it is occasionally used in patch-clamping to penetrate the cell, like electroporation. All three parameters were tested at low and high levels in a $2^3$ full factorial experiment. Success was defined as a visibly defined fluorescent soma boundary following an injection of the fluorescent dextran solution.

The automated robotic system and microinjection process optimization have enabled high-throughput injection into single cells, something that was previously unattainable because of laboriousness of manual microinjection. Through the implementation of automatic cell selection and an optimal path finding algorithm, robotic microinjection system 100 may achieve highly specified single cell injection rates of 118.1 cells per hour in striatum tissue and 70.6 cells per hour in spinal cord tissue.

Positioning error correction is accomplished by fusing information from a micropipette tip location measurement with the micromanipulator's dynamical information in a Kalman filter to generate an optimal estimate of the micropipettes true (x,y) position. The Kalman filter may therefore involve two things: a measurement system to generate measurements and a dynamical model from which the dynamical information is obtained. The following sections discuss these two aspects and how they are combined in the Kalman filter.

The raw image is first smoothed with a gaussian filter to reduce image noise. Next adaptive thresholding is used to segment for the background of the image. Finally, the largest region is selected as the background and this largest region is morphologically closed to fill in the gaps that are present from the adaptive thresholding.

A Kalman filter assumes the measurement and process noise are zero-mean white noise processes. As shown in FIG. 6D, the x position measurement error versus the x position in the FOV is not zero mean, in fact it changes across the FOV. Consequently, using the raw measurement data may lead to a poorly performing Kalman filter. To remedy this issue, calibration unit 514 may correct the measurement data by subtracting the least squares fit line to modify the incoming measurement data to be approximately zero mean. All other measurement data has errors that are close to 0 (or at least close enough based on the system's resolution and positioning capabilities) such that the measurements don't need to be corrected.

A goal in developing the positioning correction algorithm was to correct the trajectory/position of the micropipette right before it attempted injection on a cell. The approach of micropipette 118 to the cell or its movements when micropipette 118 was not attempting an injection are not of concern. As a result, a discrete time model for micromanipulator dynamics may be formulated that only explains the position of micromanipulator 114 after micromanipulator 114 has completed a move. The discrete time model does not account for the how micromanipulator 114 moves between positions. This is a valid approach because the approach of micromanipulator 114 to a cell is stepwise such that micropipette 118 starts somewhere above tissue sample 122, completes a move to align the diagonal axis with the cell, completes another move to advance micropipette 118 along the diagonal axis until micropipette 118 is abutting a cell, and completes a final move to attempt to penetrate the cell. The discrete time model does not model positions of micromanipulator 114 at the intermediate instances between moves. This may allow robotic microinjection system 100 to streamline the dynamical model by not needing to incorporate the velocity/acceleration profiles of micromanipulator 114. Moreover, when the dynamical model is implemented in the Kalman filter, it may be easier to use this discrete model formulation to tie in the measurement information without needing to account for the latency between the camera feed (and therefore the measurement) and the micromanipulator position.

The discrete model of the micromanipulator dynamics states is shown in Equation (19) and its simplified version in Equation (20), below. The states for the system are the (x,y) coordinates of the micropipette tip relative to the camera coordinate frame ($p_{x,c}$ and $p_{y,c}$), the (z) coordinate of the micropipette tip relative to the focus controller ($p_{z,f}$), and the (d) coordinate of the micromanipulator diagonal axis. These states are denoted in the simplified equation as x. The inputs into the system are the commanded change in the micromanipulator axes between the k and k+1 position denoted as $\delta_{x,c}$, $\delta_{y,c}$, $\delta_{z,f}$, and $\delta_d$. In the simplified equation, these inputs are denoted as u. The angle between the micromanipulators x and d axes is denoted as θ. Lastly, ω is the process noise which is unknown.

$$\begin{bmatrix} p_{x,c} \\ p_{y,c} \\ p_{z,f} \\ p_d \end{bmatrix}(k+1) = \begin{bmatrix} 1 & 0 & 0 & 0 \\ 0 & 1 & 0 & 0 \\ 0 & 0 & 1 & 0 \\ 0 & 0 & 0 & 1 \end{bmatrix} \begin{bmatrix} p_{x,c} \\ p_{y,c} \\ p_{z,f} \\ p_d \end{bmatrix}(k) + \begin{bmatrix} 1 & 0 & 0 & \cos(\theta) \\ 0 & 1 & 0 & 0 \\ 0 & 0 & 1 & \sin(\theta) \\ 0 & 0 & 0 & 1 \end{bmatrix} \begin{bmatrix} \delta_{x,c} \\ \delta_{y,c} \\ \delta_{z,f} \\ \delta_d \end{bmatrix}(k) \quad 19$$

$$x(k+1) = Ax(k) + Bu(k) + \omega(k) \quad 20$$

Likewise, the model for the measurement of the micromanipulator dynamics can be constructed as shown in Equation (21) and its simplified version in Equation (22). The measurement of the micromanipulator dynamics are only the (x,y) positions of micromanipulator 114 with respect to the camera frame ($p_{x,c}$ and $p_{y,c}$). These outputs are denoted as y in the simplified equation. The measurement noise, which is unknown, is denoted as v.

$$\begin{bmatrix} p_{x,c} \\ p_{y,c} \end{bmatrix}(k+1) = \begin{bmatrix} 1 & 0 & 0 & 0 \\ 0 & 1 & 0 & 0 \end{bmatrix} \begin{bmatrix} p_{x,c} \\ p_{y,c} \\ p_{z,f} \\ p_d \end{bmatrix}(k+1) + v(k+1) \quad 21$$

$$y(k+1) = Cx(k+1) + v(k+1) \quad 22$$

The measurement algorithm may not be capable of (z) coordinate measurement so only the (x,y) coordinates are used as an output. However, other examples may expand the measurement algorithm to acquire (z) coordinate measurements and the output equations may be accommodated to present this extra information.

Even though drift is a dominant factor causing positioning errors, the dynamics of the drift are not modeled here. The dynamics of the drift were omitted because exact knowledge of the drift is unknown. The system could be formulated in an attempt to measure the drift, but the potential inability to measure the z-axis coordinate leads to unobservable states—i.e., the z-axis can be drifting but robotic microinjection system 100 would not have data regarding the z-axis drift. During the potential unobservable z-axis drift, micropipette 118 is going out of focus which subsequently affects the measurements of the axial position of micropipette 118. As a result, the unobservable drift of the z-axis causes cross talk in the x axis measurement, but there may be no way in knowing whether the x-axis measurement is a correct or spurious from an out-of-focus shank. Therefore, before the drift dynamics can be modeled and measured, the measurement system may be expanded to taking measurements of the z-axis so there isn't error coupling between the z and x axis. D-axis drift is negligible, so even though its unobservable, it likely won't need to be modeled. Even without modeling the drift dynamics, we achieved respectable results. Moreover, the KF is restarted with every trial, so the initial stages of drift could still be analyzed as a random walk process consistent with white noise processes. Over the duration of a long trial this could be an issue, but short trials enable frequent resets of the Kalman filter. Moreover, drift is time dependent process, but the discrete model uses steps of micromanipulator movements (not steps of time), so one could not merely use uniform drift dynamics because the time between steps is not uniform.

The Kalman filter may include (or, in some examples consist of) two stages: an a priori update and an a posteriori update. The a priori update uses the dynamical information to generate a new estimate on the state and its covariance according to the Kalman filter equations in Equation (23) and Equation (24). The a priori estimate of the states are denoted as $\hat{x}^-$ and the a priori state estimation covariance is $P^-$. When the "–" superscript is omitted, this means the state estimate or the covariance estimate could be from an a priori or a posteriori update (depending on when a measurement is available). The process noise covariance is denoted as Q.

$$\hat{x}^-(k+1) = A\hat{x}(k) + Bu(k) \quad 23$$

$$P^-(k+1) = AP(k)A^T + Q \quad 24$$

Once a measurement is available, the a posteriori update occurs to fuse information from the measurement with current best estimate of the state (whether it is a priori or a posteriori information) as shown in Equation (25)-Equation (27). The "+" superscript denotes the a posteriori information (state or covariance). The measurement noise covariance is denoted as R.

$$K(k) = P(k)H^T\left(HP(k)H^T + R\right)^{-1} \quad 25$$

$$\hat{x}^+(k) = x(k) + K(k)(y(k) - H\hat{x}(k)) \quad 26$$

$$P^+(k) = (I - K(k)H)P(k) \quad 27$$

Because the stochastic Kalman filter uses the process and measurement noise covariance, whose equations are shown in Equation (28) and Equation (29), these covariance matrices must be determined.

$$Q = E[\omega(k)\omega^T(k)] \quad (28)$$

$$R = E[v(k)v^T(k)] \quad (29)$$

From FIG. 6D, there was an evident change in the x-axis measurement error as the x-position changed. The x position error was evaluated in uniform increments across the FOV and the mean and standard deviation of that x measurement error are shown in Table 2. The measurement noise covariance is only concerned with the measurement standard deviations (variances); however, note that the non-zero mean error is corrected using the least squares regression correction mentioned before.

TABLE 2

Micropipette tip x measurement error statistics across the FOV. The width of the FOV was divided into equally sized increments. For each of these increments, the mean and standard deviation of the x position were computed. The number of measurements comprising the computed statistics was also tabulated.

| X Position (Pixel) | X Error Mean (μm [pixels]) | X Error Std. (μm [pixels]) | N |
|---|---|---|---|
| [0-500] | −15.1 [−125.8] | 2.1 [17.5] | 4 |
| [501-1000] | −12.4 [−103.3] | 5.0 [41.7] | 15 |
| [1001-1500] | −7.8 [−65.0] | 6.5 [54.1] | 33 |
| [1501-2000] | −3.2 [−26.7] | 8.6 [71.6] | 44 |
| [2001-2500] | 1.7 [14.2] | 8.7 [72.5] | 34 |
| [2501-3000] | 3.3 [27.5] | 7.8 [65.0] | 22 |

Because the x error standard deviation changes substantially across the FOV, a schedule is created to change the measurement noise covariance as a function of the position of the micropipette in the FOV. For the x-axis entry in the covariance matrix is scheduled to change according to the following position in Equation (30).

$$\sigma_x^2 = \begin{cases} 54.1^2 & \text{if } x \le 1500 \\ 72.5^2 & \text{if } 1501 < x \le 2500 \\ 65.0^2 & \text{otherwise} \end{cases} \quad (30)$$

The y measurement error is relatively consistent across the FOV, so the y-axis entry in the covariance matrix is set to be constant across the whole FOV as shown in Equation (31).

$$\sigma_y^2 = 4.2^2 \quad (31)$$

The cross terms in the covariance matrix are ignored, so the measurement noise covariance matrix is constructed according to Equation (32).

$$R = \begin{bmatrix} \sigma_x^2 & 0 \\ 0 & \sigma_y^2 \end{bmatrix} \quad (32)$$

The process noise covariance was constructed by manually annotating the micropipette's tip position FOV as it attempted to maintain a constant position. Ultimately, this method of constructing the process noise does not account for the drift of the pipette, but those dynamics are not modeled. While this leads to a non-optimal Kalman filter, we still saw positioning improvements following a Kalman filter update. Like the measurement noise covariance, cross terms were ignored, and the x and y axis terms were computed by evaluating the statistics of each axis independently.

$$Q = \begin{bmatrix} 3.0^2 & 0 \\ 0 & 13.3^2 \end{bmatrix} \quad (33)$$

By looking at the covariance matrices we can see that the measurements are very accurate in the y axis but less so for the x axis. Conversely the process noise covariances, shows that there positioning of the x axis is much better than the y axis (because of the drift). Ultimately, this enables us to better correct the y inaccuracy with our measurement while relying more on the micromanipulator's accuracy in the x axis to hold the x position better.

With the dynamic model formulated and the covariance matrices constructed, the Kalman filter can be implemented according to the Equations (23)-(27). As micropipette 118 is moving along its pre-determined path to a cell, a priori updates are occurring each time the micropipette 118 completes a move. As micropipette 118 makes its final approach to a cell, micropipette 118 may stop 10-30 μm away from the cell at an abutment position. The Kalman filter makes an a priori update, takes a measurement of the micropipette tip position, and then completes an a posteriori update. If the difference between the desired position and the a posteriori estimated position exceeds a user defined threshold, robotic microinjection system 100 moves micropipette 118 the computed distance and direction towards the desired position and makes an attempt to inject the cell from the corrected position.

The system may reject measurements if the measurements exceed two times the state estimation covariance value as computed by the Kalman filter. This may prevent spurious measurements caused by a variety of factors from causing a position correction that would further misalign the true micropipette trajectory and the desired pipette trajectory.

The computer vision algorithms allow robotic microinjection system 100 to target single cells for injection, not only in 2D but in 3D space. Robotic microinjection system 100 may incorporate a cell quality metric that defines the viability of a cell for attempted microinjection, so injections can be prioritized to cells most likely to result in successful attempts. Additionally, robotic microinjection system 100 may implement a computer vision algorithm and a Kalman filter to track the micropipette tip in tissue and facilitate accurate microinjection by minimizing positioning errors. With this system, different microinjection parameters that affect injection success rates in a variety of cell types across the mouse spinal cord dorsal horn and striatum may be systematically explored. Through this systematic parameter sweep, robotic microinjection system 100 was able to achieve resulting success rates nearing 100% in both tissue types. These high microinjection success rates across tissue and cell types may allude to the potential of robotic microinjection system 100 for generalizability across many other cell types and neuronal tissues.

Robotic microinjection system 100 took inspiration from and improved upon numerous aspects of a similar system for high-throughput microinjection of single cells in organotypic slices (G. Shull, C. Haffner, W. B. Huttner, S. B. Kodandaramaiah, and E. Taverna, "Robotic platform for microinjection into single cells in brain tissue," EMBO Rep., vol. 20, no. 10, p. e47880, October 2019, doi: 10.15252/embr.201947880). While the previous system was capable of single cell injections, it was not single cell specific because it targeted different cell populations by modulating the injection depth to target spatially distributed cell populations. Moreover, the previous system was not capable of targeting specific z-positions in tissue. Finally, the previous system only automated the injection trajectory; target position annotation and calibration updates were manually completed by the user. Contrasting these limitations with the newly developed system, robotic microinjection system 100 is now capable of targeting specific individual cells in 3D space that were manually annotated or automatically detected and selected for injection. Likewise, the injection trajectory, target positioning annotation, and positioning correction are all automated.

Robotic microinjection system 100 may also incorporate improvements that may be of interest to labs doing automated patch clamping. Vision guided microinjection and vision guided patch clamping face a similar fundamental challenge: accurately positioning a micropipette at/in a cell in 2D/3D space to achieve the desired task. To this end, those doing patch clamping may be interested robotic microinjection system 100 for identifying cells positions in 3D space and our pipette positioning compensation approach. Recently, machine learning algorithms have been developed for locating cells using differential interference contrast (DIC) microscopy and locating the micropipette tip using DIC microscopy, but our approach could be applicable in situations where target cells exhibit a fluorescent signal is used like calcium imaging.

In some examples, the pipette positioning compensation is limited to only making corrections along the y-axis because the tip localization computer vision algorithm couples z-axis and x-axis drift so they are indistinguishable from each other. In some examples, robotic microinjection system 100 applies an autofocus algorithm, like H.-J. Suk, I. van Welie, S. B. Kodandaramaiah, B. Allen, C. R. Forest, and E. S. Boyden, “Closed-Loop Real-Time Imaging Enables Fully Automated Cell-Targeted Patch-Clamp Neural Recording In Vivo,” Neuron, vol. 95, no. 5, pp. 1037-1047.e11, August 2017, doi: 10.1016/j.neuron.2017.08.011, to ensure micropipette 118 is in focus before estimating the tip position and eliminate crosstalk of the z-axis and x-axis drift in the tip detection algorithm. Alternatively, one could train machine learning/pose estimation algorithms (or use pre-existing models, e.g., as described in Koos or M. M. Gonzalez, C. F. Lewallen, M. C. Yip, and C. R. Forest, “Machine Learning-Based Pipette Positional Correction for Automatic Patch Clamp In Vitro,” eNeuro, vol. 8, no. 4, July 2021, doi: 10.1523/ENEURO.0051-21.2021) to detect the tip locations of in- and out-of-focus pipettes in a variety of illumination settings to create a robust tip detection frame work that could work in DIC or epifluorescence. In some examples, robotic microinjection system 100 is limited to only targeting cells that express a fluorescent marker. In some examples, robotic microinjection system 100 applies machine learning algorithms to detect cells in DIC microscopy (e.g., like Koos and M. C. Yip, M. M. Gonzalez, C. R. Valenta, M. J. M. Rowan, and C. R. Forest, “Deep learning-based real-time detection of neurons in brain slices for in vitro physiology,” Sci. Rep., vol. 11, no. 1, Art. no. 1, March 2021, doi: 10.1038/s41598-021-85695-4), and expand the cell targeting potential.

Robotic microinjection system 100 may open the door to enabling a plethora of new approaches for probing and studying biology. Robotic microinjection system 100 may enable rapid and large-scale injection of exogeneous mRNA or CRISPR-Cas9 constructs into specific spatially or anatomically identified cell populations for genetic modification. Alternatively, robotic microinjection system 100 may be used to conduct high-throughput, microinjection-mediated oligonucleotide barcode labeling of distinct cell populations for transcriptomic profiling. Using this vision-based system, one could tie anatomical or spatial information with transcriptomic information for a new approach for spatially resolved transcriptomics. Or, if target cells exhibited fluorescently labeled calcium indicators, these functionally identified cells could be barcode labeled via microinjection and transcriptomically analyzed to understand their transcriptomic underpinnings.

In some examples, robotic microinjection system 100 may achieve even higher throughput by using a motorized x-y microscope stage to permit automatic FOV changing and motorized filter cube turret could be used to automate the frequent switching between fluorescent channels that identify different cell types or fluorescent dyes. Likewise, robotic microinjection system 100 may use swarms of micromanipulators to parallelize injections in the same FOV or across separate FOVs if robotic microinjection system 100 includes a motorized stage. Even with these throughput improvements, microinjection may be fundamentally throughput-limited by the need to replace frequently clogged pipettes or change tissue sections, so robotic microinjection system 100 may include systems to automatically conduct pipette changing and tissue handling. In addition to throughput improvements, robotic microinjection system 100 may implement multi-perspective imaging to visualize 3D structures and enable targeting in more complex tissues/organoids.

Figure 8:
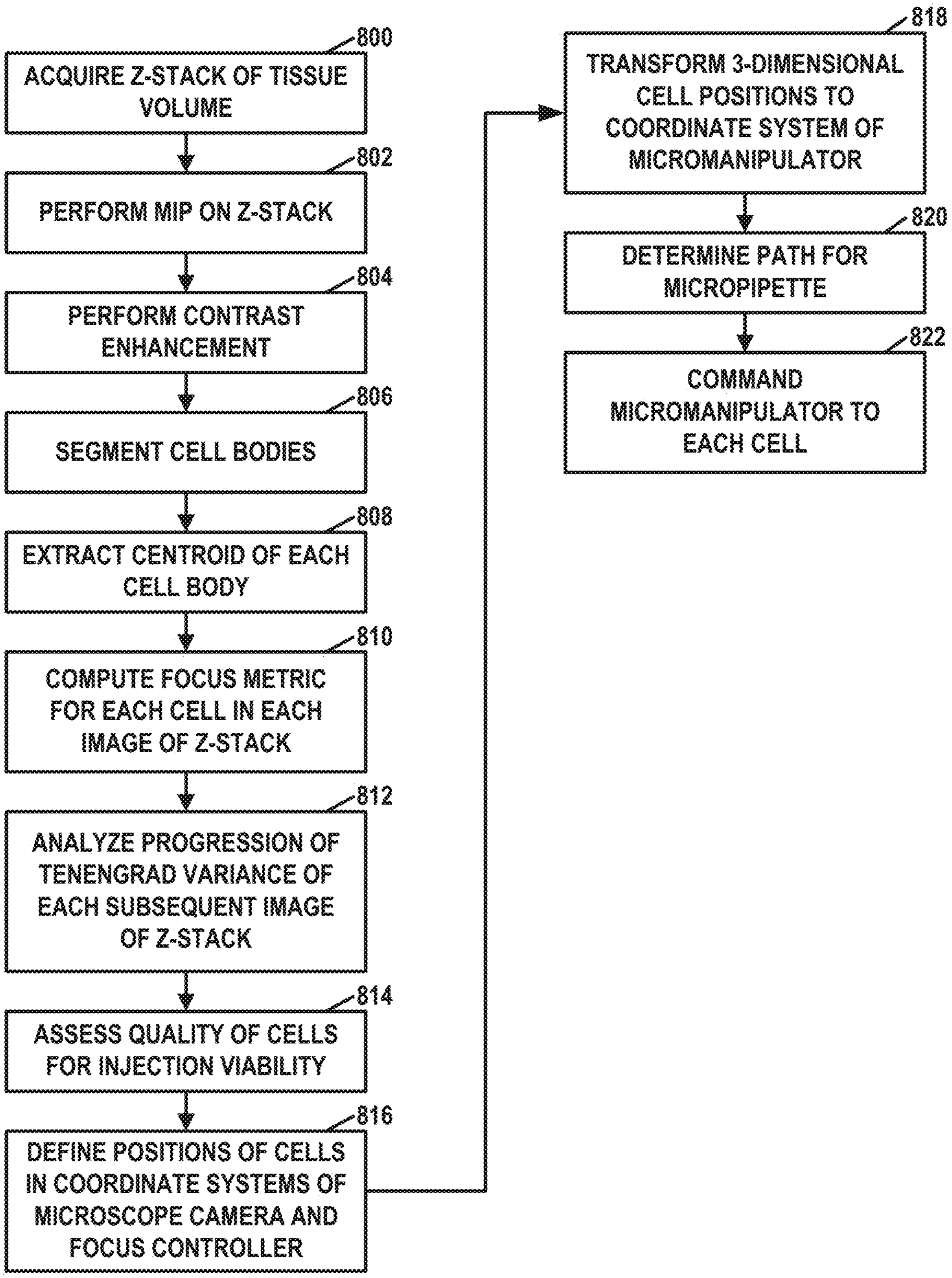
FIG. 8 is a flowchart illustrating an example operation for automatic cell detection and selection, and microinjection, according to techniques of this disclosure.

FIG. 8 is a flowchart illustrating an example operation for automatic cell detection and selection, and microinjection, according to techniques of this disclosure. To enable high-throughput, automated microinjection of single cells, a computer vision algorithm was devised to detect cells and note their locations in 3D space. Cells of interest express a fluorescent protein, so the algorithm uses images that are attained via epifluorescent microscopy. Given that the cells are emitting light at a higher intensity than the background fluorescence makes this specific detection process a prime target for a threshold-based algorithm.

The computer vision-based operation for automatic cell detection and selection can be broken down in to three major processes—cell x-y coordinate determination, cell z-coordinate determination, and cell quality determination. The x-y coordinate determination comprises (or, in some examples, consists of) volumetric imaging via taking a series of images in successively deeper sections of tissue (z-stack), compressing this z-stack into a single image using maximum intensity projection (MIP), contrast enhancement on the MIP, and threshold-based cell segmentation/detection. The cells' x-y coordinates are noted from the segmented cells' centroids. The z-coordinate determination is accomplished by computing a focus metric called the Tenengrad variance for each detected cell in each image of the z-stack. A gaussian distribution is fit to the Tenengrad variance data for each cell, and the mean of the gaussian distribution is used as the optimal z-coordinate of the cell.

During x-y coordinate determination, the process starts by acquiring a volumetric image of the tissue volume of interest. This is accomplished by acquiring a z-stack of the tissue volume (800). The user may specify a scan depth and distance between optical sections, and cell detection unit 516 automatically focuses on optical sections throughout the tissue volume and takes images of tissue sample 122. After the z-stack is acquired, cell detection unit 516 performs a MIP on the z-stack (802). This MIP compresses volumetric information from the z-stack into a single image, which may simplify processing. The following steps could be performed on each image in the stack, but using the MIP may reduce processing time as all the processing is done on a single image instead of the 10-20 images in the z-stack.

The resulting MIP tends to result in an image that has relatively low dynamic range as the background fluorescence tends to elevate the ground-floor pixel intensity. Consequently, attempting to segment and detect cells using the original MIP is challenging because the difference between fluorescent cells and the background is small. FIG. 7C shows a representative MIP and its histogram depicting the "nearness" of the cells' intensity to the background intensity. To overcome this issue, cell detection unit 516 may conduct contrast enhancement to improve the visibility of cells of interest (804). In some examples, a first step in contrast enhancement is Otsu's binarization which is a mathematical method to optimally separate a bimodal distribution by minimizing the variance in each of the bimodal classes; in other words, it finds a pixel value that converts an image histogram with a bimodal distribution into two unimodal distributions with minimized variances. Therefore, cell detection unit 516 may use Otsu's method a pixel intensity histogram to determine an optimal value at which to threshold the image. Using Otsu's method, an optimal pixel intensity value is acquired for the MIP image. All values below the Otsu pixel intensity are floored to zero, while the Otsu pixel intensity is subtracted from all remaining pixels as shown in Equation (34), below. A representative Otsu floored image is shown in FIG. 7C. Otsu-based flooring results in an image where a significant portion of the higher intensity values of the histogram are vacant of pixels as shown in FIG. 7C. Linear contrast enhancement may be conducted by multiplying each pixel intensity by a constant that is the maximum possible pixel intensity (256 for 8-bit images) divided by the maximum pixel intensity in the Otsu floored image as shown in Equation (35), below. A representative contrast stretched image and its histogram are shown in FIG. 7C. This method for contrast enhancement allows enhancement of only regions that are relevant (contain fluorescent cells) while "ignoring" regions that don't contain cells thereby making cell detection easier. Because the background and cell intensity tend to vary across the field of view (FOV), raw Otsu's binarization and the subsequent pixel intensity flooring occasionally "removes" image regions/cells that may otherwise be of interest. Consequently, the thresholding pixel intensity from Otsu's binarization is marginally reduced. The resultant image tends to include more cells for potential detection targets. While this modification does reduce the amount of contrast stretching that can be achieved, it was experimentally determined to not affect the efficacy of cell detection. It was determined that an 18% decrease in Otsu pixel intensity was sufficient to capture most cells that were removed from the FOV.

$$I_{otsu\ floor} = \left\{ \begin{array}{ll} 0 & \text{if } I_{original} \leq i_{otsu} \\ I_{original} - i_{otsu} & \text{if } I_{original} > i_{otsu} \end{array} \right\} \quad (34)$$

$$I_{contrast\ enhance} = I_{otsu\ floor} \times \frac{256}{\max(I_{otsu\ floor})} \quad (35)$$

Following contrast enhancement, cell detection unit 516 may segment cell bodies from the background to identify discrete cells for injection (806). As mentioned before, the fluorescent nature of the cells of interest permits the use of thresholding to detect cells, therefore cell detection/segmentation is accomplished via adaptive thresholding which results in a binary image wherein white blobs are segmented cell bodies and black is considered to be background. Adaptive thresholding was used because the tissue slice MIPs tend to have an uneven illumination profile, so using global thresholding would eliminate cells of interest in darker regions of the image despite being noticeably brighter than the local background. A representative image of an adaptive threshold mediated cell segmentation is shown in FIG. 7D.

After cell segmentation, cell detection unit 516 may extract the centroid of each detected cell body (808). In other words, cell detection unit 516 may determine the x-y coordinates of the centroids of the detected cell bodies. In some examples, cell detection unit 516 determines the centroids of the detected cell bodies through OpenCV's contour functions operating on each detected cell/contour. An image depicting the detected cell centroids (circles) and bounding boxes around the detected cells (boxes) is shown in FIG. 7E.

From the cell x-y coordinate determination, cell detection unit 516 has data indicating the x-y coordinates of each cell within the MIP, but cell detection unit 516 is still unaware of how deep (z-coordinate) each cell is within the tissue slices. Consequently, z-coordinate determination must also be performed prior to injection in order to fully realize the cells' positions. Z-coordinate determination is accomplished by computing a focus metric for each detected cell in each image of the stack, and finding the depth associated with optimum value of the focus metric to use as the z-coordinate of the cell.

As a first step in z-coordinate determination, cell detection unit 516 may compute a focus metric for each cell in each image of the z-stack (810). Cell detection unit 516 may use the Tenengrad variance because the Tenengrad variance may provide high-speed and good performance for fluorescent cell detection. Moreover, upon comparing numerous focus metrics including the Tenengrad variance, Laplacian variance, and detected cell size, the Tenengrad variance is more optimally computed the in-focus frame. The Tenengrad variance is the variance of the image gradient. More simply, a high Tenengrad variance would mean that there is a large change in gradients across the image and a low Tenengrad variance means that there are minimal changes in gradient like a uniform image. Consequently, if a cell is in focus, then there would be sharp boundaries/gradients at the edges of the soma resulting in a large Tenengrad variance.

Once the Tenengrad variance is computed for each cell in each image of the stack, cell detection unit 516 may analyze the progression of the Tenengrad variance for each subsequent image of the z-stack (812). Optimally, one would expect the Tenengrad variance to be low when the cell is out of focus, gradually increase to a peak as the cell comes into focus, and finally decrease as the cell goes out of focus. Specifically, the focus metric follows a relatively gaussian process. Therefore, following focus metric computation, a gaussian distribution is fit to the focus metric trajectory. The mean of the Gaussian distribution (associated with the theoretical peak value of the focus metric) is then used as the optimum in-focus point of the cell. Because the units of the gaussian distribution are optical sections, the mean value can be converted to the manipulator coordinate frame by knowing the calibration between the focus drive and the manipulator and using the optical section step size.

Following location identification, cell detection unit 516 may assess the quality of each cell for its injection viability (814). Cell detection unit 516 may assess a viability of the respective cell for injection viability based on a focus metric for the respective cell. For instance, cells exhibit highly variable focus profiles. Some cells are very blurry when out of focus and come into bright and sharp relief when they are in focus, whereas other cells are never well-defined within the focus profile. During manual microinjection, a user would be most apt to select the cells that come into sharp relief as opposed to the cells that remain blurry. Consequently, the cell quality score (i.e., focus metric) aims to mimic this intuition by giving high scores to those cells that become more well-defined as they come into focus. This intuition is further supported by the literature which assumes that the focus/defocus process follows a Gaussian model, so it is expected that focus metric for each cell should follow a relatively Gaussian distribution. More specifically, the cell quality is a measure of how well the cells follow a Gaussian focus profile. Cell detection unit 516 may compute cell quality using a combination of the covariance of the gaussian fit parameters as well as the pseudo-$R^2$ value to explain how closely the computed Tenengrad variance fits to the fitted Gaussian distribution. In other words, cell detection unit 516 may determine the focus metric for the respective cell based on a combination of a covariance of parameters of the gaussian distribution and a pseudo-$R^2$ that indicates how closely the Tenengrad variance fits to the gaussian distribution. A comparison between a high scoring cell and a low scoring cell is shown in FIG. 61. The high scoring cell has a much better fitting focus profile and the images near the optimum z coordinate exhibit a better-defined soma then the lower scoring cell. The goal of assessing the quality of a cell is also common for deep learning driven automated electrophysiology systems wherein detected cells are assigned a confidence value that denotes the probability of the detected cell indeed being a cell. With the deep learning approach, cells with the highest confidence values can be targeted for electrophysiology.

Through the cell detection process, cell detection unit 516 detect some false positives or positively identify a cell but, an experienced researcher may not want to attempt to perform injections on the cell because the cell is poorly defined in the tissue. To accommodate these issues, a quality metric was devised to assign scores to the cells so researchers can prioritize injections to highly scoring cells. A "good" cell is one that has a blurry fluorescent profile when out of focus, sharpens predictably as it comes into focus, and has well-defined cell boundaries when the cell is in focus. Therefore, one would expect the focus metric profile to follow the gaussian distribution mentioned before, so quality metrics are derived from statistics relating the raw data of the Tenengrad variance and its fit to a gaussian distribution.

Cell detection unit 516 may use a combination of the gaussian distribution estimated parameter covariance trace and a pseudo-$R^2$ value as the quality metric. The covariance matrix provides an indicator of the accuracy of the gaussian distribution in fitting the data's mean, standard deviation, and the peak value. A trace of 0 for the covariance matrix would indicate that the gaussian distribution perfectly fits the data. A high covariance matrix trace would indicate a large variation between the data and the gaussian distribution parameter. Therefore, a covariance matrix trace close to 0 is desired which indicates that a highly accurate prediction of the raw data from the gaussian distribution. In addition to the trace of the covariance, cell detection unit 516 may compute the pseudo-$R^2$ value by:

$$\hat{R}^2 = 1 - \frac{sse}{sst}$$

$$sse = \sum_{i=1}^{n} \left[(y_i - \bar{y})^2\right]$$

$$sst = \sum_{i=1}^{n} \left[(y_i - y_{fit,i})^2\right]$$

$\gamma_i$ denotes the focus metric value from each image. $\bar{y}$ denotes the mean focus metric value for all images. $y_{fit,i}$ denotes the focus metric value from the fitted gaussian distribution at that image.

This pseudo-$R^2$ value indicates how well the variation in the data can be explained by the fitted gaussian distribution. A high pseudo-$R^2$ value means that the data is well explained by the fitted distribution whereas a low value indicates minimal relationship between the fitted distribution and the data. Therefore, a high pseudo-$R^2$ value is desired as it means the focusing process of the cell is well explained by a gaussian process. The final score metric is shown in Equation (35), below, where $\sigma_{ii}$ are the diagonal elements of the covariance matrix (for computing the trace of the covariance) and $\hat{R}^2$ is the pseudo-r2 value.

$$\text{score} = 1 - \sum_{i=1}^{N} (\sigma_{ii}) \times \left(1 - \hat{R}^2\right) \tag{35}$$

The covariance entries are bounded between 0 and positive infinity and the pseudo-$R^2$ values are bounded between 0 and 1 which results in a score between 1 (optimal) and negative infinity (poor). With this score, a user can experimentally choose a threshold that is satisfactory for their specific conditions to optimally choose cells for injection.

After the x, y, z position of micromanipulator 114 is known relative to microscope camera 110 and focus controller 108 and the x, y, and z positions of the cells are known, cell detection unit 516 to define the positions of cells relative to coordinate systems of microscope camera 110 and focus controller 108 so the cells can be targeted for injection (816). Cell detection unit 516 may then transform the 3-dimensional cell positions into a coordinate system of micromanipulator 114 (818).

Finally, once the positions of micromanipulator 114 and the cells are known, injection control unit 518 targets the detected cells for barcoded microinjection. Depending on the tissue and the desired experiment, multiple tens of cells may be targeted for injection. Injection control unit 518 may determine a path for micropipette 118 (820). In some examples, injection control unit 518 implements a path finding algorithm to optimize the travel time between cells and enable high-throughput injections when large quantities of cells are targeted for injection. In this way, injection control unit 518 may determine a trajectory of the micropipette among the one or more cells of the cell population.

Once the path is determined, injection control unit 518 commands micromanipulator 114 to each subsequent cell for injection (822). When traveling between cells, micromanipulator 114 may move micropipette 118 at a height of approximately 20 μm-50 μm above the tissue to prevent tissue debris from clogging the tip. A pre-injection position is computed by assuming orthogonal micromanipulator axes and using the micropipette's height above the tissue (Δz in FIG. 1*c*) and the angle of micromanipulator's diagonal axis to determine how far away from cell (Δx in FIG. 3F) the micropipette tip must be such that its diagonal axis aligns with the cell centroid. At each cell's pre-injection position, micromanipulator 114 attempts injection by advancing micropipette 118 along the diagonal axis (Δd in FIG. 3F) of micropipette 118 to the approximate center of the cell, and pressure controller 106 increases the pressure inside micropipette 118 to attempt to inject the payload into the cell. This process is continued for all the targeted cells.

During injections, multiple factors may cause positioning error between the actual micropipette position and the desired micropipette position. Some of these factors may include uncorrected FOV distortion, objective distortion Petzval field, curvature, pipette drift from the micromanipulator or other hardware, and user error during micropipette calibration. Accordingly, injection control unit 518 may correct the micropipette trajectory to a cell in the event of micropipette positioning inaccuracy using computer vision or machine learning based algorithms and a Kalman filter. Thus, in some examples, to mitigate the effects of these disturbances, a computer vision algorithm was devised to measure the (x,y) pixel coordinates of the micropipette tip for a micropipette filled with a fluorescent injection solution. A Kalman filter was designed to fuse information from the computer vision measured tip coordinates and micromanipulator dynamics to generate an optimal estimate of the (x,y) coordinates of the tip of micropipette 118 in the FOV. With this estimate of the tip's coordinates, injection control unit 518 can implement trajectory modifications to better align the injection trajectory with the center of the cell to improve positioning accuracy and facilitate a higher injection success rate.

In some examples, injection control unit 518 may determine whether a cell was successfully injected. For instance, injection control unit 518 may apply a machine learning (ML) model, such as a YOLOv5™ model, to images generated by microscope camera 110 to determine whether a cell was successfully injected.

As noted above, cell detection unit 516 may compute cell quality. In some examples, cell detection unit 516 may assess the viability of a cell using a logistic regression model trained on image-based features of successfully injected cells to predict a probability of a successful injection of the cell. For instance, cell detection unit 516 may compute a cell quality metric by using logistic regression to determine a weighting or statistical model for a cell's image-based features and their relation to injection success. Logistic regression is a machine learning algorithm that relates inputs to a binary output (contrasting with linear regression which relates inputs to a continuous/discrete output)—in our case of logistic regression, the inputs are a cell's image-based features, and the binary output is injection success or failure. Conceptually, the output of a trained logistic regression model is the probability that a given set of inputs belong to a certain output class (analogously, the output for a fitted linear regression model would be the most likely output value for the given set of inputs). Specifically, in the case of cell selection, the output of the trained logistic regression model is the probability of injection success, and this probability is used as the cell quality metric score. Hence, this approach is directly aligned with the goal of selecting cells for injection based on maximizing the injection success rate.

To train the cell selection logistic regression model, data for the image-based feature inputs and the resulting injection outcomes may be compiled. The following discussion describes how this data was compiled, how the image-based features were selected to be used in the logistic regression model, and the resulting performance of the logistic regression model.

A first step in training a logistic regression model is compile the data to be used in training the model. During microinjections, we saved a variety of data including a picture of the cell, the injection success outcome for each cell, and a variety of other image-based features described in rows 1-15 of Table 3. Some of these features were then used to create additional image-based features as described in rows 16-20 of Table 3. In total, we compiled image-based features for 481 cells in 46 FOVs across 4 mice.

TABLE 3

Image-based cell features and their descriptions. These image-based cell features were compiled for training a logistic regression algorithm to predict injection success rate.

| | Image-based feature | Description |
|---|---|---|
| 1 | Pseudo-$R^2$ | The pseudo-$R^2$ of the fitted Gaussian distribution and it's explanation of the raw Tenengrad variance data. |
| 2 | Gaussian fit amplitude variance | Taken from the fitted Gaussian distribution covariance matrix. The variance of the fitted amplitude value. |
| 3 | Gaussian fit mean variance | Taken from the fitted Gaussian distribution covariance matrix. The variance of the fitted mean value. |
| 4 | Gaussian fit standard deviation variance | Taken from the fitted Gaussian distribution covariance matrix. The variance of the fitted standard deviation value. |
| 5 | Gaussian fit amplitude value | The amplitude of the fitted Gaussian distribution. |
| 6 | Gaussian fit mean value | The mean of the fitted Gaussian distribution. |
| 7 | Gaussian fit standard deviation value | The standard deviation of the fitted Gaussian distribution. |
| 8 | Maximum Tenengrad variance | The maximum value of the Tenengrad variance for all the cell's images in the z-stack. |
| 9 | Average pixel intensity of cell | The average pixel intensity of the cell in the "most in-focus" image computed by the Tenengrad variance. |
| 10 | Standard deviation of pixel intensity of cell | The standard deviation of the pixel intensity of the cell in the "most in-focus" image computed by the Tenengrad variance. |

TABLE 3-continued

Image-based cell features and their descriptions. These image-based cell features were compiled for training a logistic regression algorithm to predict injection success rate.

| | Image-based feature | Description |
|---|---|---|
| 11 | Average pixel intensity of background in cell ROI | The average pixel intensity of the background for the cell's ROI in the "most in-focus" image computed by the Tenengrad variance. |
| 12 | Standard deviation of pixel intensity of background in cell ROI | The standard deviation pixel intensity of the background for the cell's ROI in the "most in-focus" image computed by the Tenengrad variance. |
| 13 | Cell size | The size of the cell in the "most in-focus" image computed by the Tenengrad variance. |
| 14 | Normalized variance | The normalized variance value for the "most in-focus" image computed by the Tenengrad variance. (Normalized variance is another common focus metric). |
| 15 | Vollath's autocorrelation | Vollath's autocorrelation value for the "most in-focus" image computed by the Tenengrad variance. (Vollath's autocorrelation is another common focus metric, especially for fluorescent cells). |
| 16 | Cell-background average intensity ratio | The ratio of the average pixel intensities between the cell and the cell's ROI background, (row 9/row 11) |
| 17 | Cell-background standard deviation of intensity ratio | The ratio of the average intensities between the cell and the cell's ROI background, (row 10/row 12) |
| 18 | Cell signal-to-noise (SNR) ratio | The ratio of the average pixel intensity to the standard deviation of pixel intensity for the cell, (row 9/row 10) |
| 19 | Background signal-to-noise (SNR) ratio | The ratio of the average pixel intensity to the standard deviation of pixel intensity for the background of the cell ROI. (row 11/row 12) |
| 20 | Cell SNR - background SNR ratio | Ratio of the cell SNR to the background SNR. (row 18/row 19). |

After the training data is compiled, cell detection unit 516 may process the training data to improve the performance of the logistic regression model. Processing the image-based features may include (or, in some examples, consist of) first normalizing the features by FOV and then transforming the distributions of the features to approximate the standard normal distribution. Normalization by FOV is implemented to reduce variability in imaging conditions across FOVs, tissue types, or cell types. Without this step, a particular FOV/cell type/tissue type with brighter/dimmer illumination profiles may skew the image-based features in a certain direction and reduce image-based feature consistency. FOV normalization was accomplished by dividing each cell's image-based features by the mean of the image-based features for all detected cells in that FOV.

After feature normalization by FOV, the features' distributions were transformed to approximate the standard normal distribution. The next step of transforming the features to approximate the standard normal distribution is not required for logistic regression, but it aided in visually analyzing the features and selecting features as inputs into logistic regression. By converting all the features to the standard normal distribution, it is easier to compare the features against each other by using the statistics of their distributions rather than arbitrarily comparing across the different units for different features. For instance, a side-by-side comparison of features can be achieved by analyzing how successfully injected cells may have one feature with values 1 standard deviation above the mean while having another feature with values 3 standard deviations above the mean. This transformation to a normal distribution consisted of using a statistical test to determine if the data could be considered to follow a normal distribution. If not, the data was transformed to be approximately normal using the Box Cox transformation. Once the data is approximately normal, cell detection unit 516 may normalize all data for each feature to approximate the standard normal distribution by subtracting the mean value and dividing by the standard deviation for that feature.

Logistic regression can determine an optimized weighting for all the image-based features and their relation to injection success, but slightly improved performance was achieved by limiting the input features to only those that had substantial impact on yielding a successful injection. This feature selection was achieved by visually examining the feature data between successfully and unsuccessfully injected cells. For each mouse, the mean value of each feature was computed. Then the average was taken of each feature's mean values across all mice.

With the input data compiled, processed, and selected, the logistic regression model was trained on the available data (e.g., 481 cells in 46 FOVs across 4 mice). To reduce the impact of any poorly performing model fittings from a certain training/test data split, a Monte Carlo method-style logistic regression fitting was conducted. The logistic regression training was repeated 1000 times for different test/training data splits (all splits used 90% training data and 10% test data). The average logistic regression model was then used as the model to be applied in novel situations. The results from the logistic regression training yielded 62% precision, 87% recall, and 28% specificity. The same data used to train a classification neural network in the same Monte Carlo method-style to determine if using a more complex machine learning algorithm would be beneficial, but it performed similarly (59% precision, 72% recall, and 34% specificity). Logistic regression may have simpler implementation and have an ability to find successfully injected cells (higher recall) even though logistic regression will occasionally select more unsuccessful cells (lower specificity).

Figure 9:
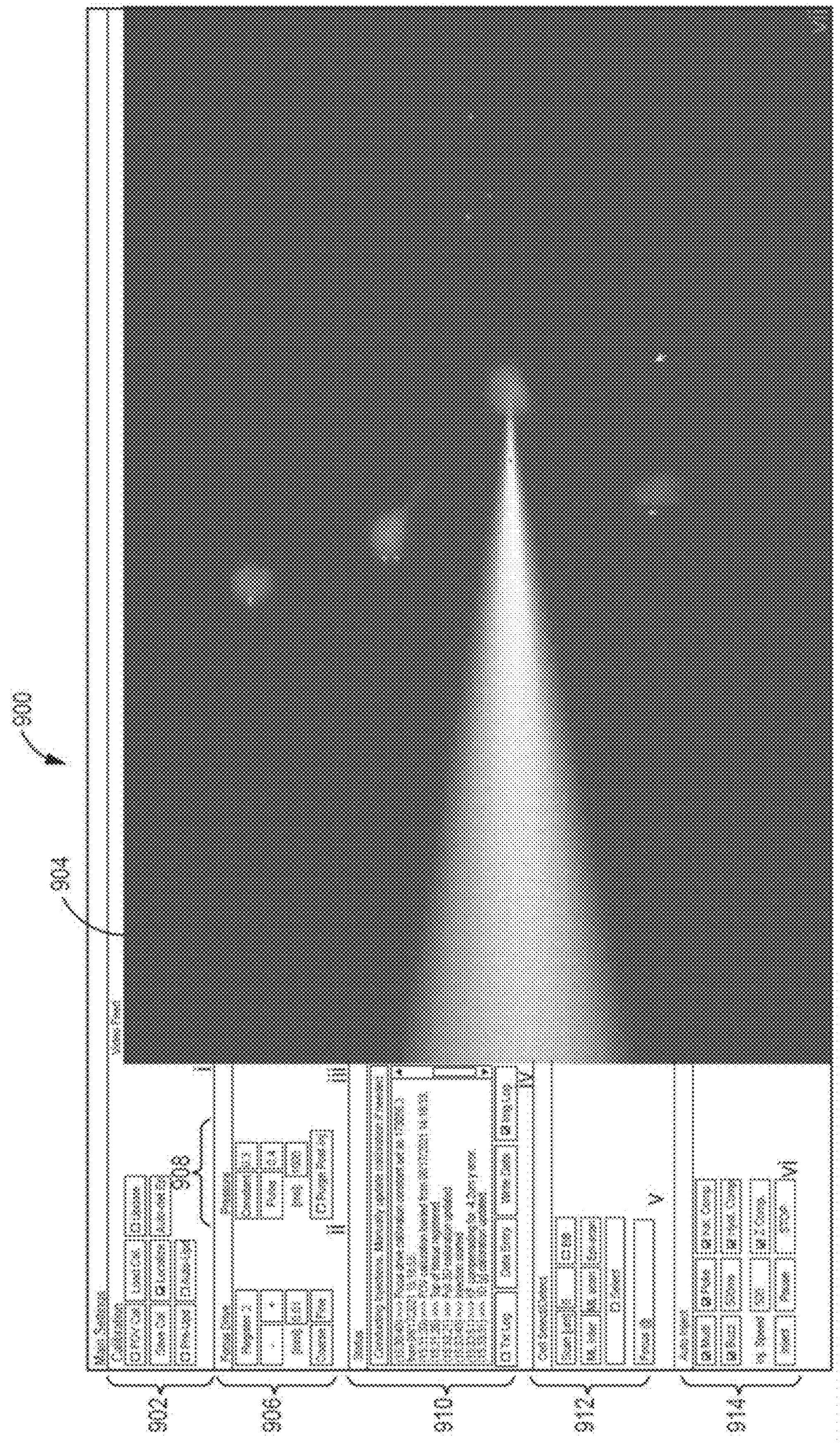
FIG. 9 is a screen diagram illustrating an example graphical user interface (GUI) for robotic microinjection according to techniques of this disclosure.

FIG. 9 is a screen diagram illustrating an example GUI 900 for robotic microinjection system 100 according to techniques of this disclosure. GUI 900 has groups of widgets including buttons, entry boxes, and dropdowns that allows the user to control the microinjection process. It also displays live video feed from the microscope camera to allow the user to visualize the injections. In the example of FIG. 9, calibration widgets 902 allow a user to create and modify the micromanipulator calibration. Calibration widgets 902 include buttons that permit the user to load a previous calibration, conduct a new calibration, update the current calibration, and save the current calibration to be loaded later. Calibration widgets 902 also include a check button that overlays the calibration position on a video display 904 which helps identify when the pipette needs to be recalibrated (evident when the micropipette tip and overlaid calibration position are not coincident). Additionally, there is a check button to perform automated Kalman filter facilitated calibration updates periodically through-out the experimental trial. Interactive video display 904 displays live video from the microscope camera. The user may also use the display to click on the micropipette to select calibration points or select cells for injection.

Focus controller widgets 906 permit user control of the microscope's fine focus wheel. The user can use focus controller widgets 906 to traverse the focal plane up and down, and the user can change the step size in the entry box. The user also uses the "Register Z" button during every experimental trail to register the top of the tissue which tells the system to keep micromanipulator 114 above this z height when not attempting injections.

Pressure control widgets 908 allow the user to set the magnitude of the pulse pressure and constant back pressure (which helps to reduce clogging) and the duration of the pressure pulse. The user can the buttons to manually apply the constant or pulse pressure. Additionally, there is a check button option that can be selected which causes the system to perform high-pressure purges after each injection to also reduce clogging (this feature has not been extensively tested).

Status bar and data saving widgets 910 include two text boxes that provide the user with prompts to guide them in performing the next step in the injection process as well as provide text feedback on the status of the system. Buttons are used to save text data related to the injection trial as well as images of the z-stack for cell detection or images of the injection process.

Cell selection widgets 912 allow the user to initiate an automatic scan to detect cells and overlay their bounding boxes in the video display. There is also a "Select" button that allows the user to manually select cells for injection or automatically select the detected cells. A drop-down box allows the user to select predefined focal planes to focus on which correspond to the selected cells for visualizing injections.

Injection widgets 914 include buttons and check boxes to control various parameters of the injection process like changing the injection speed, using multi-point injection approach, using poke penetration, using buzz penetration, enabling Kalman filter position correction, using a hysteresis compensated movement pattern, and compensating for z-axis discrepancy across FOV. There are also buttons to start and stop the injection process.

Figure 10:
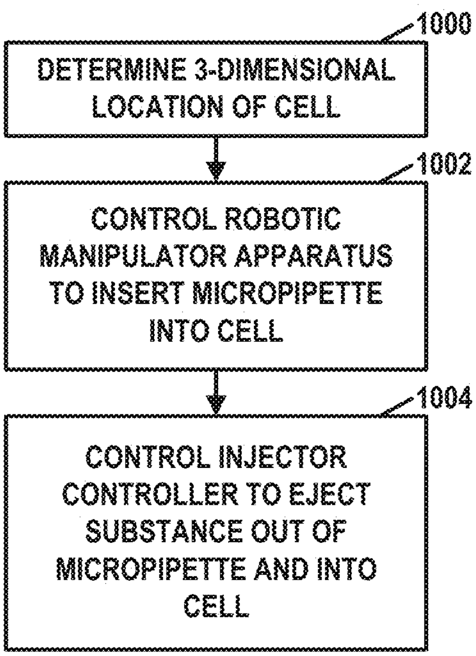
FIG. 10 is a flowchart illustrating an example operation according to techniques of this disclosure.

FIG. 10 is a flowchart illustrating an example operation according to techniques of this disclosure. In the example of FIG. 10, for each respective cell of a plurality of cells of a cell population at a plurality of depths within a tissue sample, computing device 102 may determine a 3-dimensional location of the respective cell based on images formed by microscope 112 and captured by microscope camera 110 (1000). Computing device 102 may control a robotic manipulator apparatus (micromanipulator 114) to insert micropipette 118 into the respective cell (1002). Computing device 102 may control an injector controller (pressure controller 106) to eject the substance out of micropipette 118 and into the respective cell (1004).

Accurate pipette positioning plays an important role in achieving successful microinjection of targeted cells. The targeted cells are approximately 10-20 μm in diameter, and the tip of micropipette 118 must be positioned near each cell's center to successfully inject the cell. Positioning errors on the micrometer scale can cause micropipette 118 to completely miss the cell or displace the cell without piercing the cellular membrane. These positioning errors manifest from phenomena like pipette drift and unmodeled robotic kinematics in the calibration process. Such phenomena may be too complex and/or dynamic to construct an accurate open-loop model that would be capable of compensating for the positioning errors. Therefore, a closed-loop model with measurement feedback of the pipette tip position may implemented to correct for the pipette positioning errors.

Figure 11:
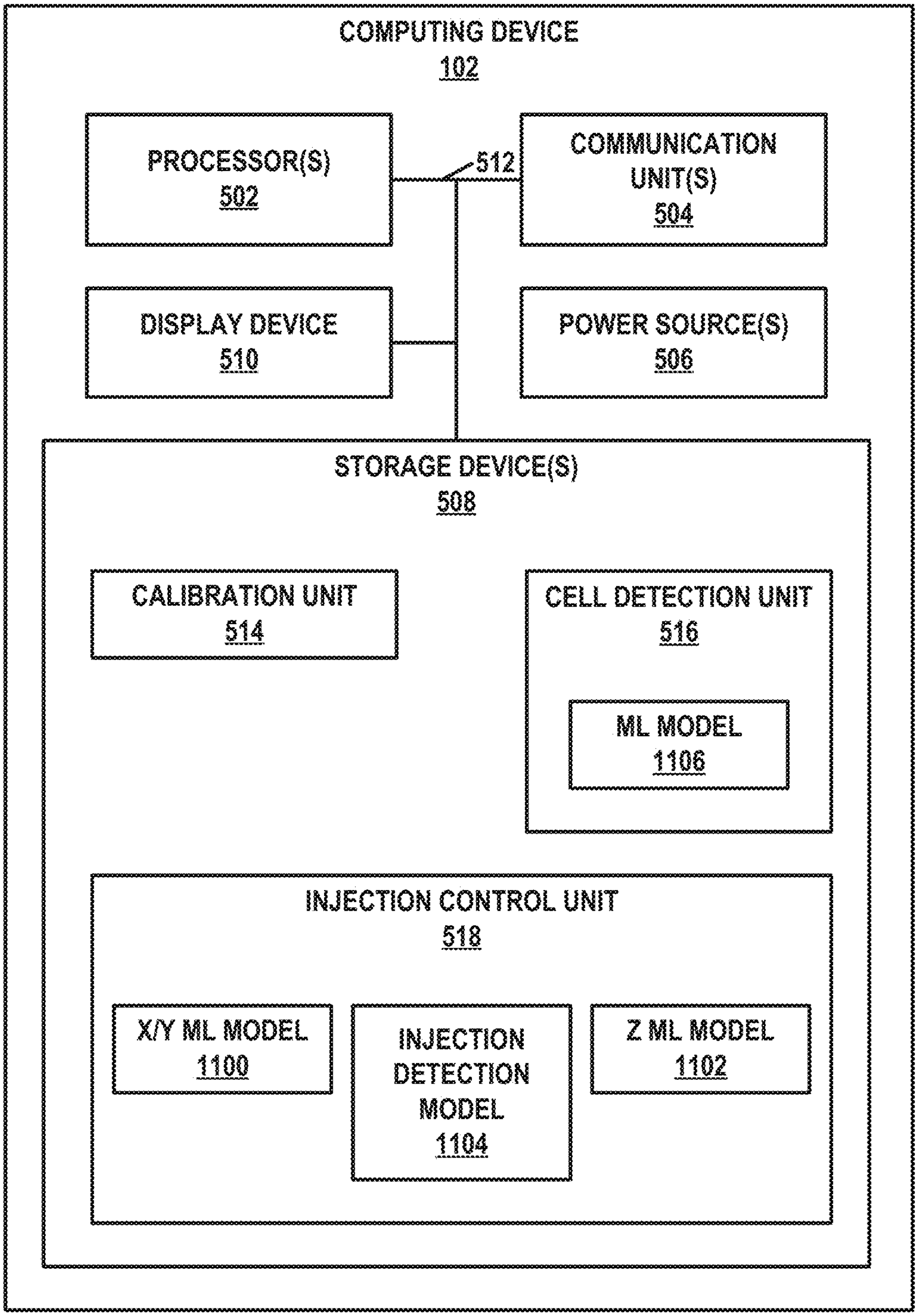
FIG. 11 is a block diagram illustrating example components of a computing device according to techniques of this disclosure.

FIG. 11 is a block diagram illustrating example components of computing device 102 according to techniques of this disclosure. In the example of FIG. 11, computing device 102 includes the same components as example computing device of FIG. 5. However, in the example of FIG. 11, cell detection unit 516 may include a ML model 1106. Cell detection unit 516 may apply ML model 1106 to images in a z-stack to segment cells in the images. An example process that uses ML model 1106 for cell detection is described with respect to FIG. 15, below.

Furthermore, in the example of FIG. 11, injection control unit 518 includes an X/Y ML model 1100, Z ML model 1102, and an injection detection model 1104. X/Y ML model 1100, Z ML model 1102, and injection detection model 1104 may be implemented as You Only Look Once version 5™ (YOLOv5™) models or another type of ML model, such as YOLOv3™, YOLOv4™ or a non-YOLO image classification or object detection model. YOLOv5™ models are suitable for use a X/Y ML model 1100, Z ML model 1102, and injection detection model 1104 because YOLOv5™ models may provide reliable and fast classification of areas within images. For ease of explanation, the remainder of this disclosure assumes that X/Y ML model 1100, Z ML model 1102, and injection detection model 1104 are implemented as YOLOv5™ models.

Injection control unit 518 may apply X/Y ML model 110 to measure a 2D (x, y) position of the tip of micropipette 118 prior to Kalman Filter tip position estimation and subsequent positioning correction. 2D (x, y) position refers to the position of the tip of micropipette 118 within the image plane (a.k.a. the camera's pixel coordinates of the pipette tip). Use of a YOLOv5™ model may be an alternative position measurement system to the computer vision algorithm detailed elsewhere in this disclosure.

The computer vision algorithm described elsewhere in this disclosure realized a 2D (x, y) pipette tip localization solution that included a computer vision algorithm and Kalman Filter. The computer vision algorithm described elsewhere in this disclosure takes a measurement of the pipette tip position, and this measurement is fused with dynamical system information in the Kalman Filter to generate an improved estimate of the pipette tip position. Using this two-step approach (measurement followed by Kalman Filter) permits reduction of uncertainty in the measurements (all real-world measurement systems are subject to noise and biases).

YOLOv5™ was implemented for 2D (x, y) position measurement with the aim of improving the computer vision algorithm. Namely, YOLOv5™ aims to improve upon the computer vision algorithm's lower accuracy of axial (x) measurements. YOLOv5™ also aims to improve upon the computer vision algorithm's sensitivity to additional fluorescence in the field of view (like previously injected cells that may interfere with the algorithm's ability to fit lines to the fluorescent pipette shank).

In the example of FIG. 11, X/Y ML model 1100 may be trained on fluorescent images of micropipette 118 filled with a fluorescent injection solution that were taken during microinjection experiments. Images were annotated by drawing bounding boxes around the tip of micropipette 118. After training, injection control unit 518 may use X/Y ML model 1100 as a primary method for measuring the tip of micropipette 118. The output of X/Y ML model 1100 may be a bounding box around the pipette tip. Injection control unit 518 may take the centroid of the bounding box as the pixel (x, y) measurement of the tip position. During microinjection, micropipette 118 approaches the injection position and stops a predetermined distance (e.g., ~15 μm) from the position to attempt a 2D (x, y) measurement using ML model 1100. If the X/Y ML model 1100 cannot take a measurement, injection control unit 518 attempts a measurement using the computer vision algorithm described above. Injection control unit 518 then provides the measurement is as input into the Kalman Filter, the pipette position is corrected, and finally injection is attempted.

In addition to 2D (x, y) position measurement, Z ML model 1102 (e.g., another YOLOv5™ model) may be implemented to measure the 1D (z) position of the tip of micropipette 118. The 1D (z) position refers to the position of the tip of micropipette 118 along the focal axis of microscope 112. In other words, the 1D (z) position may be a coordinate of the tip of micropipette 118 used by focus controller 108. Z ML model 1102 may be able to generate 1D (z) position measurements by detecting whether the tip of micropipette 1102 is in-focus or out-of-focus. Use of Z ML model 1102 may improve measurement of the 1D (z) coordinate because the same types of errors that effect 2D (x, y) positioning (e.g., pipette drift and unmodeled kinematics) also effect 1D (z) positioning, and these 1D (z) errors were previously uncorrectable because of a lack of ability to measure the error.

Z ML model 1102 may be trained on fluorescent images of micropipette filled with a fluorescent injection solution that were taken during microinjection experiments. Images were annotated by drawing bounding boxes around the pipette tip and part of the shank of micropipette 118, and bounding boxes were labeled as the tip being "above focus", "in focus", or "below focus". "Above focus" means that the pipette tip was out-of-focus above the focal plane which is visibly discernable because no part of the pipette shank or tip is in focus. "In focus" means that the pipette tip was in-focus in the focal plane. "Below focus" means that the tip was out-of-focus below the focal plane which is visibly discernable because part of the pipette shank (but not the tip) is in focus.

Figure 13:
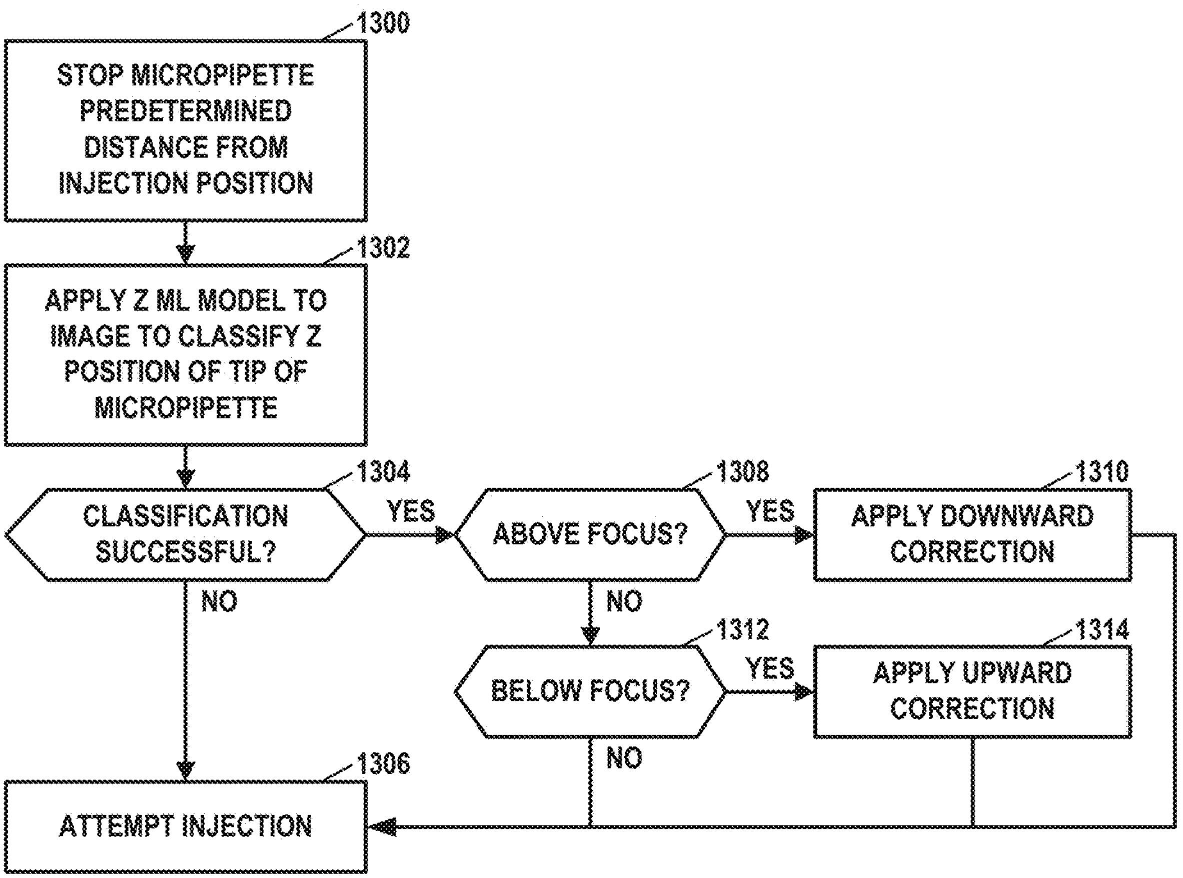
FIG. 13 is a flowchart illustrating an example 1-dimensional (z) position measurement and correction operation according to techniques of this disclosure.

Unlike the YOLOv5™ 2D (x, y) position measurements, the YOLOv5™ 1D (z) position measurements did not result in a numerical/quantifiable measurement of the error—it simply produced a ternary classification as "above focus", "in focus", or "below focus". Consequently, these measurements were not used in a Kalman Filter since the magnitude of the error was unknown. Therefore, the "raw" 1D (z) measurement information was used to make position corrections. To perform a 1D (z) positioning correction, micropipette 118 approaches the injection position and stops ~15 μm from the position. Injection control unit 518 then attempts a 1D (z) measurement using Z ML model 1102. If 1D (z) measurement is unsuccessful, injection control unit 518 may simply attempt injection. Otherwise, injection control unit 518 may move micropipette 118 a predetermined distance (e.g., 3 μm) down if the measurement was "above focus" or the predetermined distance (e.g., 3 μm) up if the measurement was "below focus" before attempting injection. A flowchart for 1D (z) YOLOv5™ position measurement and correction is shown in FIG. 13.

Even with pipette positioning correction, micropipette 118 can still miss cells during microinjection. For instance, robotic microinjection system 100 may inadequately correct the pipette position because the position measurements can still have measurement error after the Kalman Filter, or additional fluorescence in the field-of-view can make it challenging for the measurement system to detect the fluorescent tip of micropipette 118. Alternatively, cell detection unit 516 may imprecisely determine the cell's position, which would result in micropipette 118 injecting at a position that is noncoincident with the cell's true position. For these reasons, having a system capable of determining when a cell was unsuccessfully injected would be beneficial, so that robotic microinjection system 100 can reattempt injection on that cell.

In accordance with techniques of this disclosure, injection control unit 518 may further include an injection detection model 1104. Injection detection model 1104 may be an ML model, such as a YOLOv5™ model. Injection control unit 518 may apply injection detection model 1104 to detect successful cellular injection. With injection detection model 1104, injection control unit 518 can determine whether a cell was successfully injected and reattempt injection on cells that were not injected. This may mitigate issues described above because robotic microinjection system 100 can adjust the position of micropipette 118 before reattempting injection on previously unsuccessful injection attempt.

In addition to enabling reinjection attempts, use of injection detection model 1104 to detect injection may automatically provide experimental information about the number of successfully injected cells. It is important to know the number of injected cells that are being input into the post-microinjection processes like cellular/nuclear isolation, cell sorting, and sequencing processes; since each of these processes results in fewer cells being recovered than was input, its paramount to start sufficient number of injected cells so the injected cells can be detected during sequencing. Therefore, injection detection may be an automatic method for estimating the number of injected cells without the user needing to manually count each successful injection.

Injection detection model 1104 may be trained on fluorescent images of the cells being injected with a fluorescent injection solution. Images were annotated by drawing bounding boxes around the cells being injected and labeling the cell as being an "impalement" or a "miss". "Impaled" cells are discernable by the fluorescent solution being confined to a relatively round shape of approximately 10-20 μm with sharp, well-defined boundaries that contrast with the darker background. Conversely, "missed" cells do not exhibit any confined fluorescent injection solution and typically just look like a photograph of the pipette tip.

Figure 14:
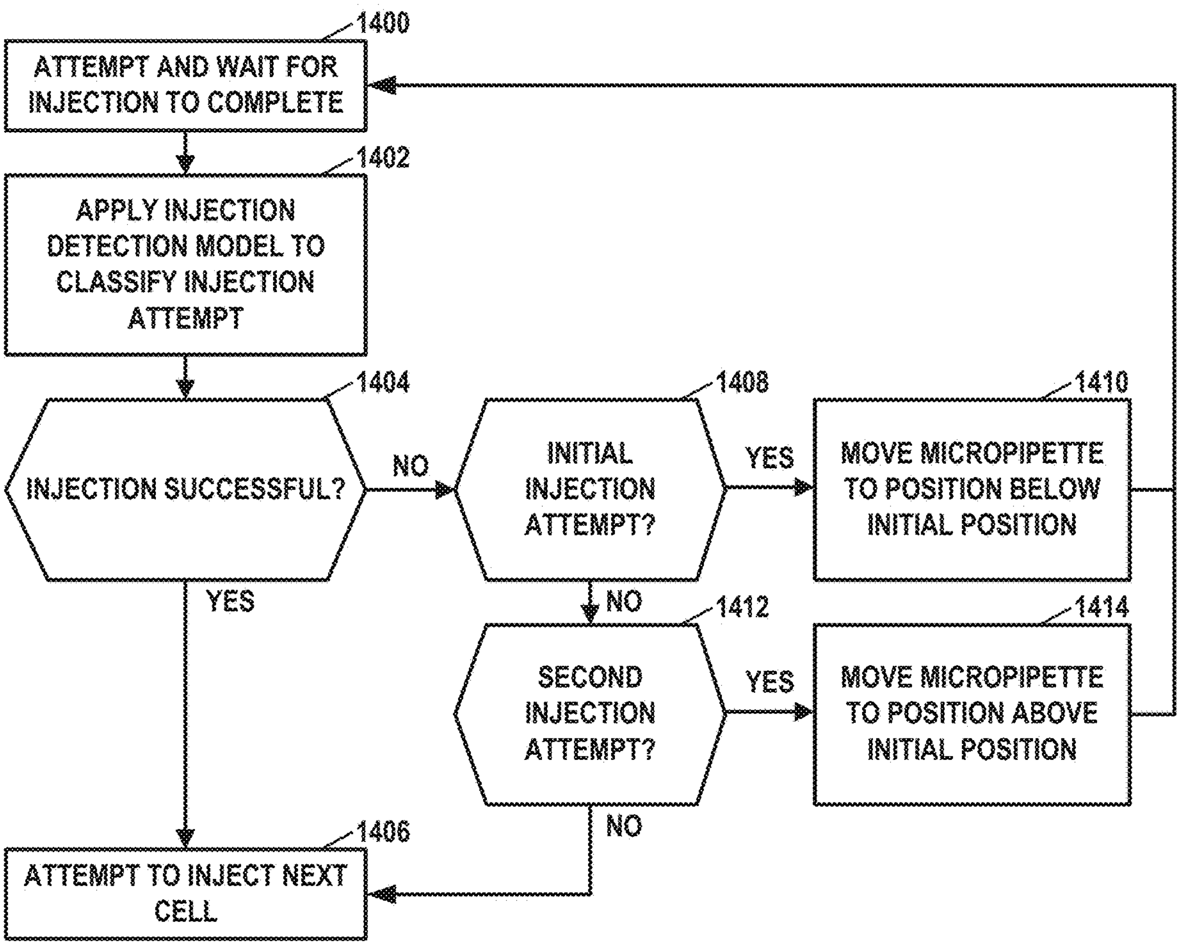
FIG. 14 is a flowchart illustrating an example operation for injection detection and reinjection attempts according to techniques of this disclosure.

During microinjection, injection control unit 518 may apply injection detection model 1104 to classify the injection status at the end of an injection duration. If injection detection model 1104 classifies the injection as successful, injection control unit 518 may proceed to the next cell for attempting injection. However, if injection detection model 1104 classified the injection as unsuccessful, injection control unit 518 may displace the tip of micropipette 118 by a predetermined amount (e.g., 3 μm) below the initial injection position in the z-axis. If injection detection model 1104 classifies the second injection attempt as unsuccessful, injection control unit 518 may displace micropipette 118 the predetermined amount (e.g., 3 μm) above the initial injection position. If neither the initial, second, or third injection attempt was successful, injection control unit 518 may proceed to the next cell so that injection control unit 518 does not indefinitely attempt injection on the same cell. Injection control unit 518 may compensate only for the z-axis because the (x, y) localization of the pipette tip and cells may be sufficiently accurate, whereas there can be much more error in the z-localization (e.g., because the focal plane is not actually a plane but a volume with a certain depth-of-field). Consequently, it may be more valuable to compensate the z-position and not compensate the (x, y) position because each reinjection attempt adds time to the microinjection process and reduces throughput. Injection control unit 518 may record data indicating whether injection detection model 1104 detected a successful injection to add to the total count of number of successfully injected cells. An example flowchart for the injection detection process is shown in FIG. 14.

Figure 12:
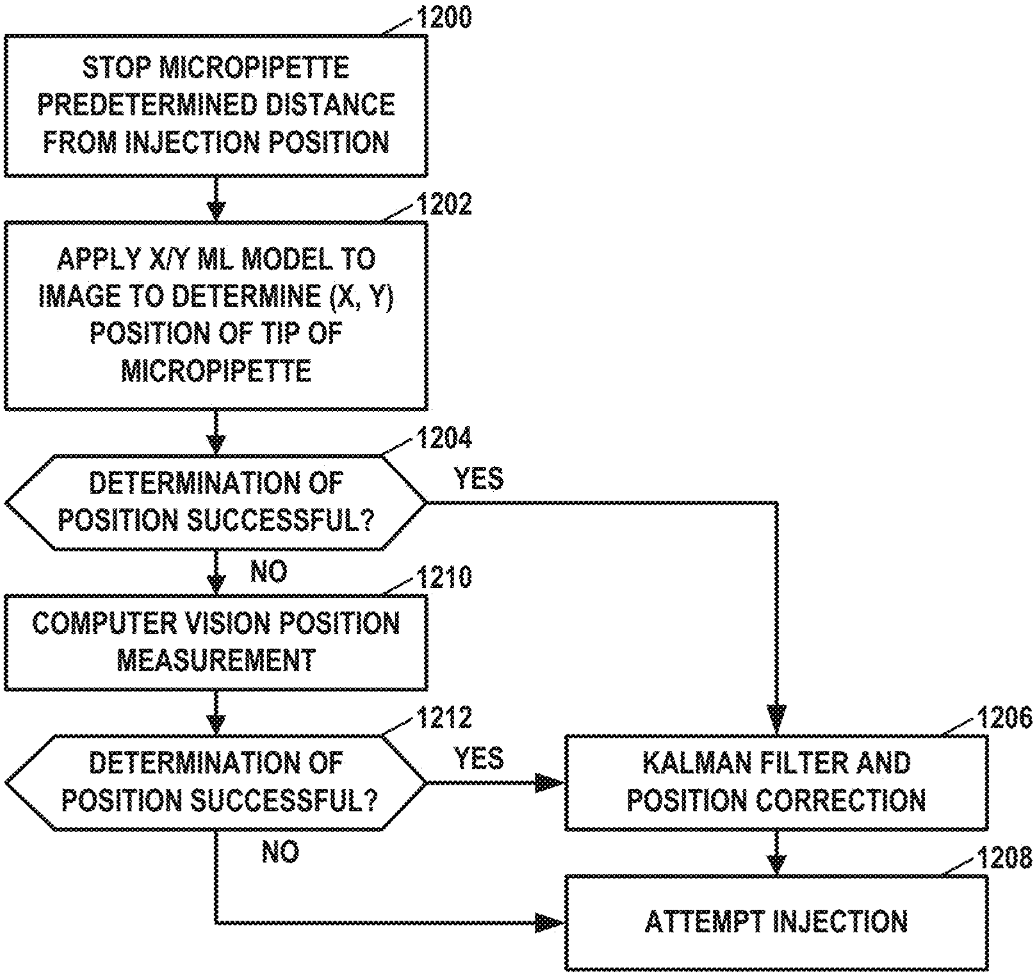
FIG. 12 is a flowchart illustrating an example 2-dimensional (x, y) micropipette position localization and position correction operation according to techniques of this disclosure.

FIG. 12 is a flowchart illustrating an example 2-dimensional (x, y) micropipette position localization and position correction operation according to techniques of this disclosure. In the example of FIG. 12, injection control unit 518 may stop micropipette 118 a predetermined distance (e.g., 15 μm) from a planned injection position (1200). Injection control unit 518 may then apply X/Y ML model 1100 to images to determine a 2D (x, y) position of the tip of micropipette 118 (1202). The images may be generated by microscope camera 110.

Injection control unit 518 may determine whether X/Y ML model 1100 was able to successfully determine the 2D position of the tip of micropipette 118 (1204). Injection control unit 518 may determine that a measurement is "successful" if X/Y ML model 1100 (YOLOv5™) returns a detection of the pipette tip. Injection control unit 518 may determine that the measurement is "unsuccessful" if X/Y ML model 1100 does not detect the tip when the tip is visible in the image (e.g., because of noise in the image).

If injection control unit 518 determines that X/Y ML model 1100 was able to successfully determine the 2D position of the tip of micropipette 118 ("YES" branch of 1204), injection control unit 518 may apply a Kalman Filter and position correction to the 2D position measurement (1206). Injection control unit 518 may then use micromanipulator 114 and pressure controller 106 to attempt injection (1208).

However, if injection control unit 518 determines that X/Y ML model 1100 was not able to successfully determine the 2D position of the tip of micropipette 118 ("NO" branch of 1204), injection control unit 518 may perform a computer vision position measurement process to determine the position of the tip of micropipette 118 (1210). An example computer vision position measurement process is described elsewhere in this disclosure, e.g., with respect to FIG. 6B. Injection control unit 518 may then determine whether the computer vision position measurement process was able to successfully determine the position of the tip of micropipette 118 (1212). Injection control unit 518 may determine that a measurement is "successful" if the computer vision position measurement process returns a detection of the pipette tip. Injection control unit 518 may determine that the measurement is "unsuccessful" if the computer vision position measurement process does not detect the tip when the tip is visible in the image (e.g., because of noise in the image). If the computer vision position measurement process was not able to successfully determine the position of the tip of micropipette 118 ("NO" branch of 1212), injection control unit 518 may then use micromanipulator 114 and pressure controller 106 to attempt injection (1208). Injection control unit 518 may attempt the injection when neither X/Y ML model 1100 nor the computer vision position measurement process was able to successfully determine the position of the tip of micropipette 118 because there may not be another way of refining the position of the tip of micropipette 118.

On the other hand, if the computer vision position measurement process was able to successfully determine the position of the tip of micropipette 118 ("YES" branch of 1212), injection control unit 518 may apply the Kalman Filter and position correction to the 2D position measurement (1206). Injection control unit 518 may then use micromanipulator 114 and pressure controller 106 to attempt injection (1208).

Thus, in the example of FIG. 12, computing device 102 may apply X/Y ML model 1100 to an image of micropipette 118 to measure an (x, y) position of a tip of 118 micropipette. Computing device 102 may apply a Kalman filter to the (x, y) position of the tip of micropipette 118. As part of controlling the robotic manipulator apparatus (micromanipulator 114) to insert micropipette 118 into the cell, computing device 102 may attempt injection of the cell based on the (x, y) position of the tip of micropipette 118.

FIG. 13 is a flowchart illustrating an example 1-dimensional (z) position measurement and correction operation according to techniques of this disclosure. In the example of FIG. 13, injection control unit 518 may stop micropipette 118 a predetermined distance (e.g., 15 μm) from a planned injection position (1300). Injection control unit 518 may then apply Z ML 1102 to one or more image to classify a Z position of the tip of micropipette 118 (1302). The images may be generated by microscope camera 110. Z ML model 1102 may classify the Z position of the tip of micropipette 118 as above focus, in focus, or below focus.

Injection control unit 518 may then determine whether classification of the 1D (z) position of the tip of micropipette 118 was successful (1304). Injection control unit 518 may determine that a measurement is "successful" if A ML model 1102 returns a detection of the pipette tip. Injection control unit 518 may determine that the measurement is "unsuccessful" if Z ML model 1102 does not detect the tip when the tip is visible in the image (e.g., because of noise in the image). In some examples, Z ML model 1102 may output confidence values for each of above focus, in focus, or below focus. Injection control unit 518 may determine that the classification of the 1D (z) position of the tip of micropipette 18 was not successful if none of the confidence values are above a predefined threshold. If classification of the 1D (z) position of the tip of micropipette 118 was not successful ("NO" branch of 1304), injection control unit 518 may then use micromanipulator 114 and pressure controller 106 to attempt injection (1306).

If injection control unit 518 determines that classification of the 1D (z) position of the tip of micropipette 118 was successful ("YES" branch of 1304), injection control unit 518 may determine whether the classification of the 1D (z) position of the tip of micropipette 118 is above focus (1308). If the classification of the 1D (z) position of the tip of micropipette 118 is above focus ("YES" branch of 1308), injection control unit 518 may apply downward correction to the 1D (z) position of the tip of micropipette 118 by a predetermined distance (e.g., 3 μm) (1310). Otherwise, if the classification of the 1D (z) position of the tip of micropipette 118 is not above focus ("NO" branch of 1308), injection control unit 518 may determine whether the classification of the 1D (z) position of the tip of micropipette 118 is below focus (1312). If the classification of the 1D (z) position of the tip of micropipette 118 is below focus ("YES" branch of 1312), injection control unit 518 may apply upward correction to the 1D (z) position of the tip of micropipette 118 by a predetermined distance (e.g., 3 μm) (1314). After applying upward or downward correction or after determining that the classification of the 1D (z) position of the tip of micropipette 118 is not below focus (i.e., the classification is "in focus") ("NO" branch of 1312), control unit 518 may use micromanipulator 114 and pressure controller 106 to attempt injection (1306).

Thus, in the example of FIG. 13, computing device 102 is further configured to apply Z ML model 1102 to an image of micropipette 118 to determine a classification of a z position of the tip of micropipette 118. Computing device 102 is configured to apply downward or upward correction, depending on the classification, to the position of the tip of micropipette 118 prior to attempting to insert micropipette 118 into the cell.

FIG. 14 is a flowchart illustrating an example operation for injection detection and reinjection attempts according to techniques of this disclosure. In the example of FIG. 14, injection control unit 518 may attempt an injection of a cell and wait for the injection to be completed (1400). Injection control unit 518 may then apply injection detection model 1104 to an image to classify the injection attempt as successful or unsuccessful (1402). Microscope camera 110 may generate the image after the injection attempt is complete.

Injection control unit 518 may then determine whether injection detection model 1104 classified the injection attempt as successful (1404). If injection detection model 1104 classified the injection attempt as successful ("YES" branch of 1404), injection control unit 518 may attempt to inject a next cell (1406). On the other hand, if injection detection model 1104 classified the injection attempt as unsuccessful ("NO" branch of 1404), injection control unit 508 may determine whether the injection attempt was an initial injection attempt (i.e., the first time that injection control unit 508 attempted to inject the cell) (1408). If the injection attempt was the initial injection attempt ("YES" branch of 1408), injection control unit 518 may move micropipette 118 to a position below the initial position of the injection attempt (1410). For instance, injection control unit 518 may move micropipette 118 to a position a predetermined distance (e.g., 3 μm or another distance) below the initial injection position. Injection control unit 518 may then attempt an injection of the cell again (1400).

If the injection attempt was not the initial injection attempt ("NO" branch of 1408), injection control unit 518 may determine whether the injection attempt was a second injection attempt (1412). If the injection attempt was the second injection attempt ("YES" branch of 1412), injection control unit 518 may move micropipette 118 to a position above the initial position of the injection attempt (1414). For instance, injection control unit 518 may move micropipette 118 to a position a predetermined distance (e.g., 3 μm or another distance) above the initial injection position. Injection control unit 518 may then attempt an injection of the cell again (1400). If the injection attempt was not the second injection attempt (i.e., the injection attempt was the third injection attempt) ("NO" branch of 1412), injection control unit 518 may attempt to inject a next cell (1406).

Thus, in the example of FIG. 14, injection control unit 518 may apply injection detection model 1104 (an ML model) to an image of micropipette 118 to classify an attempt to inject a cell as successful or unsuccessful. In response to determining that the attempt to inject the cell was unsuccessful, injection control unit 518 may move micropipette 118 upward or downward relative to an initial injection position. Injection control unit 518 may then reattempt to inject the respective cell.

Figure 15:
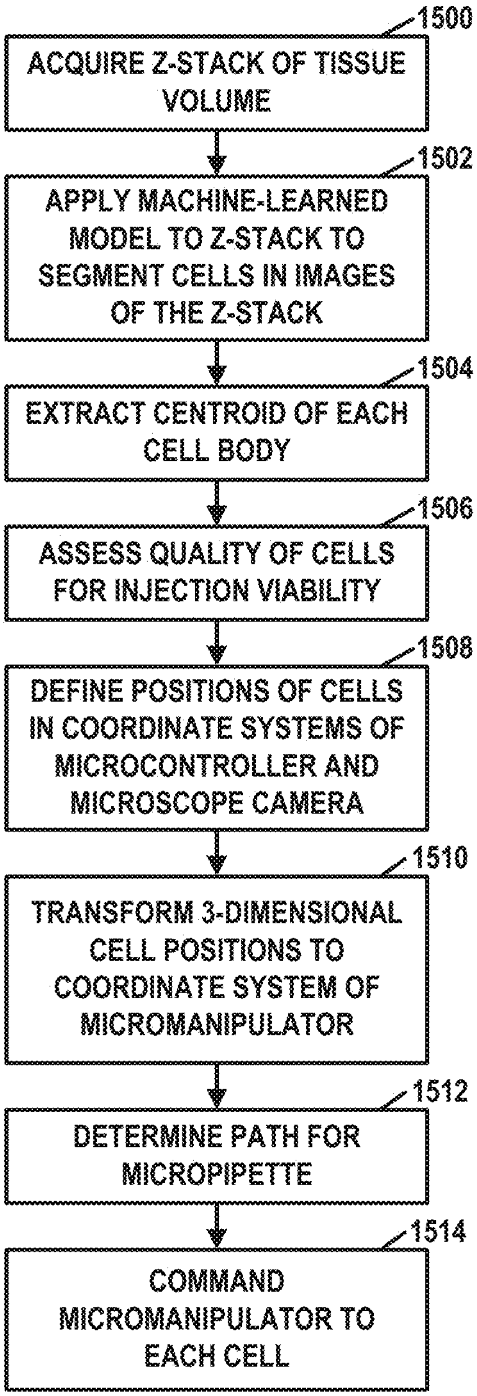
FIG. 15 is a flowchart illustrating an example operation for automatic cell detection and selection, and microinjection, according to techniques of this disclosure.

FIG. 15 is a flowchart illustrating an example operation for automatic cell detection and selection, and microinjection, according to techniques of this disclosure. The operation in FIG. 15 may be an alternative to the operation described in FIG. 8. In the example of FIG. 15, during determination of x-y coordinates of cells, cell detection unit 516 may acquire a z-stack of the tissue volume (1500). The user may specify a scan depth and distance between optical sections, and cell detection unit 516 automatically focuses on optical sections throughout the tissue volume and takes images of tissue sample 122.

After cell detection unit 516 acquires the z-stack, cell detection unit 516 may apply a machine-learned (ML) model (e.g., ML model 1106) to images in the z- stack to segment cells in the images (1502). By segmenting the cells in the images, cell detection unit 516 may determine bounding boxes around cells. The ML model may be implemented in one of a variety of ways. In some examples, the ML model is implemented as a CNN. For instance, the ML model may be implemented using a U-Net architecture or a mask region-based CNN (Mask R-CNN) architecture.

After cell segmentation, cell detection unit 516 may extract the centroid of each detected cell body (1504). Following location identification, cell detection unit 516 may assess the quality of each cell for its injection viability (1506). After the calibrations, the x, y, z position of micromanipulator 114 is known relative to microscope camera 1110 and focus controller 108, so the next step is for cell detection unit 516 to define the positions of cells relative to the same coordinate systems so they can be targeted for injection (1508). Finally, once the positions of micromanipulator 114 and the cells are known, injection control unit 518 targets the detected cells for barcoded microinjection. Depending on the tissue and the desired experiment, multiple tens of cells may be targeted for injection. Cell detection unit 516 may then transform the 3-dimensional cell positions into a coordinate system of micromanipulator 114 (1510). Injection control unit 518 may determine a path for micropipette 118 (1512). Once the path is determined, injection control unit 518 commands micromanipulator 114 to each subsequent cell for injection (1514). Cell detection unit 516 and injection control unit 518 may perform steps 1504 through 1512 in accordance with any of the examples provided with respect to corresponding steps of FIG. 8 or as described elsewhere in this disclosure.

Thus, in the example of FIG. 15, images captured by microscope camera 110 may be a z-stack of images of tissue sample 122 while scanning through a volume of tissue sample 122. Computing device 102 may be configured to, as part of applying the computer vision process to determine the 3-dimensional location of the respective cell, apply a machine-learned NN, such as U-Net or Mask R-CNN, to one or more of the images in the z-stack to segment cells. For each respective cell of the one or more cells, computing device 102 may determine the 3-dimensional location of the respective cell as the centroid of the 3-dimensional segmented cell.

In the examples, the algorithms, operations and functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), and Blu-ray disc, where disks usually reproduce data magnetically, while discs reproduce data optically with lasers. Combinations of the above should also be included within the scope of computer-readable media.

The invention claimed is:

1. A system for injecting a substance into a plurality of cells of a cell population at a plurality of depths in a tissue sample, the system comprising:

a robotic manipulator apparatus configured to hold and position a micropipette;

an injector controller;

a robotic apparatus configured to manipulate a focal plane of a microscope; and a computing device configured to, for each respective cell of the plurality of cells within the tissue sample:

perform image processing on images formed by the microscope and captured by a microscope camera to automatically detect the respective cell;

automatically determine a 3-dimensional location of the detected respective cell within the tissue sample based on the image processing;

control, based on the 3-dimensional location of the detected respective cell, the robotic manipulator apparatus to insert the micropipette into the respective cell within the tissue sample; and control the injector controller to eject the substance out of the micropipette and into the detected respective cell within the tissue sample.

2. The system of claim 1, wherein the substance is a molecular barcode that corresponds to the cell population.

3. The system of claim 1, wherein the cell population is defined based at least in part on:

a spatial location within the tissue sample, or a function or a characteristic of cells in the cell population.

4. The system of claim 1, wherein the system further comprises electrical hardware configured to perform electroporation on the tissue sample.

5. The system of claim 1, wherein the computing device is configured to perform the image processing by applying a computer vision process to identify the 3-dimensional location of the detected respective cell.

6. The system of claim 5, wherein:

the images captured by the microscope camera are a z-stack of images of the tissue sample while scanning through a volume of the tissue sample, and the computing device is configured to, as part of applying the computer vision process:

generate a maximum intensity projection (MIP) based on the z-stack of images;

segment the plurality of cells from the MIP; and for each respective cell of the plurality of cells, determine an x-y coordinate of a centroid of the respective cell and a z-coordinate of the respective cell based on a most in-focus optical section of the respective cell.

7. The system of claim 6, wherein the computing device is configured to, as part of determining the z-coordinate of the respective cell:

compute a focus metric, wherein the focus metric is one of a pixel intensity, a Tenengrad variance, a normalized variance, or a Vollath's autocorrelation for each image of the z-stack for the respective cell;

fit a gaussian distribution to the focus metric for the images; and select a mean of the gaussian distribution as the z-coordinate of the respective cell.

8. The system of claim 5, wherein:

the images captured by the microscope camera are a z-stack of images of the tissue sample while scanning through a volume of the tissue sample, and the computing device is configured to, as part of applying the computer vision process to determine the 3-dimensional location of the respective cell:

apply a machine-learned neural network (NN) to one or more of the images in the z-stack to segment cells; and for each respective cell of the plurality of cells, determine the 3-dimensional location of the respective cell as the centroid of the 3-dimensional segmented cell.

9. The system of claim 1, wherein the computing device is further configured to assess the viability of the detected respective cell using a logistic regression model trained on image-based features of successfully injected cells to predict a probability of a successful injection of the respective cell.

10. The system of claim 1, wherein the computing device is further configured to determine a trajectory of the micropipette among the plurality of cells of the cell population.

11. The system of claim 1, wherein:

the computing device is further configured to:

segment a shank of the micropipette in an image;

fit lines to the segmented shank of the micropipette;

extrapolate and intersect the lines to measure an (x, y) position of a tip of the micropipette; and apply a Kalman filter to the (x, y) position of the tip of the micropipette, and the computing device is configured to, as part of controlling the robotic manipulator apparatus to insert the micropipette into the detected respective cell, attempt injection of the detected respective cell based on the (x, y) position of the tip of the micropipette.

12. The system of claim 1, wherein:

the computing device is further configured to:

apply a ML model to an image of the micropipette to measure an (x, y) position of a tip of the micropipette;

apply a Kalman filter to the (x, y) position of the tip of the micropipette, and the computing device is configured to, as part of controlling the robotic manipulator apparatus to insert the micropipette into the detected respective cell, attempt injection of the respective cell based on the (x, y) position of the tip of the micropipette.

13. The system of claim 1, wherein:

the computing device is further configured to apply a ML model to an image of the micropipette to determine a classification of a z position of the tip of the micropipette, and the computing device is configured to apply downward or upward correction, depending on the classification, to the position of the tip of the micropipette prior to attempting to insert the micropipette into the detected respective cell.

14. The system of claim 1, wherein:

the computing device is further configured to:

apply a ML model to an image of the micropipette to classify an attempt to inject the detected respective cell as successful or unsuccessful; and in response to determining that the attempt to inject the detected respective cell was unsuccessful:

move the micropipette upward or downward relative to an initial injection position; and reattempt to inject the detected respective cell.

15. A method for injecting a substance into a plurality of cells of a cell population at a plurality of depths within a tissue sample, the method comprising, for each respective cell of the plurality of cells:

performing, by a computing device of a robotic microinjection system, image processing on images from a microscope camera configured to capture the images formed by a microscope, to automatically detect the respective cell;

automatically determining, by the computing device, a 3-dimensional location of the detected respective cell within the tissue sample based on the image processing;

controlling, by the computing device, based on the 3-dimensional location of the detected respective cell, a robotic manipulator apparatus to insert a micropipette into the respective cell within the tissue sample; and controlling, by the computing device, an injector controller to eject the substance out of the micropipette and into the detected respective cell within the tissue sample.

16. The method of claim 15, wherein:

the images captured by the microscope camera are a z-stack of images of the tissue sample while scanning through a volume of the tissue sample, and determining the 3-dimensional location of the respective cell comprises:

using, by the computing device, the microscope camera to generate a z-stack of images of the tissue sample while scanning through a volume of the tissue sample;

generating, by the computing device, a maximum intensity projection (MIP) based on the z-stack of images;

segmenting, by the computing device, the plurality of cells from the MIP; and for each respective cell of the plurality of cells, determining, by the computing device, an x-y coordinate of a centroid of the respective cell and a z-coordinate of the respective cell based on a most in-focus optical section of the respective cell.

17. The method of claim 16, wherein determining the z-coordinate of the respective cell comprises:

computing, by the computing device, a focus metric, wherein the focus metric is one of a pixel intensity, a Tenengrad variance, a normalized variance, or a Vollath's autocorrelation for each image of the z-stack for the respective cell;

fitting, by the computing device, a gaussian distribution to the focus metric for the images; and selecting, by the computing device, a mean of the gaussian distribution as the z-coordinate of the respective cell.

18. The method of claim 15, wherein the images captured by the microscope camera are a z-stack of images of the tissue sample while scanning through a volume of the tissue sample, the method further comprising performing the image processing by applying a computer vision process to determine the 3-dimensional location of the respective cell, wherein the computer vision process comprises:

applying, by the computing device, a machine-learned neural network (NN) to one or more of the images in the z-stack to segment cells; and for each respective cell of the plurality of cells, determining, by the computing device, the 3-dimensional location of the respective cell as the centroid of the 3-dimensional segmented cell.

19. The method of claim 15, further comprising assessing the viability of the detected respective cell using a logistic regression model trained on image-based features of successfully injected cells to predict a probability of a successful injection of the detected respective cell.

20. The method of claim 15, wherein the method further comprises correcting, by the computing device, a micropipette trajectory to a cell in the event of micropipette positioning inaccuracy using computer vision or machine learning based algorithms and a Kalman filter.

21. The method of claim 15, wherein the method further comprises controlling a robotic apparatus to manipulate a focal plane of the microscope.

22. A non-transitory computer-readable storage medium having instructions stored thereon that configure a robotic microinjection system to, for each respective cell of a plurality of cells of a cell population at a plurality of depths within a tissue sample:

perform image processing on images formed by the microscope and captured by a microscope camera to automatically detect the respective cell;

automatically determine a 3-dimensional location of the detected respective cell within the tissue sample based on the image processing;

control, based on the 3-dimensional location of the detected respective cell, a robotic manipulator apparatus to insert a micropipette into the respective cell within the tissue sample; and control an injector controller to eject the substance out of the micropipette and into the detected respective cell within the tissue sample.

* * * * *